United States Patent
Cole et al.

(10) Patent No.: US 9,926,315 B2
(45) Date of Patent: Mar. 27, 2018

(54) TRIAZOLOPYRIDINE COMPOUNDS AND METHODS FOR THE TREATMENT OF CYSTIC FIBROSIS

(71) Applicant: Flatley Discovery Lab, LLC, Charlestown, MA (US)

(72) Inventors: Bridget M. Cole, Quincy, MA (US); Richard A. Nugent, Ashland, MA (US); Paul T. Smith, Jr., Brooklyn, NY (US)

(73) Assignee: Flatley Discovery Lab, LLC, Charlestown, MA (US)

( * ) Notice: Subject to any disclaimer, the term of this patent is extended or adjusted under 35 U.S.C. 154(b) by 0 days.

(21) Appl. No.: 15/409,991

(22) Filed: Jan. 19, 2017

(65) Prior Publication Data

US 2017/0233388 A1    Aug. 17, 2017

Related U.S. Application Data

(62) Division of application No. 14/876,428, filed on Oct. 6, 2015, now Pat. No. 9,573,948.

(60) Provisional application No. 62/060,311, filed on Oct. 6, 2014.

(51) Int. Cl.
| | |
|---|---|
| C07D 471/02 | (2006.01) |
| C07D 471/04 | (2006.01) |
| A61K 31/437 | (2006.01) |
| A61K 31/496 | (2006.01) |
| A61K 45/06 | (2006.01) |
| A61K 31/4196 | (2006.01) |
| A61K 31/4439 | (2006.01) |
| A61K 31/444 | (2006.01) |
| A61K 31/4545 | (2006.01) |
| A61K 31/519 | (2006.01) |
| C07D 487/04 | (2006.01) |

(52) U.S. Cl.
CPC ........ *C07D 471/04* (2013.01); *A61K 31/4196* (2013.01); *A61K 31/437* (2013.01); *A61K 31/444* (2013.01); *A61K 31/4439* (2013.01); *A61K 31/4545* (2013.01); *A61K 31/496* (2013.01); *A61K 31/519* (2013.01); *A61K 45/06* (2013.01); *C07D 487/04* (2013.01)

(58) Field of Classification Search
CPC .................................................. C07D 471/04
USPC ......................................................... 546/119
See application file for complete search history.

(56) References Cited

U.S. PATENT DOCUMENTS 9,573,948 B2 *   2/2017   Cole .................. A61K 31/4196

* cited by examiner

*Primary Examiner* — Nizal Chandrakumar
(74) *Attorney, Agent, or Firm* — Elmore Patent Law Group, P.C.; Edgar W. Harlan; Carolyn S. Elmore, Esq.

(57) ABSTRACT

The invention relates to a compound of Formula I or IA and methods of treating cystic fibrosis comprising the step of administering a therapeutically effective amount of a compound of Formula I or IA to a patient in need thereof:

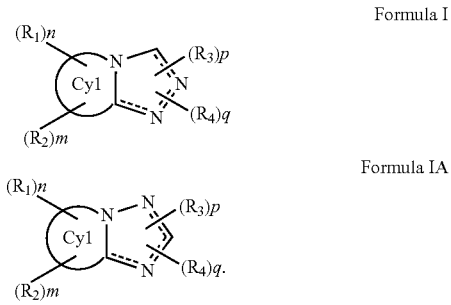

9 Claims, No Drawings

TRIAZOLOPYRIDINE COMPOUNDS AND METHODS FOR THE TREATMENT OF CYSTIC FIBROSIS

RELATED APPLICATIONS

This application is a divisional of application Ser. No. 14/876,428 filed on Oct. 6, 2015, which claims the benefit of U.S. Provisional Application No. 62/060,311, filed on Oct. 6, 2014. The entire teachings of the above applications are incorporated herein by reference.

BACKGROUND

Cystic fibrosis (CF) is a lethal, recessive, genetic disease affecting approximately 1 in 2500 live births among Caucasians. (Cohen-Cymberknoh, M. et al., *Am. J. Respir. Crit. Care Med.* 1463-1471, 2011; Boat et al., The Metabolic Basis of Inherited Disease, 6th ed., pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. (Hantash, F: U.S. Patent Application No. 20060057593). The CF gene codes for a cAMP/PKA-dependent, ATP-requiring, membrane chloride ion channel, generally found in the apical membranes of many secreting epithelia and is known as CFTR (cystic fibrosis transmembrane conductance regulator). There are currently over 1900 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cuthbert A W, *British Journal of Pharmacology*, 163(1), 173-183, 2011).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et al., *Am. J. Respir. Crit. Care Med.* 1463-1471, 2011).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et al., *Expert Opin Pharmacother.* 10(7), 1191-202, 2009).

SUMMARY

The invention relates to a compound of Formula I or IA and methods of treating CFTR (cystic fibrosis transmembrane conductance regulator) mediated diseases, in particular cystic fibrosis, comprising the step of administering a therapeutically effective amount of a compound of Formula I or IA to a patient in need thereof:

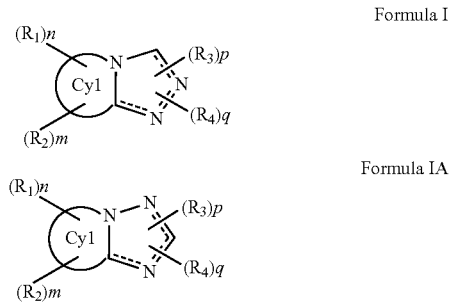

or a pharmaceutically acceptable salt ester or prodrug thereof;

wherein ===== represents a single or double bond;

each n, m, p and q is independently selected from 0, 1, 2 and 3;

$Cy_1$ is selected from heteroaryl, substituted heteroaryl, heterocyclic and substituted heterocyclic;

each $R_1$, $R_2$, $R_3$ and $R_4$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_1$ and $R_2$ groups or two $R_3$ and $R_4$ groups or an $R_{100}$ and $R_{101}$ groups together with the atoms to which they are attached and any intervening atoms may form an additional optionally substituted, 3, 4, 5, 6 or 7 membered ring; Alternatively, two $R_3$ groups or two $R_4$ groups together may form an oxo, vinyl or substituted vinyl group; and, each $R_{100}$ and $R_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

DETAILED DESCRIPTION OF THE INVENTION

The invention relates to a compound of Formula I or IA and methods of treating cystic fibrosis comprising the step of administering a therapeutically effective amount of a compound of Formula I or IA to a patient in need thereof:

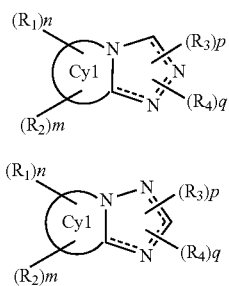

Formula I

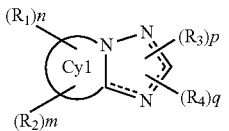

Formula IA or a pharmaceutically acceptable salt, ester or prodrug thereof;
wherein ===== represents a single or double bond;
each n, m, p and q is independently selected from 0, 1, 2 and 3;
$Cy_1$ is selected from heteroaryl, substituted heteroaryl, heterocyclic and substituted heterocyclic;
each $R_1$, $R_2$, $R_3$ and $R_4$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_1$ and $R_2$ groups or two $R_3$ and $R_4$ groups or an $R_{100}$ and $R_{101}$ groups together with the atoms to which they are attached and any intervening atoms may form an additional optionally substituted, 3, 4, 5, 6 or 7 membered ring; alternatively, two $R_1$ groups, two $R_2$ groups, two $R_3$ groups or two $R_4$ groups together may form an oxo, vinyl or substituted vinyl group; and,
each $R_{100}$ and $R_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound of Formula II or IIA and methods of treating cystic fibrosis comprising the step of administering a therapeutically effective amount of a compound of Formula II or IIA to a patient in need thereof:

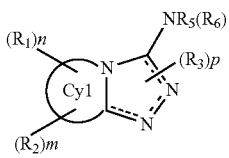

Formula II

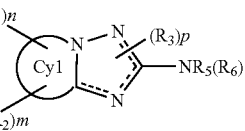

Formula IIA or a pharmaceutically acceptable salt, ester or prodrug thereof;
wherein ===== represents a single or double bond;
each n, m, p and q is independently selected from 0, 1, 2 and 3;
$Cy_1$ is selected from heteroaryl, substituted heteroaryl, heterocyclic and substituted heterocyclic;
each $R_1$, $R_2$, and $R_3$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; alternatively two $R_1$ and $R_2$ groups or two $R_3$ groups or an $R_{100}$ and an $R_{101}$ group together with the atoms to which they are attached and any intervening atoms may form an additional optionally substituted, 3, 4, 5, 6 or 7 membered ring;
each $R_5$ and $R_6$ is independently selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively, $R_5$ and $R_6$ groups together with the atoms to which they are attached and any intervening atoms may form an additional optionally substituted, 3, 4, 5, 6 or 7 membered ring; alternatively, two $R_1$ groups or two $R_2$ groups together may form an oxo, vinyl or substituted vinyl group; and,
each $R_{100}$ and $R_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound of Formula III or IIIA and methods of treating cystic fibrosis comprising the step of administering a therapeutically effective amount of a compound of Formula III or IIIA to a patient in need thereof:

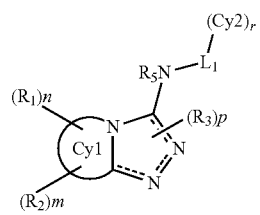

Formula III

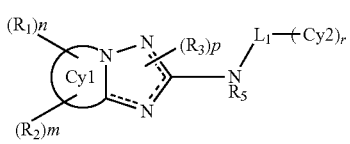

Formula IIIA or a pharmaceutically acceptable salt, ester or prodrug thereof;
wherein ===== represents a single or double bond;
each n, m, p and q is independently selected from 0, 1, 2 and 3;
r is 1, 2 or 3;
Cy1 is selected from heteroaryl, substituted heteroaryl, heterocyclic and substituted heterocyclic;
Cy2 is selected from aryl, substituted aryl, heteroaryl, substituted heteroaryl, heterocyclic, substituted heterocyclic, carbocyclic and substituted carbocyclic;
$L_1$ is absent or a linker; preferably an alkyl or substituted alkyl;
each $R_1$, $R_2$, and $R_3$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —$OR_{100}$, —$NR_{100}R_{101}$, —$C(O)R_{100}$, —$C(O)OR_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$; alternatively two R$_1$ and R$_2$ groups or two R$_3$ groups or an R$_{100}$ and an R$_{101}$ group together with the atoms to which they are attached and any intervening atoms may form an additional optionally substituted, 3, 4, 5, 6 or 7 membered ring; alternatively, two R$_1$ groups or two R$_2$ groups together may form an oxo, vinyl or substituted vinyl group;

R$_5$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl;

each R$_{100}$ and R$_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound of Formula IV or IVA and methods of treating cystic fibrosis comprising the step of administering a therapeutically effective amount of a compound of Formula IV or IVA to a patient in need thereof:

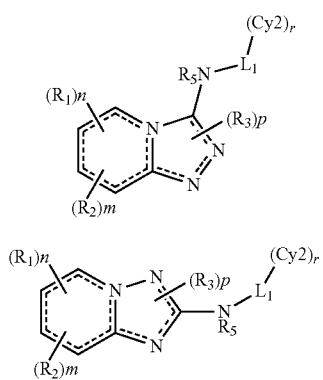

Formula IV

Formula IVA or a pharmaceutically acceptable salt, ester or prodrug thereof;

wherein ===== represents a single or double bond;

each n, m, p and q is independently selected from 0, 1, 2 and 3;

r is 1, 2 or 3;

Cy2 is selected from aryl, substituted aryl, heteroaryl, substituted heteroaryl, heterocyclic, substituted heterocyclic, carbocyclic and substituted carbocyclic;

L$_1$ is a absent or a linker; preferably an alkyl or substituted alkyl;

each R$_1$, R$_2$, and R$_3$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —OR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$; alternatively two R$_1$ and R$_2$ groups or two R$_3$ groups or an R$_{100}$ and an R$_{101}$ group together with the atoms to which they are attached and any intervening atoms may form an additional optionally substituted, 3, 4, 5, 6 or 7 membered ring; alternatively, two R$_1$ groups or two R$_2$ groups together may form an oxo, vinyl or substituted vinyl group;

R$_5$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; and, each R$_{100}$ and R$_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound of Formula V or VA and methods of treating cystic fibrosis comprising the step of administering a therapeutically effective amount of a compound of Formula V or VA to a patient in need thereof:

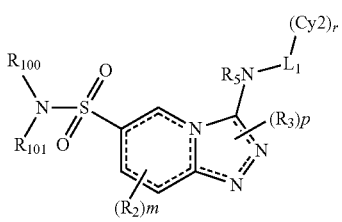

Formula V

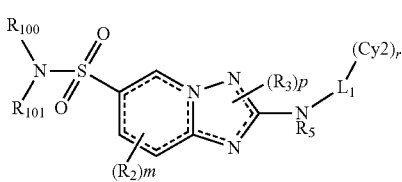

Formula VA or a pharmaceutically acceptable salt, ester or prodrug thereof;

wherein ===== represents a single or double bond;

each n, m, p and q is independently selected from 0, 1, 2 and 3;

r is 1, 2 or 3;

Cy2 is selected from aryl, substituted aryl, heteroaryl, substituted heteroaryl, heterocyclic, substituted heterocyclic, carbocyclic and substituted carbocyclic;

L$_1$ is a absent or a linker; preferably an alkyl or substituted alkyl;

each R$_2$, and R$_3$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, —OR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, —N$_3$; alternatively two R$_2$ groups or two R$_3$ groups or an R$_{100}$ and an R$_{101}$ group together with the atoms to which they are attached and any intervening atoms may form an additional optionally substituted, 3, 4, 5, 6 or 7 membered ring; alternatively, two R$_1$ groups or two R$_2$ groups together may form an oxo, vinyl or substituted vinyl group;

R$_5$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; and, each R$_{100}$ and R$_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound of Formula VI or VIA and methods of treating cystic fibrosis comprising the step of administering a therapeutically effective amount of a compound of Formula VI or VIA to a patient in need thereof:

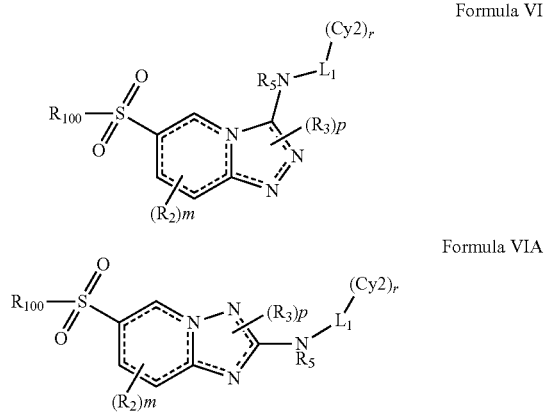

Formula VI

Formula VIA or a pharmaceutically acceptable salt, ester or prodrug thereof;

wherein ===== represents a single or double bond;

each z, n, m, p and q is independently selected from 0, 1, 2 and 3;

Cy3 is selected from heteroaryl, substituted heteroaryl, heterocyclic, substituted heterocyclic, carbocyclic and substituted carbocyclic;

each $R_1$, $R_2$, $R_3$, and $R_7$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl, $-OR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$, $-CF_3$, $-CN$, $-NO_2$, $-N_3$; alternatively two $R_1$ and $R_2$ groups or two $R_3$ groups, or two $R_7$ groups or an $R_{100}$ and an $R_{101}$ group together with the atoms to which they are attached and any intervening atoms may form an additional optionally substituted, 3, 4, 5, 6 or 7 membered ring; alternatively, two $R_1$ groups, or two $R_2$ groups, or two $R_7$ groups together may form an oxo, vinyl or substituted vinyl group; and, each $R_{100}$ and $R_{101}$ is selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; preferably, $R_{100}$ is phenyl or substituted phenyl.

In a preferred embodiment, the invention relates to a compound wherein Cy1 is selected from:

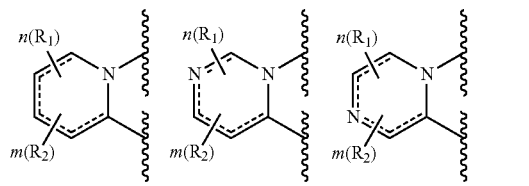

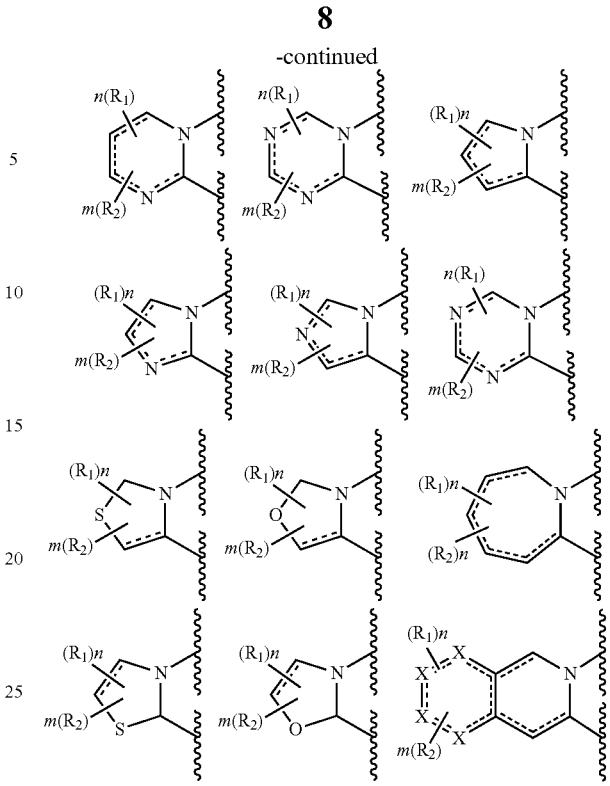

wherein each X is independently $-C(R_{103})(R_{104})-$, $-N(R_{103})-$, $-S-$ or $-O-$;

wherein each $R_{103}$ and $R_{104}$ is independently selected from absent, hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

In a preferred embodiment, the invention relates to a compound wherein Cy2 is selected from:

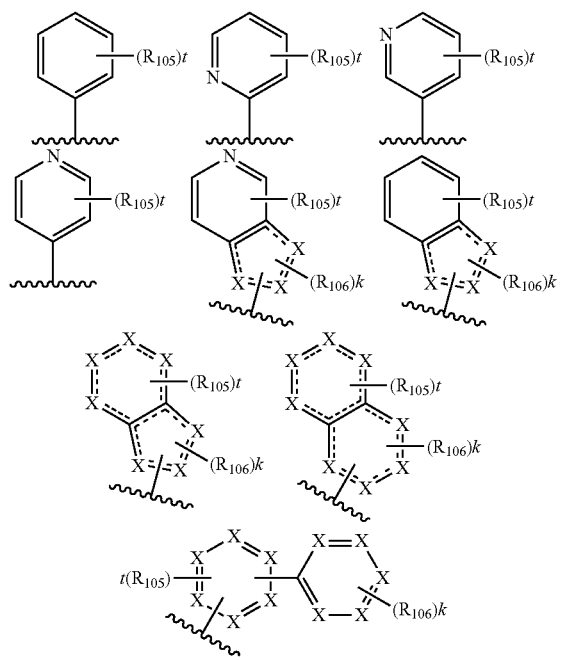

-continued

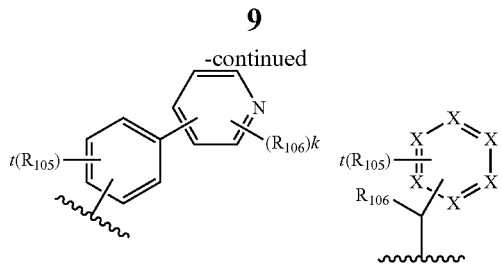

wherein t is 1, 2, 3, 4 or 5;
k is 1, 2, 3, 4 or 5;
each X is independently —C($R_{103}$)($R_{104}$)—, —N($R_{103}$)—, —S— or —O—;
wherein each $R_{103}$ and $R_{104}$ is independently selected from absent, hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl;
each $R_{105}$ and $R_{106}$ is independently selected from absent, hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively, two $R_{105}$ groups or two $R_{106}$ groups together may form an oxo, vinyl or substituted vinyl group.

In a preferred embodiment, $L_1$ is selected from:

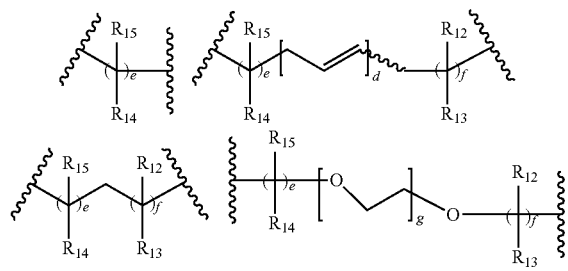

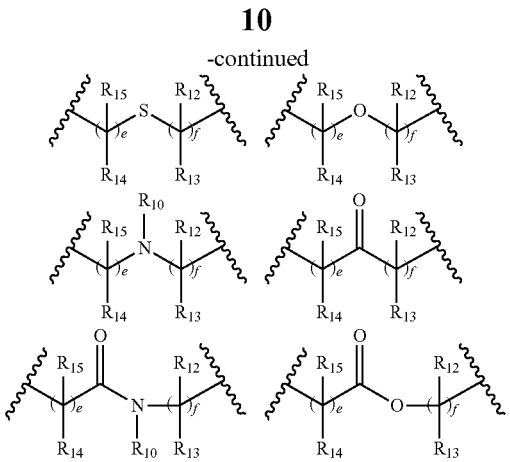

wherein
g is an integer between about 1 and about 1000, preferably between 1 and 100, preferably between 1 and 10;
e and f is independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30;
d is 1, 2, 3, 4, 5, 6 or 7;
each $R_{10}$, $R_{11}$, $R_{12}$, $R_{13}$, $R_{14}$, $R_{15}$, and $R_{16}$ is independently selected from absent, hydrogen, halogen, —$OR_{20}$, —$SR_{20}$, —$NR_{20}R_{21}$, —C(O)$R_{20}$, —C(O)O$R_{20}$, —C(O)N$R_{20}R_{21}$, —N($R_{20}$)C(O)$R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; alternatively two $R_{10}$, $R_{11}$, $R_{12}$, $R_{13}$, $R_{14}$, $R_{15}$, and $R_{16}$ together with the atoms to which they are attached form an optionally substituted 3, 4, 5, 6 or 7 membered ring; and,
each $R_{20}$ and $R_{21}$ is selected from hydrogen, halogen, aliphatic, substituted aliphatic, aryl or substituted aryl.

In a more preferred embodiment, a compound of formula I is selected from Table A or a pharmaceutically acceptable salt thereof:

TABLE A

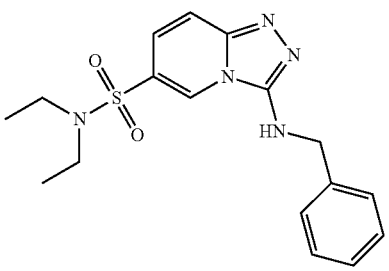 [SMILES: CCN(CC)S(=O)(=O)c1ccc2nnc(NCc3ccccc3)n2c1]

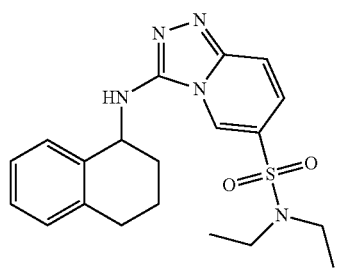 [SMILES: CCN(CC)S(=O)(=O)c1ccc2nnc(NC3CCCc4ccccc43)n2c1]

TABLE A-continued
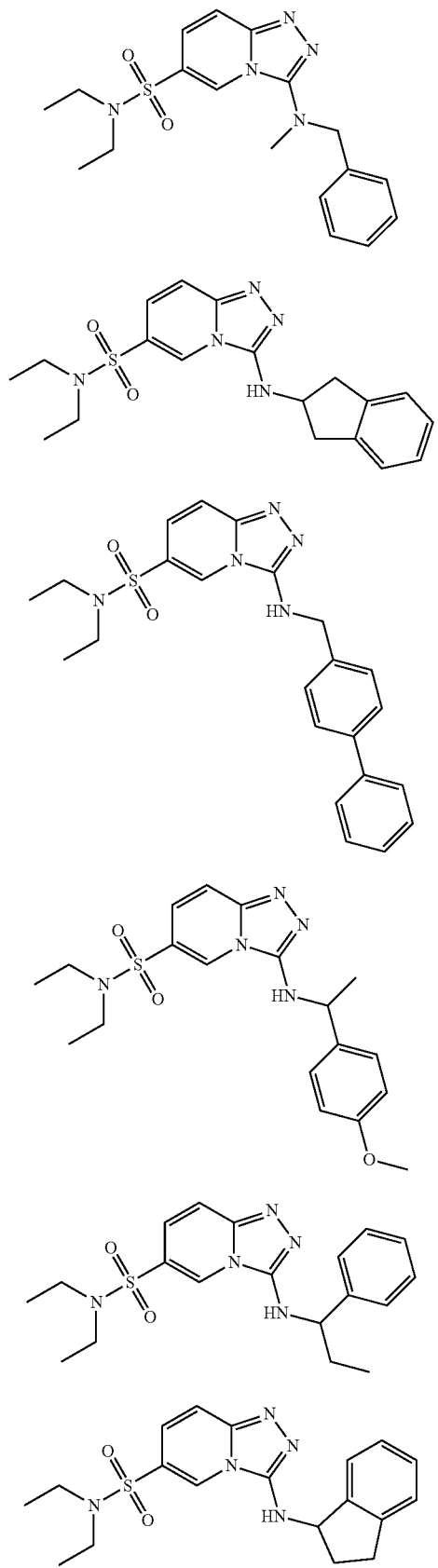

TABLE A-continued
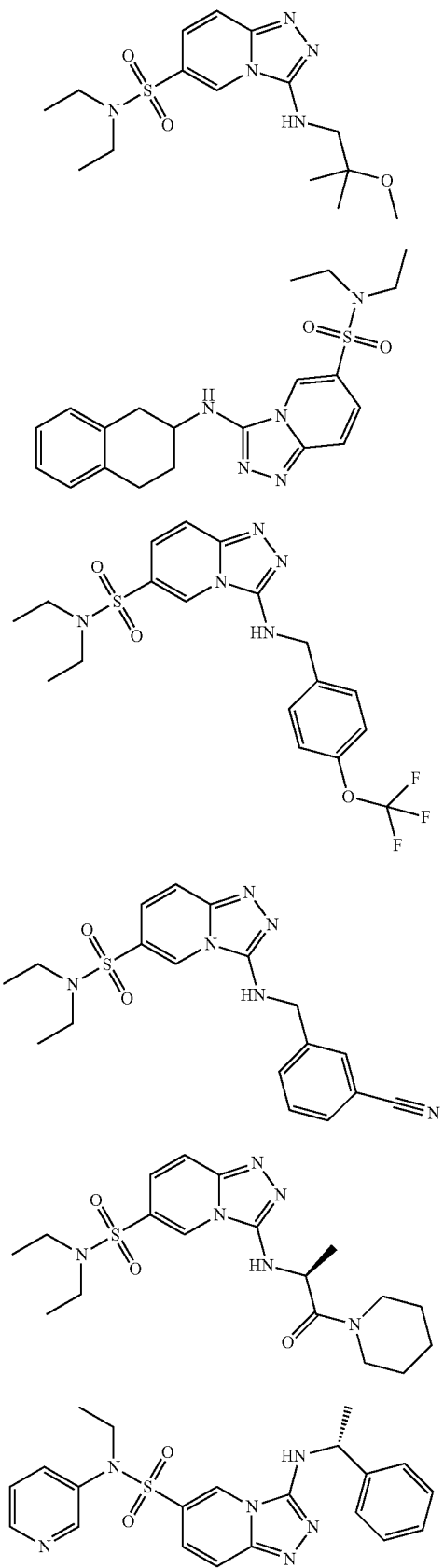

TABLE A-continued
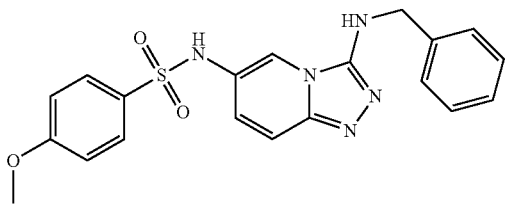 [SMILES: COc1ccc(S(=O)(=O)Nc2ccc3nnc(NCc4ccccc4)n3c2)cc1]
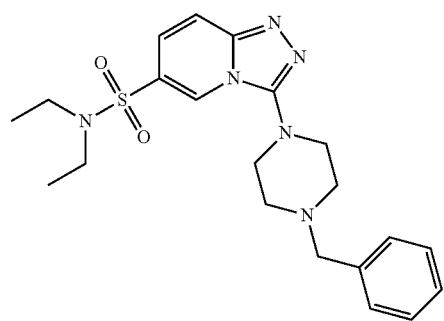 [SMILES: CCN(CC)S(=O)(=O)c1ccc2nnc(N3CCN(Cc4ccccc4)CC3)n2c1]
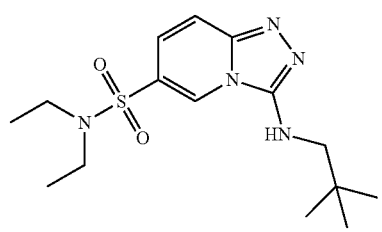 [SMILES: CCN(CC)S(=O)(=O)c1ccc2nnc(NCC(C)(C)C)n2c1]
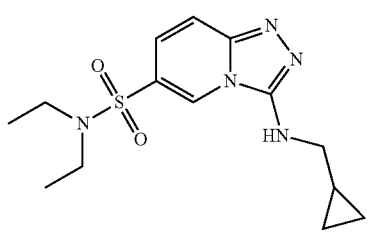 [SMILES: CCN(CC)S(=O)(=O)c1ccc2nnc(NCC3CC3)n2c1]
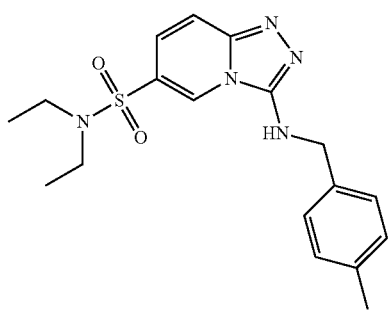 [SMILES: CCN(CC)S(=O)(=O)c1ccc2nnc(NCc3ccc(C)cc3)n2c1]
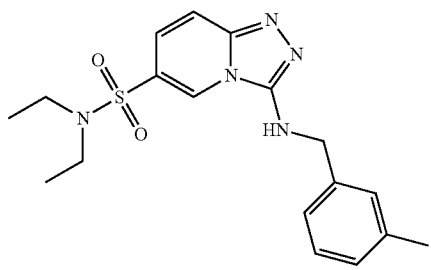 [SMILES: CCN(CC)S(=O)(=O)c1ccc2nnc(NCc3cccc(C)c3)n2c1]

TABLE A-continued
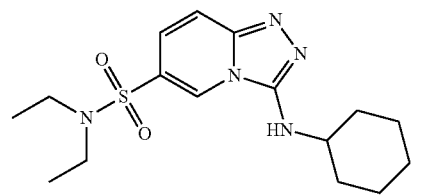 [SMILES: CCN(CC)S(=O)(=O)c1ccc2nnc(NC3CCCCC3)n2c1]
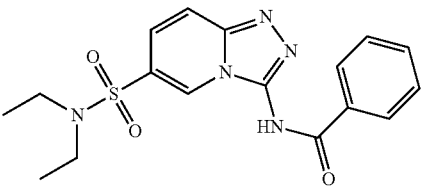 [SMILES: CCN(CC)S(=O)(=O)c1ccc2nnc(NC(=O)c3ccccc3)n2c1]
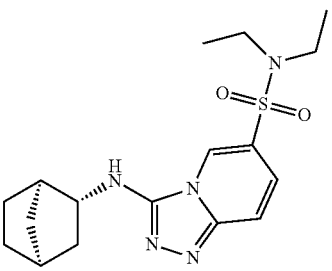 [SMILES: CCN(CC)S(=O)(=O)c1ccc2nnc(N[C@@H]3C[C@H]4CC[C@@H]3C4)n2c1]
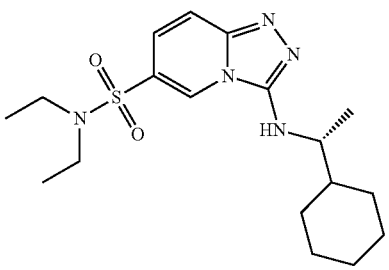 [SMILES: CCN(CC)S(=O)(=O)c1ccc2nnc(N[C@H](C)C3CCCCC3)n2c1]
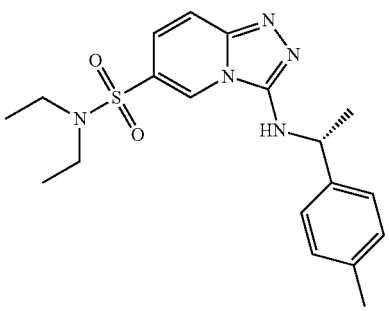 [SMILES: CCN(CC)S(=O)(=O)c1ccc2nnc(N[C@H](C)c3ccc(C)cc3)n2c1]
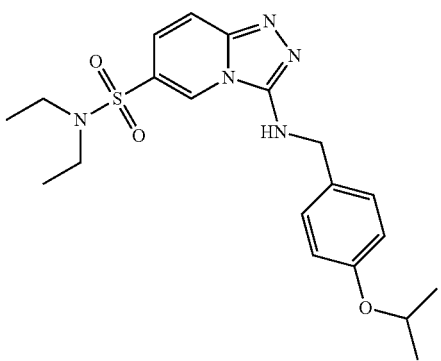 [SMILES: CCN(CC)S(=O)(=O)c1ccc2nnc(NCc3ccc(OC(C)C)cc3)n2c1]

TABLE A-continued
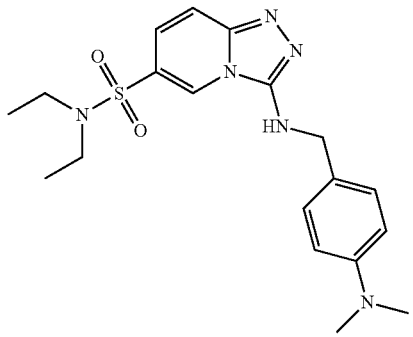 [SMILES: CCN(CC)S(=O)(=O)c1ccc2nnc(NCc3ccc(N(C)C)cc3)n2c1]
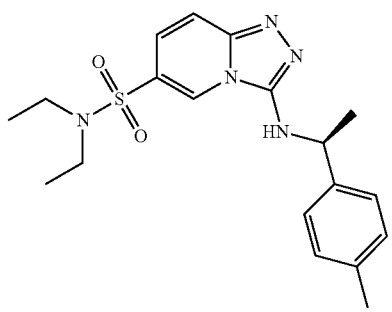 [SMILES: CCN(CC)S(=O)(=O)c1ccc2nnc(N[C@@H](C)c3ccc(C)cc3)n2c1]
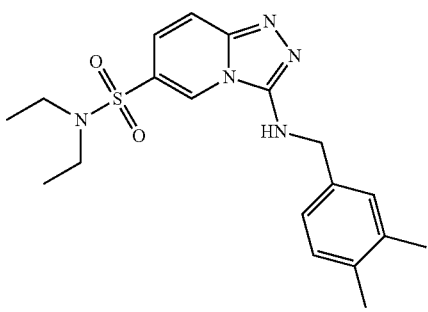 [SMILES: CCN(CC)S(=O)(=O)c1ccc2nnc(NCc3ccc(C)c(C)c3)n2c1]
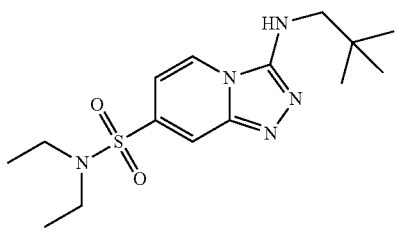 [SMILES: CCN(CC)S(=O)(=O)c1ccn2c(NCC(C)(C)C)nnc2c1]
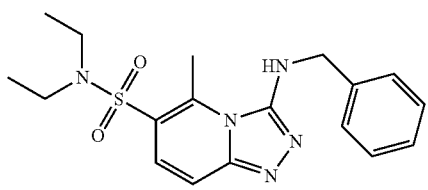 [SMILES: CCN(CC)S(=O)(=O)c1ccc2nnc(NCc3ccccc3)n2c1C]

TABLE A-continued
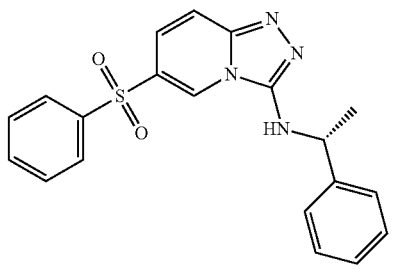 [SMILES: C[C@@H](Nc1nnc2ccc(S(=O)(=O)c3ccccc3)cn12)c1ccccc1]
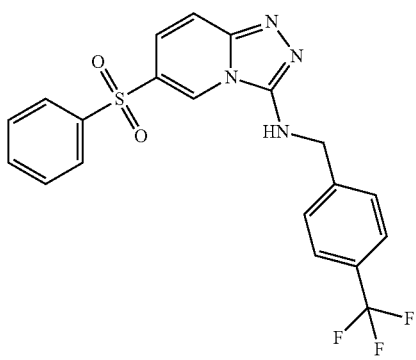 [SMILES: O=S(=O)(c1ccccc1)c1ccc2nnc(NCc3ccc(C(F)(F)F)cc3)n2c1]
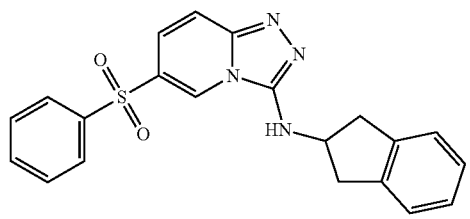
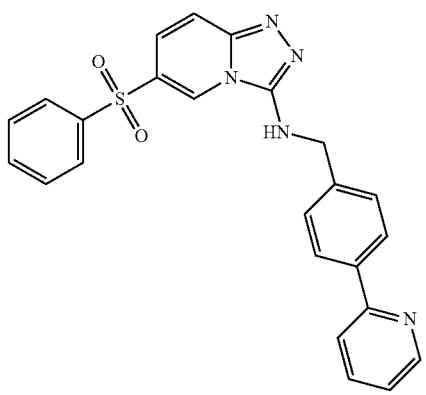 [SMILES: O=S(=O)(c1ccccc1)c1ccc2nnc(NCc3ccc(-c4ccccn4)cc3)n2c1]
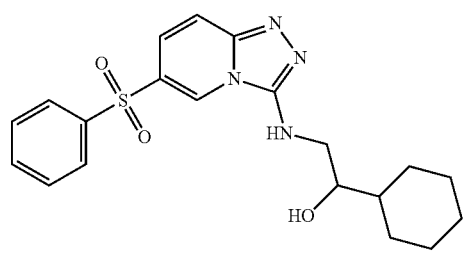 [SMILES: O=S(=O)(c1ccccc1)c1ccc2nnc(NCC(O)C3CCCCC3)n2c1]

TABLE A-continued
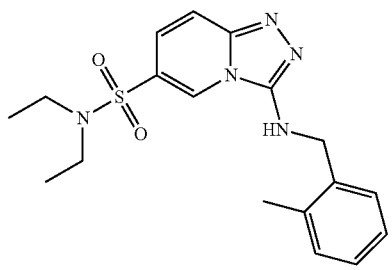 [SMILES: CCN(CC)S(=O)(=O)c1ccc2nnc(NCc3ccccc3C)n2c1]
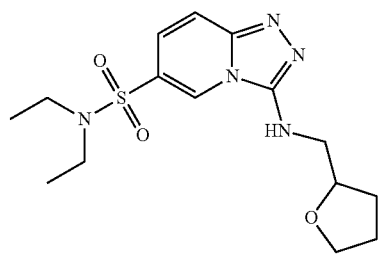 [SMILES: CCN(CC)S(=O)(=O)c1ccc2nnc(NCC3CCCO3)n2c1]
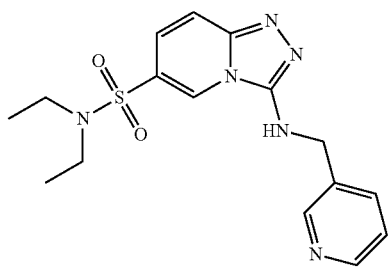 [SMILES: CCN(CC)S(=O)(=O)c1ccc2nnc(NCc3cccnc3)n2c1]
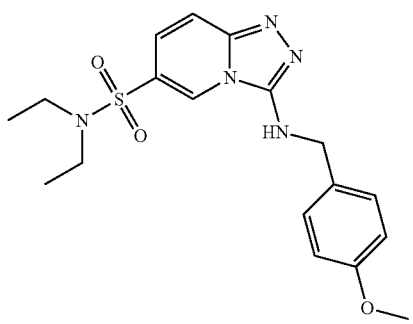 [SMILES: CCN(CC)S(=O)(=O)c1ccc2nnc(NCc3ccc(OC)cc3)n2c1]
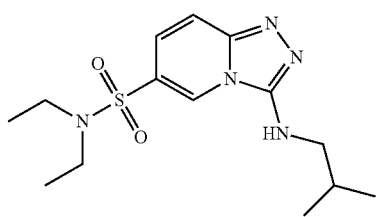 [SMILES: CCN(CC)S(=O)(=O)c1ccc2nnc(NCC(C)C)n2c1]
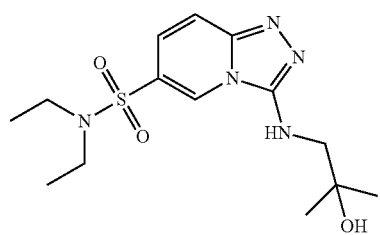 [SMILES: CCN(CC)S(=O)(=O)c1ccc2nnc(NCC(C)(C)O)n2c1]

TABLE A-continued
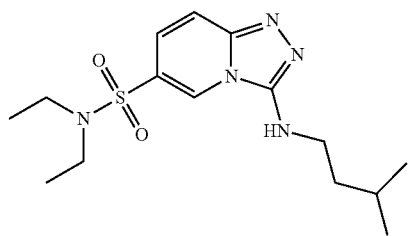 [SMILES: CCN(CC)S(=O)(=O)c1ccc2nnc(NCCC(C)C)n2c1]
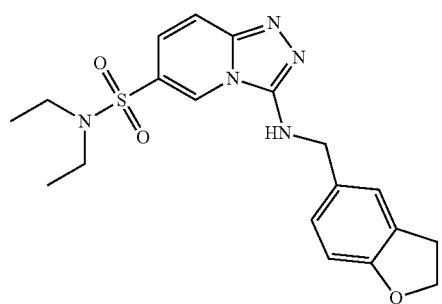 [SMILES: CCN(CC)S(=O)(=O)c1ccc2nnc(NCc3ccc4c(c3)CCO4)n2c1]
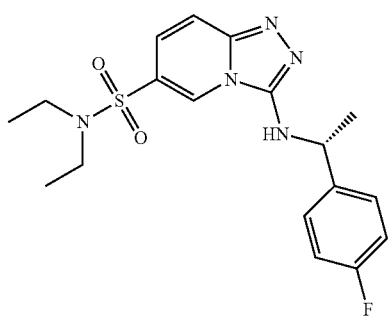 [SMILES: CCN(CC)S(=O)(=O)c1ccc2nnc(N[C@H](C)c3ccc(F)cc3)n2c1]
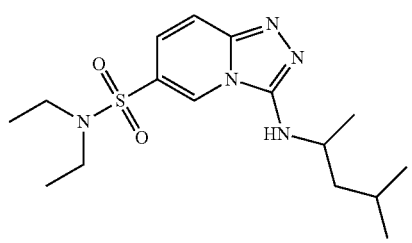 [SMILES: CCN(CC)S(=O)(=O)c1ccc2nnc(NC(C)CC(C)C)n2c1]
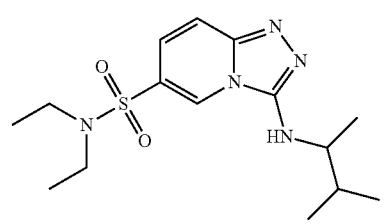 [SMILES: CCN(CC)S(=O)(=O)c1ccc2nnc(NC(C)C(C)C)n2c1]

TABLE A-continued
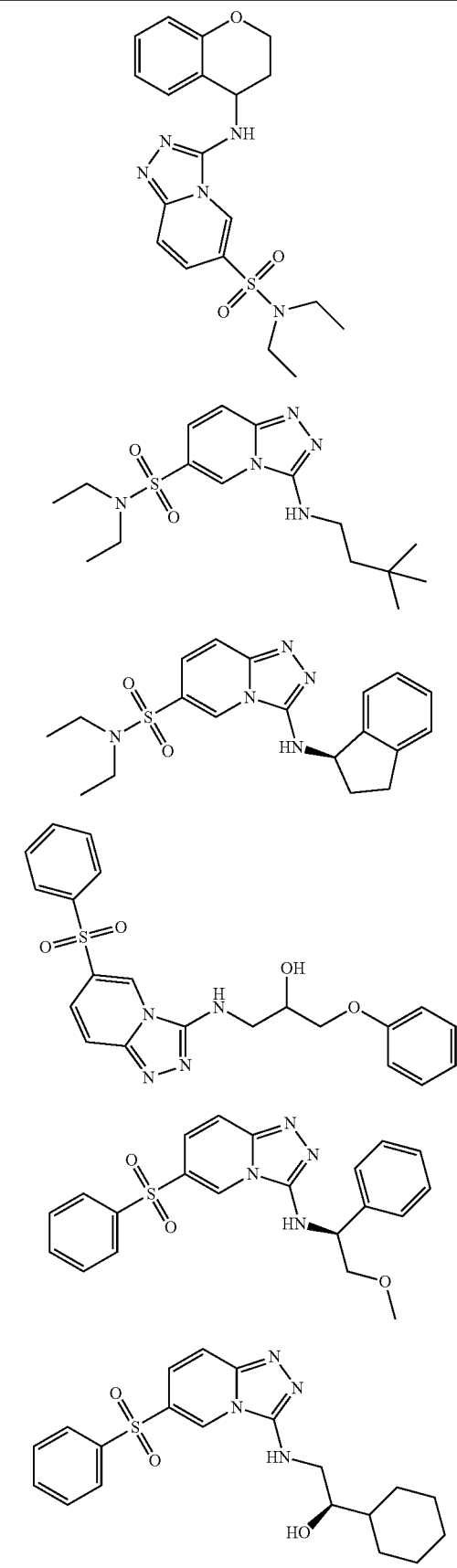

TABLE A-continued
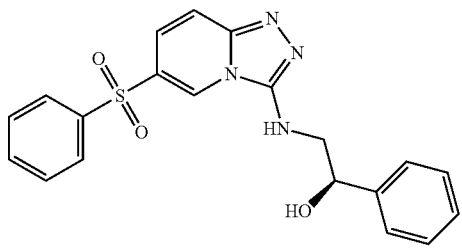 [SMILES: O=S(=O)(c1ccccc1)c1ccc2nnc(NC[C@H](O)c3ccccc3)n2c1]
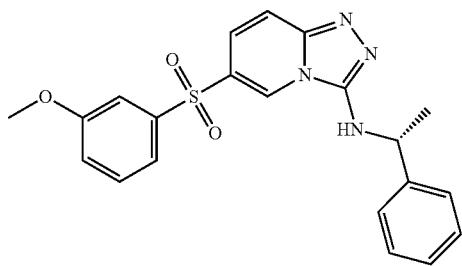 [SMILES: COc1cccc(S(=O)(=O)c2ccc3nnc(N[C@H](C)c4ccccc4)n3c2)c1]
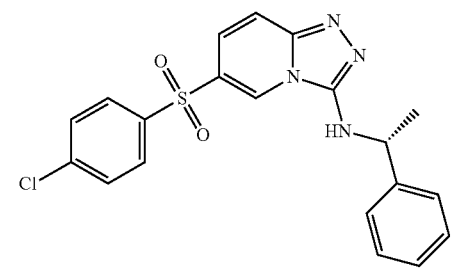 [SMILES: C[C@@H](Nc1nnc2ccc(S(=O)(=O)c3ccc(Cl)cc3)cn12)c1ccccc1]
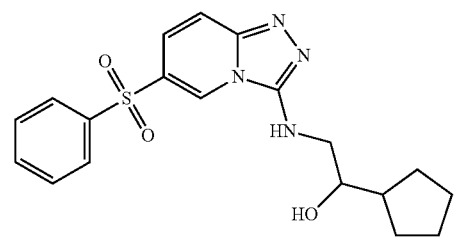 [SMILES: O=S(=O)(c1ccccc1)c1ccc2nnc(NCC(O)C3CCCC3)n2c1]
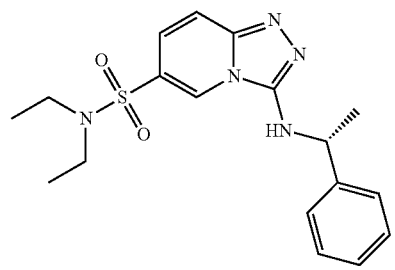 [SMILES: CCN(CC)S(=O)(=O)c1ccc2nnc(N[C@H](C)c3ccccc3)n2c1]
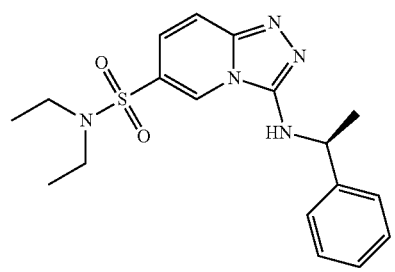 [SMILES: CCN(CC)S(=O)(=O)c1ccc2nnc(N[C@@H](C)c3ccccc3)n2c1]

TABLE A-continued
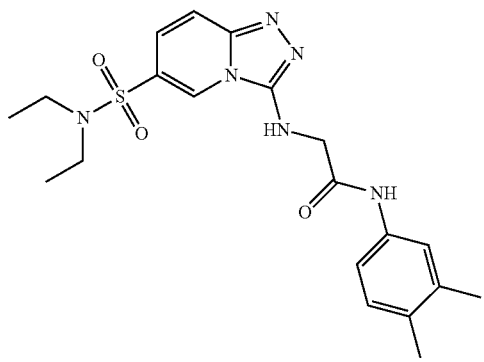 [SMILES: CCN(CC)S(=O)(=O)c1ccc2nnc(NCC(=O)Nc3ccc(C)c(C)c3)n2c1]
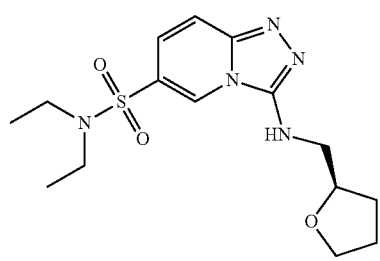 [SMILES: CCN(CC)S(=O)(=O)c1ccc2nnc(NC[C@H]3CCCO3)n2c1]
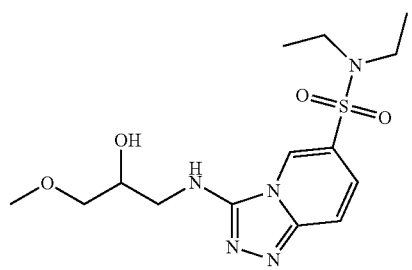 [SMILES: CCN(CC)S(=O)(=O)c1ccc2nnc(NCC(O)COC)n2c1]
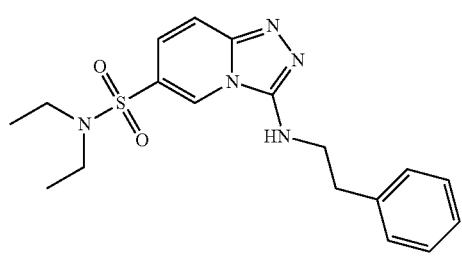 [SMILES: CCN(CC)S(=O)(=O)c1ccc2nnc(NCCc3ccccc3)n2c1]
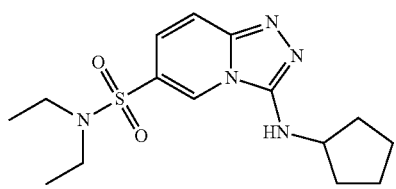 [SMILES: CCN(CC)S(=O)(=O)c1ccc2nnc(NC3CCCC3)n2c1]
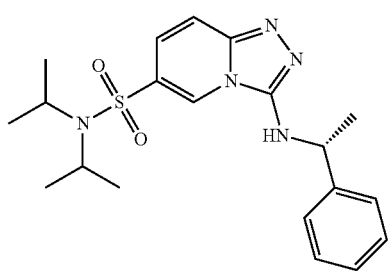 [SMILES: CC(C)N(C(C)C)S(=O)(=O)c1ccc2nnc(N[C@H](C)c3ccccc3)n2c1]

TABLE A-continued
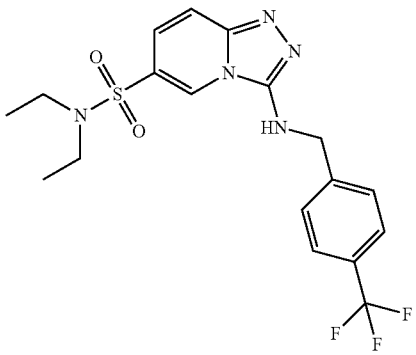 [SMILES: CCN(CC)S(=O)(=O)c1ccc2nnc(NCc3ccc(C(F)(F)F)cc3)n2c1]
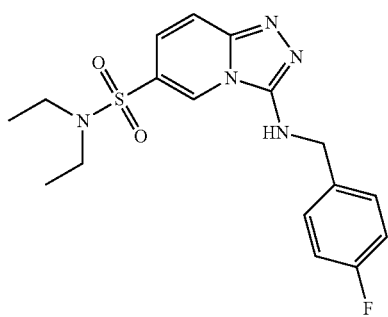 [SMILES: CCN(CC)S(=O)(=O)c1ccc2nnc(NCc3ccc(F)cc3)n2c1]
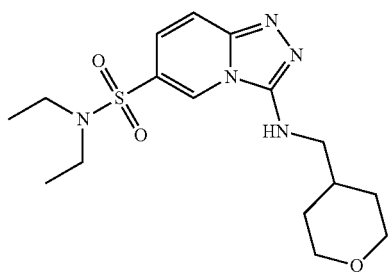
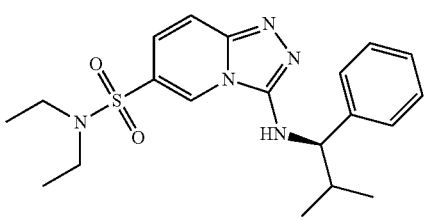 [SMILES: CCN(CC)S(=O)(=O)c1ccc2nnc(N[C@@H](c3ccccc3)C(C)C)n2c1]
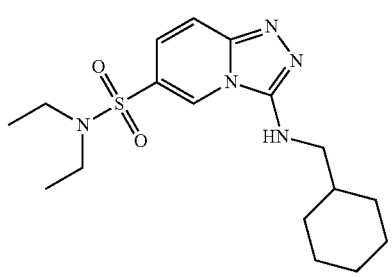 [SMILES: CCN(CC)S(=O)(=O)c1ccc2nnc(NCC3CCCCC3)n2c1]

TABLE A-continued
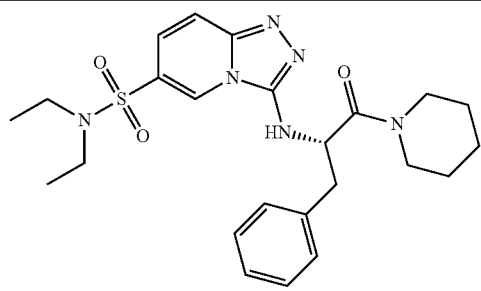
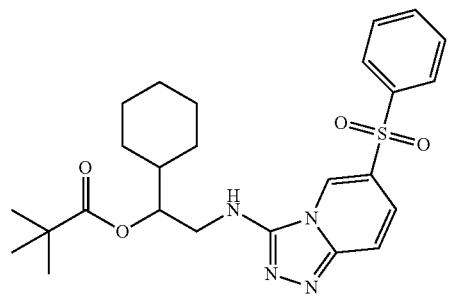 [SMILES: CC(C)(C)C(=O)OC(CNc1nnc2ccc(S(=O)(=O)c3ccccc3)cn12)C1CCCCC1]
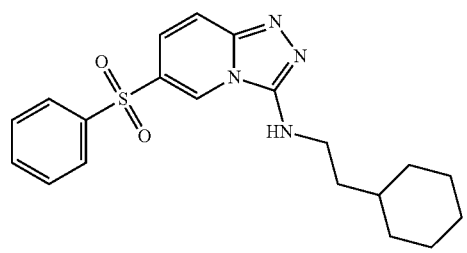 [SMILES: O=S(=O)(c1ccccc1)c1ccc2nnc(NCCC3CCCCC3)n2c1]
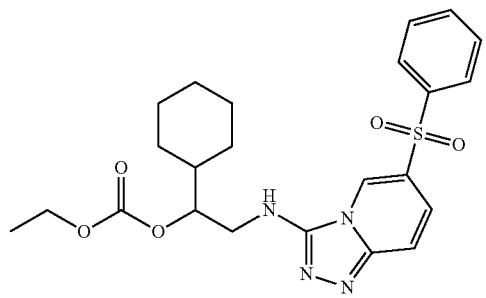 [SMILES: CCOC(=O)OC(CNc1nnc2ccc(S(=O)(=O)c3ccccc3)cn12)C1CCCCC1]
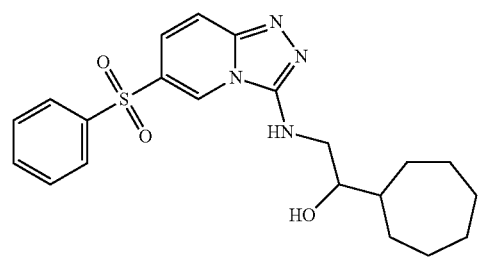 [SMILES: O=S(=O)(c1ccccc1)c1ccc2nnc(NCC(O)C3CCCCCC3)n2c1]
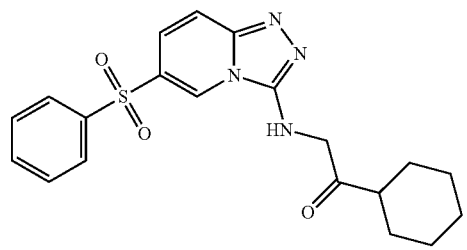 [SMILES: O=C(CNc1nnc2ccc(S(=O)(=O)c3ccccc3)cn12)C1CCCCC1]

TABLE A-continued
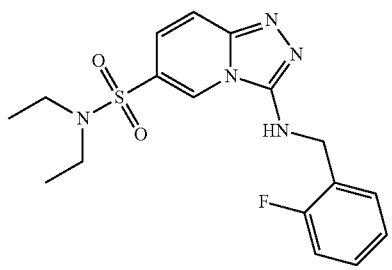
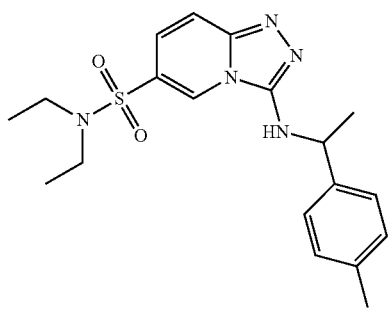 [SMILES: CCN(CC)S(=O)(=O)c1ccc2nnc(NC(C)c3ccc(C)cc3)n2c1]
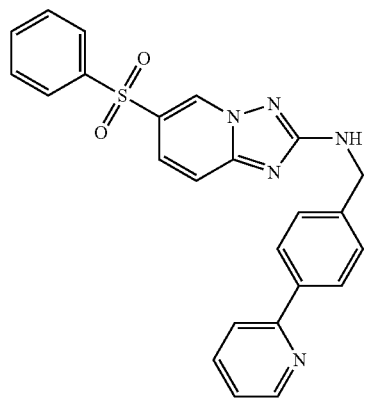 [SMILES: O=S(=O)(c1ccccc1)c1ccc2nc(NCc3ccc(-c4ccccn4)cc3)nn2c1]
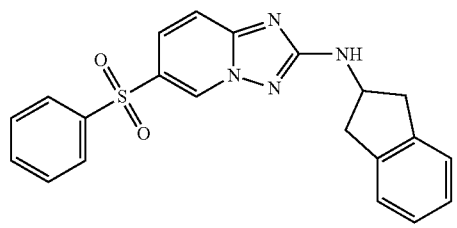 [SMILES: O=S(=O)(c1ccccc1)c1ccc2nc(NC3Cc4ccccc4C3)nn2c1]
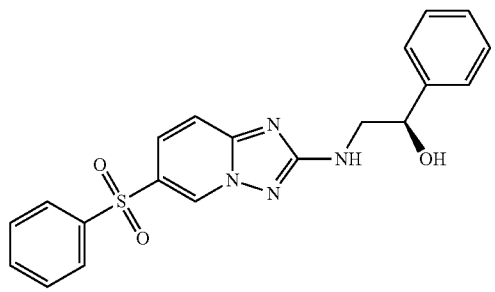 [SMILES: O=S(=O)(c1ccccc1)c1ccc2nc(NC[C@H](O)c3ccccc3)nn2c1]

TABLE A-continued
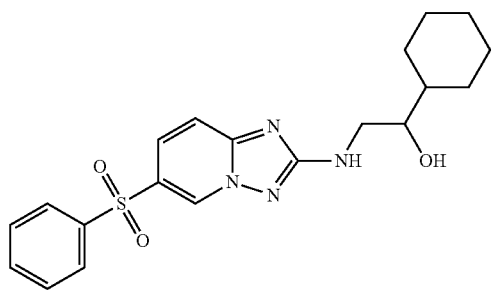 [SMILES: O=S(=O)(c1ccccc1)c1ccc2nc(NCC(O)C3CCCCC3)nn2c1]
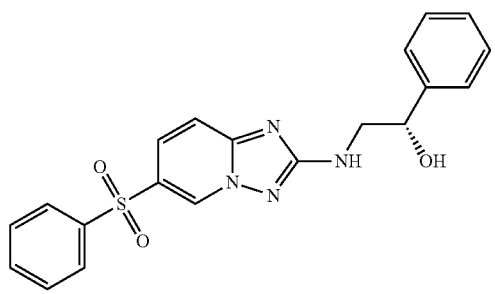 [SMILES: O=S(=O)(c1ccccc1)c1ccc2nc(NC[C@@H](O)c3ccccc3)nn2c1]
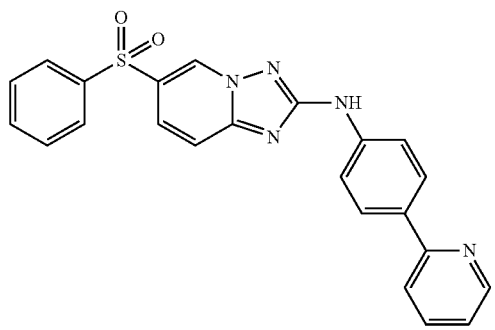 [SMILES: O=S(=O)(c1ccccc1)c1ccc2nc(Nc3ccc(-c4ccccn4)cc3)nn2c1]
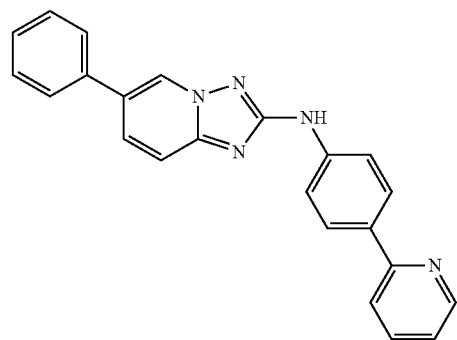 [SMILES: c1ccc(-c2ccc3nc(Nc4ccc(-c5ccccn5)cc4)nn3c2)cc1]
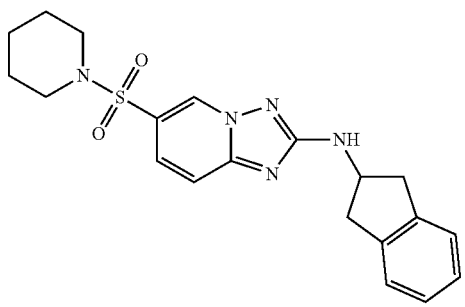 [SMILES: O=S(=O)(c1ccc2nc(NC3Cc4ccccc4C3)nn2c1)N1CCCCC1]

TABLE A-continued
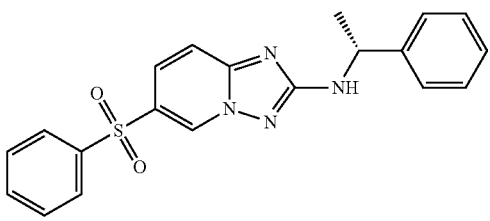 [SMILES: C[C@@H](Nc1nc2ccc(S(=O)(=O)c3ccccc3)cn2n1)c1ccccc1]
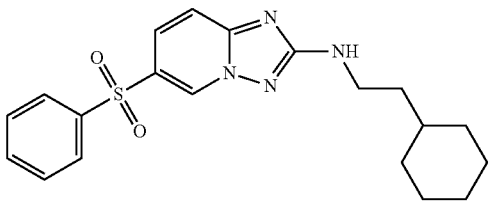 [SMILES: O=S(=O)(c1ccccc1)c1ccc2nc(NCCC3CCCCC3)nn2c1]
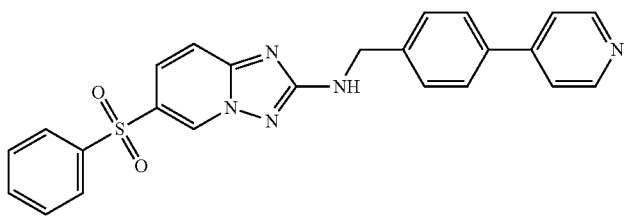 [SMILES: O=S(=O)(c1ccccc1)c1ccc2nc(NCc3ccc(-c4ccncc4)cc3)nn2c1]
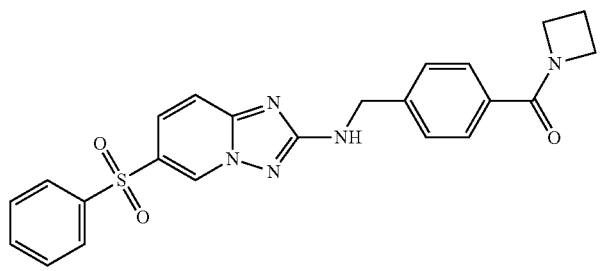 [SMILES: O=C(c1ccc(CNc2nc3ccc(S(=O)(=O)c4ccccc4)cn3n2)cc1)N1CCC1]
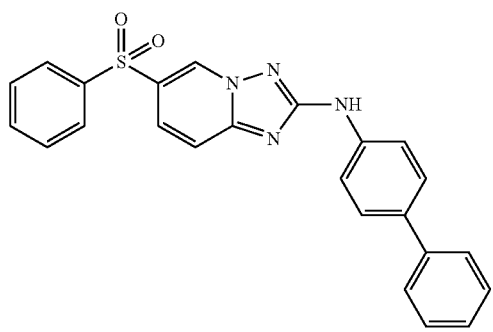

TABLE A-continued
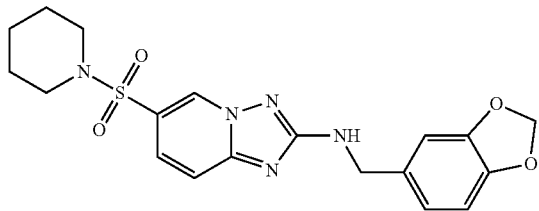 [SMILES: O=S(=O)(c1ccc2nc(NCc3ccc4c(c3)OCO4)nn2c1)N1CCCCC1]
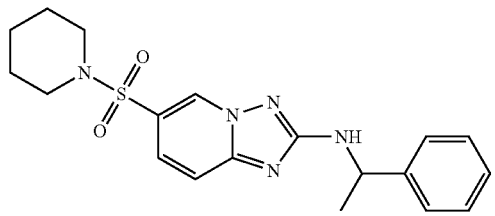 [SMILES: CC(Nc1nc2ccc(S(=O)(=O)N3CCCCC3)cn2n1)c1ccccc1]
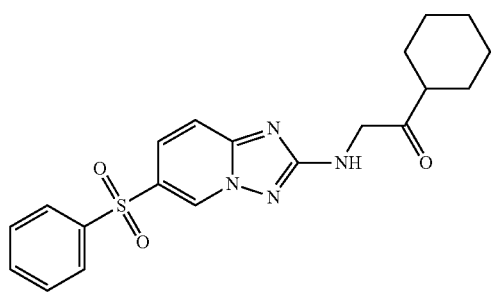 [SMILES: O=C(CNc1nc2ccc(S(=O)(=O)c3ccccc3)cn2n1)C1CCCCC1]
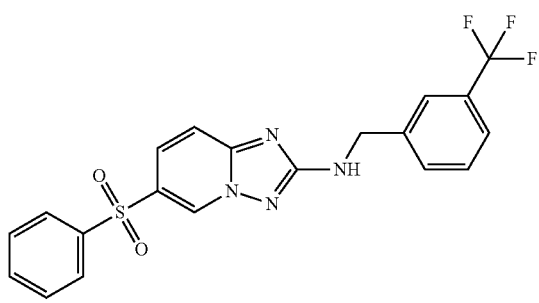 [SMILES: O=S(=O)(c1ccccc1)c1ccc2nc(NCc3cccc(C(F)(F)F)c3)nn2c1]
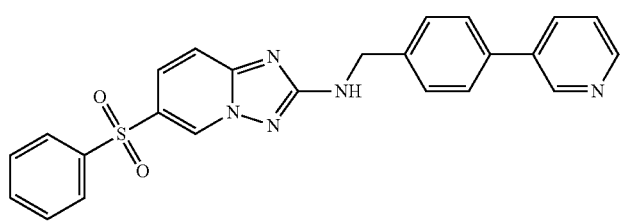 [SMILES: O=S(=O)(c1ccccc1)c1ccc2nc(NCc3ccc(-c4cccnc4)cc3)nn2c1]
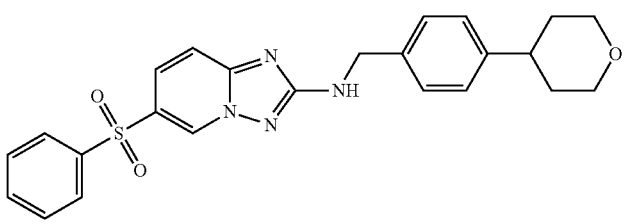 [SMILES: O=S(=O)(c1ccccc1)c1ccc2nc(NCc3ccc(C4CCOCC4)cc3)nn2c1]

TABLE A-continued
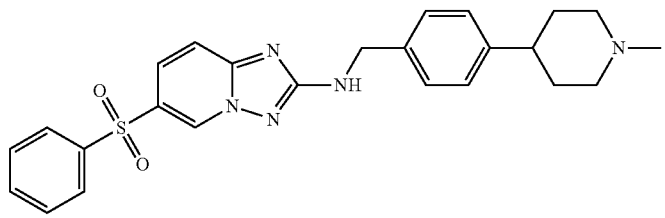 [SMILES: CN1CCC(c2ccc(CNc3nc4ccc(S(=O)(=O)c5ccccc5)cn4n3)cc2)CC1]
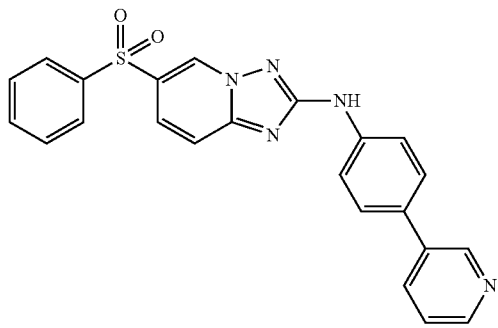 [SMILES: O=S(=O)(c1ccccc1)c1ccc2nc(Nc3ccc(-c4cccnc4)cc3)nn2c1]
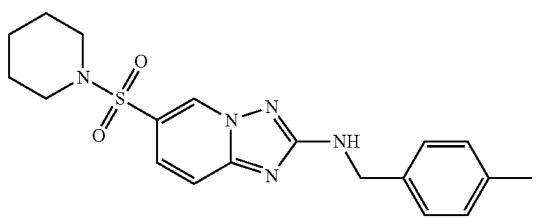 [SMILES: Cc1ccc(CNc2nc3ccc(S(=O)(=O)N4CCCCC4)cn3n2)cc1]
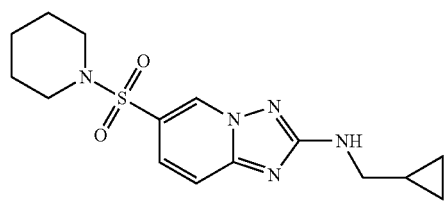 [SMILES: O=S(=O)(c1ccc2nc(NCC3CC3)nn2c1)N1CCCCC1]
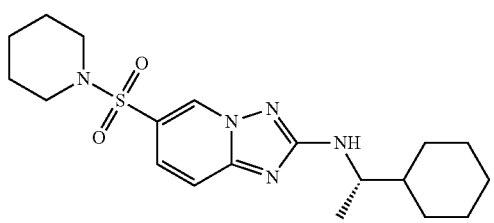 [SMILES: C[C@H](Nc1nc2ccc(S(=O)(=O)N3CCCCC3)cn2n1)C1CCCCC1]
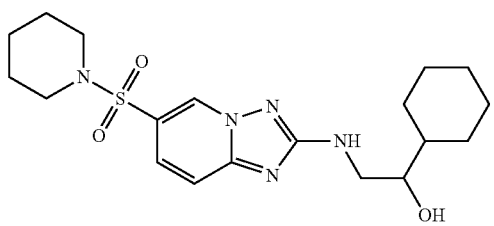 [SMILES: O=S(=O)(c1ccc2nc(NCC(O)C3CCCCC3)nn2c1)N1CCCCC1]
LIST OF ABBREVIATIONS
All temperatures are in degrees Centigrade
CF—cystic fibrosis
CFTR—cystic fibrosis transmembrane conductance regulator
DIPEA—N,N-diisopropylethylamine
DMF—dimethylformamide
DMSO—dimethylsulfoxide
ENaC—epithelial sodium channel
$Et_2O$—diethyl ether
$Et_3N$—triethylamine
EtOAc—ethyl acetate
h—hours H₂O—water
HATU—(1-[Bis(dimethylamino)methylene]-1H-1,2,3-triazolo[4,5-b]pyridinium 3-oxid hexafluorophosphate)
HBS—Hepes-buffered saline
HCl—hydrochloric acid
HOAc—acetic acid
HPLC—high pressure liquid chromatography
hr—hours
HTS—high throughput screen
MDC—methylenedichloride
Na₂SO₄—sodium sulfate
NaH—sodium hydride
NaHCO₃—sodium bicarbonate
NAUC—normalized area under the curve
NH₄Cl—ammonium chloride
NMR—nuclear magnetic resonance
PBS—Phosphate buffered saline
POCl3—phosphorus oxychloride
rt—room temperature
TEA—triethylamine
TFA—trifluoroacetic acid
Tetrakis—triphenylphosphine)palladium(0)
THF—tetrahydrofuran
YFP—yellow fluorescent protein The compounds of this invention may be prepared by methods known in the art. Exemplary synthetic routes to prepare compounds of this invention are illustrated below:

Scheme I:

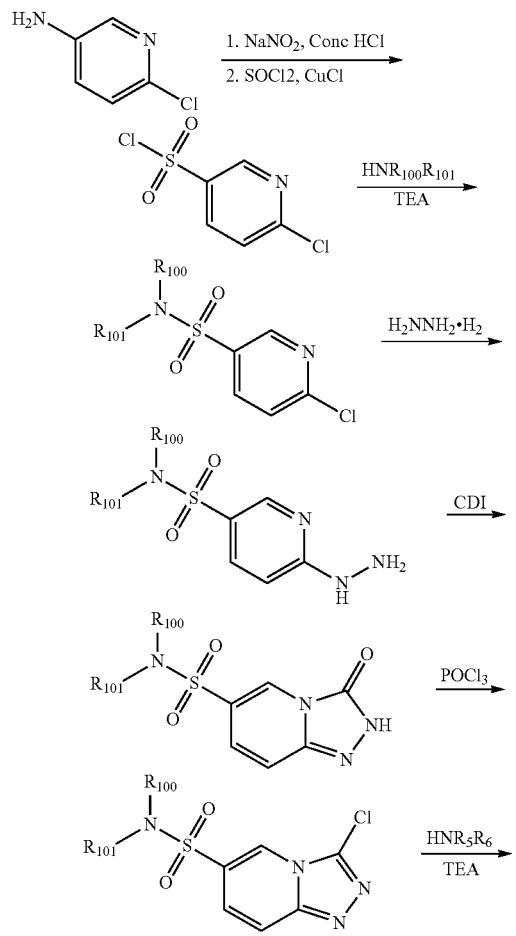

-continued

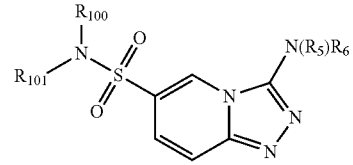

Scheme II:

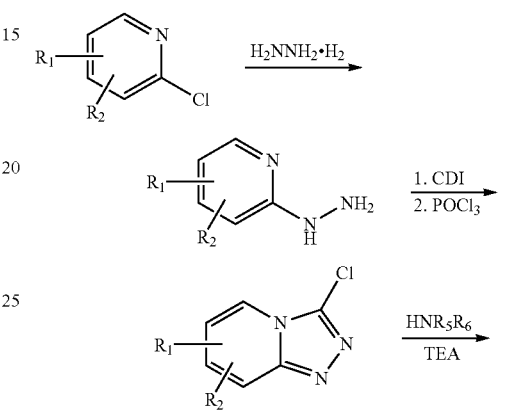

Scheme III:

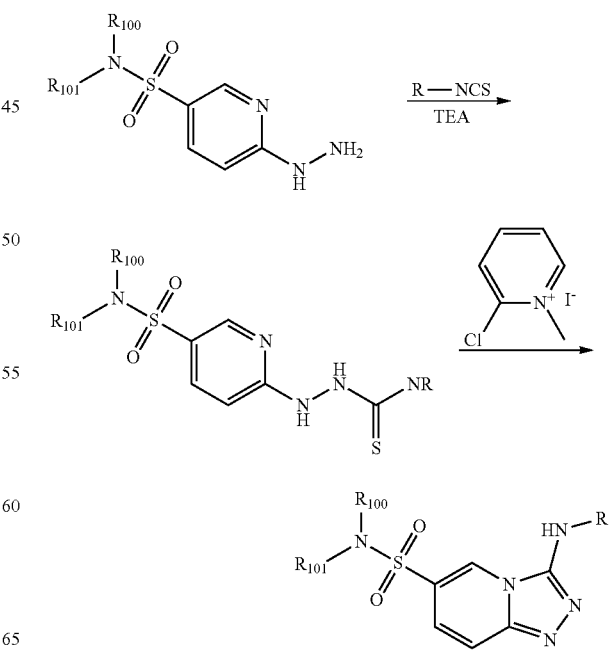

Scheme IV:

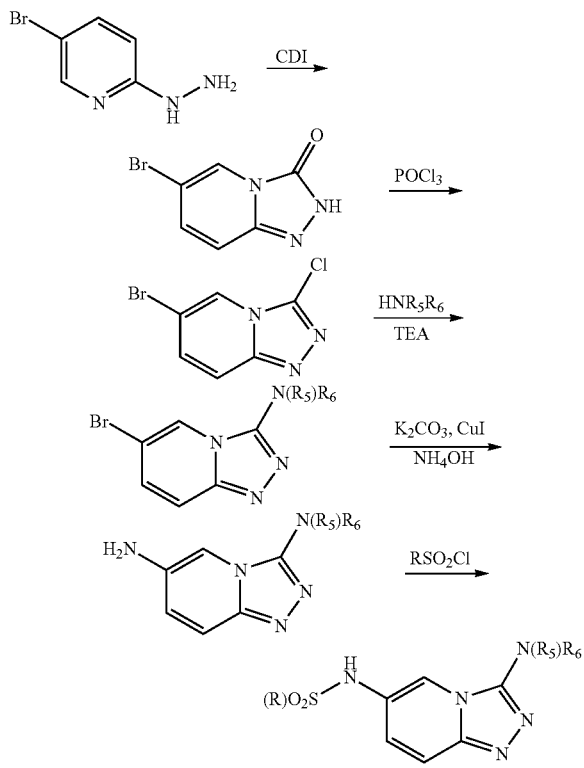

Scheme V:

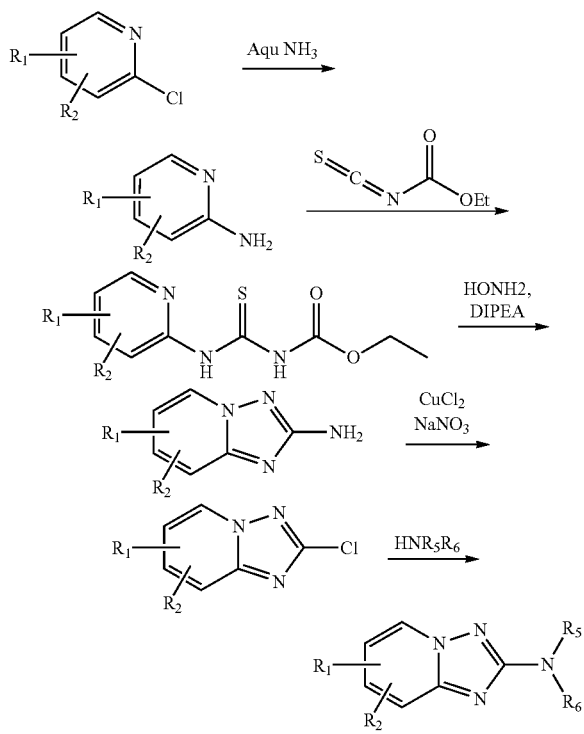

Compounds of the invention are useful as modulators of CFTR and treating diseases or disorders mediated by CFTR such as for the treatment of disease, disorders or conditions such as Cystic fibrosis, constipation, asthma, pancreatitis, gastrointestinal disorders, infertility, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia. ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type 1, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta- (β) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1, 3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1, 3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

The compositions described herein can be formulated in a unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration. In one embodiment, the unit dosage form can have one of the compounds of the invention as an active ingredient in an amount of about 10 mg, 20 mg, 30 mg, 40 mg, 50 mg, 100 mg, 150 mg, 200 mg, 250 mg, 300 mg, 400 mg, 500 mg, 600 mg, 700 mg, 750 mg, 800 mg, 900 mg, 1000 mg, or 1,250 mg.

In some embodiments, the compounds of the invention can be administered in a dose of at least about 10 mg/day to at least about 1500 mg/day. In some embodiments, the compounds of the invention are administered in a dose of at least about 300 mg (e.g., at least about 450 mg, at least about 500 mg, at least about 750 mg, at least about 1,000 mg, at least about 1250 mg, or at least about 1500 mg).

Dose adjustments can be made for patients with mild, moderate or severe hepatic impairment (Child-Pugh Class A). Furthermore, dosage adjustments can be made for patients taking one or more Cytochrome P450 inhibitors and inducers, in particular CYP3A4, CYP2D6, CYP2C9, CYP2C19 and CYP2B6 inhibitors and inducers. Dose adjustments can also be made for patients with impaired Cytochrome P450 function such as poor, intermediate, extensive and ultra-rapid metabolizers.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1, 2, 4-triazolyl, 1H-1, 2, 3-triazolyl, 2H-1, 2, 3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1, 5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1, 2, 4-oxadiazolyl, 1, 3, 4-oxadiazolyl, 1, 2, 5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1, 2, 4-thiadiazolyl, 1, 3, 4-thiadiazolyl, 1, 2, 5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms.

More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N, N-alkylamino, such as N-methylamino, N-ethylamino, N, N-dimethylamino, N, N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

The present invention includes all pharmaceutically acceptable isotopically-labeled or enriched compounds of the invention. The compounds include one or more atoms that are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, nitrogen, such as $^{13}N$ and $^{15}N$, oxygen, such as $^{15}O$, $^{17}O$ and $^{18}O$, chlorine, such as $^{36}Cl$, fluorine, such as $^{18}F$, iodine, $^{123}I$ and $^{125}I$, phosphorus, such as $^{32}P$, and sulphur, such as $^{35}S$.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

6-Chloropyridine-3-sulfonyl chloride

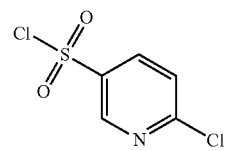 [SMILES: O=S(=O)(Cl)c1ccc(Cl)nc1]

Thionyl chloride (60 mL, 823 mmol) was added to water (360 mL) at 0° C. over 60 min so that the temperature was maintained between 0 and 7° C. After stirring the mixture for 17 hrs at 15° C., CuCl (0.218 g, 1.9 mmol) was added and the resulting solution cooled to 0° C. In a separate flask, a solution of 6-chloro-3-amino pyridine (25 g, 195 mmol) in con HCl (195 mL) was cooled to −5° C. and treated dropwise with a solution of sodium nitrite (14.4 g, 208 mmol) in water (58 mL) while the temperature was maintained between −5 and 0° C. When the addition was complete, this solution was then added to the precooled solution of thionyl chloride in water at 0° C. and stirred for 1 hr. The solid was collected by filtration, washed with water, and dried to yield 6-chloropyridine-3-sulfonyl chloride (26.0 g); $^1H$ NMR (DMSO) δ: 7.48-7.50 (d, J=9.2 Hz, 1H), 7.96-7.98 (m, 1H), 8.55-8.56 (d, J=3.2 Hz, 1H).

6-Chloro-N,N-diethylpyridine-3-sulfonamide

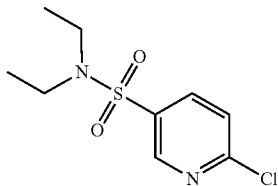

6-Chloropyridine-3-sulfonyl chloride (3.0 g, 14 mmol) was added to a 0° C. solution of diethylamine (1.24 g, 16.9 mmol) and triethyl amine (5.23 mL, 42.3 mmol) in DCM (20 mL). After stirring at rt for 16 hrs, the reaction was diluted with water (50 mL) and extracted with DCM (2×25 mL). The combined organic layers were washed with brine (50 mL), dried with $Na_2SO_4$, and concentrated to yield 6-chloro-N,N-diethylpyridine-3-sulfonamide (3.0 g); (ESI +ve, 249.1 [M+H]); $^1$H NMR (DMSO) δ: 1.05-1.08 (t, 6H), 3.19-3.24 (q, 4H), 7.77 (d J=8.4 Hz, 1H), 8.25-8.28 (q, 1H), 8.83 (d, J=2.4 Hz 1H).

N,N-Diethyl-6-hydrazinylpyridine-3-sulfonamide

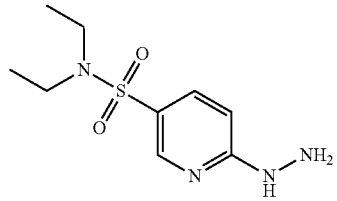 [SMILES: CCN(CC)S(=O)(=O)c1ccc(NN)nc1]

6-chloro-N,N-diethylpyridine-3-sulfonamide (3.0 g, 12 mmol) was dissolved in EtOH (30 mL) and treated with hydrazine hydrate (2.44 g, 48 mmol). The reaction was heated to reflux for 16 hr, then cooled to rt and the EtOH removed in vacuo. The solid was triturated with $Et_2O$ to yield N,N-diethyl-6-hydrazinylpyridine-3-sulfonamide (2.7 g); (ESI +ve, 245.1 [M+H]); $^1$H NMR (DMSO) δ: 1.02-1.05 (t, 6H), 3.07-3.12 (q, 4H), 5.03 (s, 2H), 6.77 (d, J=8 Hz, 1H), 7.70-7.73 (q, 1H), 8.29 (d, J=2 Hz, 1H), 8.46 (s, 1H).

N,N-Diethyl-3-oxo-2,3-dihydro-[1,2,4]triazolo[4,3-a]pyridine-6-sulfonamide

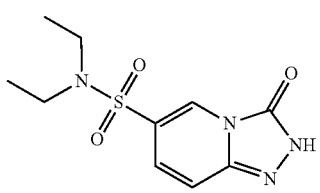 [SMILES: CCN(CC)S(=O)(=O)c1ccc2n[nH]c(=O)n2c1]

N, N-diethyl-6-hydrazinylpyridine-3-sulfonamide (2.0 g, 8.18 mmol) was dissolved in THF (20 mL), treated with CDI (1.99 g, 1.22 mmol), and heated to reflux for 16 hrs. The reaction was diluted with water (100 mL) and then extracted with EtOAc (2×200 mL). The combined organics were washed with water (2×200 mL), dried with $Na_2SO_4$, and concentrated to yield N,N-diethyl-3-oxo-2,3-dihydro-[1,2,4]triazolo[4,3-a]pyridine-6-sulfonamide (1.8 g); (ESI +ve, 249.11 [M+H]); $^1$H NMR (DMSO) δ: 1.23-1.25 (t, 6H), 3.16-3.25 (q, 4H), 7.30-7.36 (m, 2H), 8.07-8.07 (t, 1H), 12.79 (s, 1H).

3-Chloro-N,N-diethyl-[1,2,4]triazolo[4,3-a]pyridine-6-sulfonamide

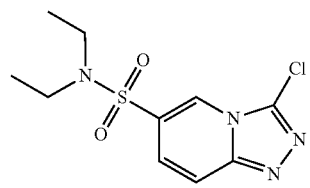 [SMILES: CCN(CC)S(=O)(=O)c1ccc2nnc(Cl)n2c1]

N,N-diethyl-3-oxo-2,3-dihydro-[1,2,4]triazolo[4,3-a]pyridine-6-sulfonamide (0.20 g, 0.73 mmol) and $POCl_3$ (6 mL) was heated to 110° C. for 16 hrs. The reaction was cooled, poured onto crushed ice, and neutralized with sat'd $NaHCO_3$ solution. The mixture was extracted with EtOAc (2×15 mL), and the combined organics were washed with brine (10 mL), dried with $Na_2SO_4$, and concentrated to yield 3-chloro-N,N-diethyl-[1,2,4]triazolo[4,3-a]pyridine-6-sulfonamide (0.16 g); (ESI +ve, 289.14 [M+H]); $^1$H NMR (DMSO) δ: 1.09-1.12 (t, 6H), 3.26-3.31 (q, 4H), 7.66-7.68 (q, 1H), 7.98-8.00 (m, 1H), 8.57-8.58 (m, 1H).

Example 1: 3-(Benzylamino)-N,N-diethyl-[1,2,4]triazolo[4,3-a]pyridine-6-sulfonamide

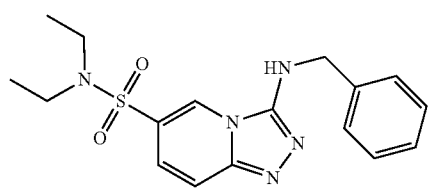 [SMILES: CCN(CC)S(=O)(=O)c1ccc2nnc(NCc3ccccc3)n2c1]

3-chloro-N,N-diethyl-[1,2,4]triazolo[4,3-a]pyridine-6-sulfonamide (0.15 g, 0.52 mmol) and $BnNH_2$ (1 mL) were heated to 140° C. overnight. The reaction was diluted with water (20 mL) and extracted with EtOAc (2×15 mL). The combined organic layers were washed with brine (10 mL), dried with $Na_2SO_4$, and concentrated to yield 3-(benzylamino)-N,N-diethyl-[1,2,4]triazolo[4,3-a]pyridine-6-sulfonamide (0.05 g, 27%); (ESI +ve, 361.23 [M+H]); $^1$H NMR (DMSO) δ: 1.02-1.05 (t, 6H), 3.15-3.20 (q, 4H), 4.46-4.47 (d, J=6 2H), 7.19-7.28 (q, 1H), 7.30-7.35 (m, 4H), 7.49-7.56 (m, 2H), 7.70-7.73 (t, 1H), 8.96 (s, 1H).

Representative compounds of the invention were prepared in a similar manner to example 1 (scheme 1) using the appropriate amines.

| No. | Structure | LCMS m/z |
|---|---|---|
| 2 | 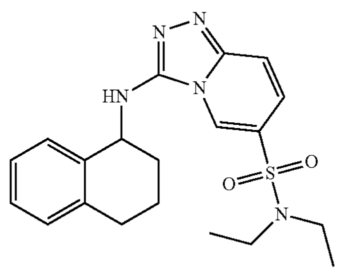 [SMILES: CCN(CC)S(=O)(=O)c1ccc2nnc(NC3CCCc4ccccc43)n2c1] | 400.5 |
| 3 | 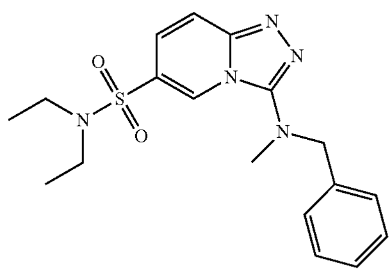 [SMILES: CCN(CC)S(=O)(=O)c1ccc2nnc(N(C)Cc3ccccc3)n2c1] | 374.5 |
| 4 | 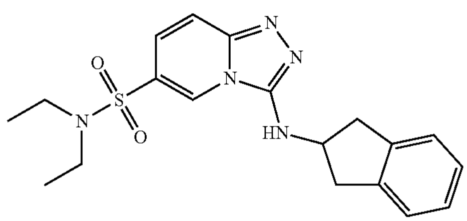 [SMILES: CCN(CC)S(=O)(=O)c1ccc2nnc(NC3Cc4ccccc4C3)n2c1] | 386.5 |
| 5 | 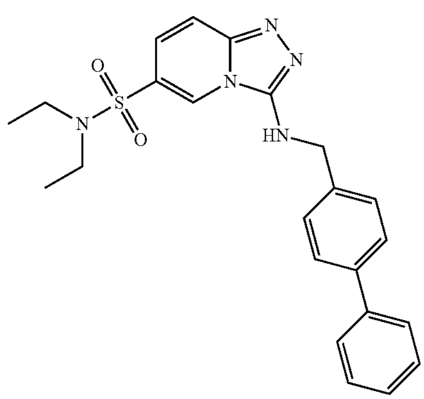 [SMILES: CCN(CC)S(=O)(=O)c1ccc2nnc(NCc3ccc(-c4ccccc4)cc3)n2c1] | 436.5 |
| 6 | 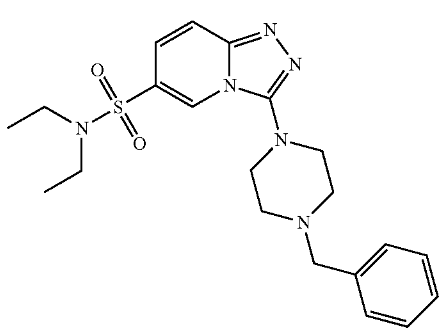 [SMILES: CCN(CC)S(=O)(=O)c1ccc2nnc(N3CCN(Cc4ccccc4)CC3)n2c1] | 429.6 |

-continued
| No. | Structure | LCMS m/z |
|---|---|---|
| 7 | 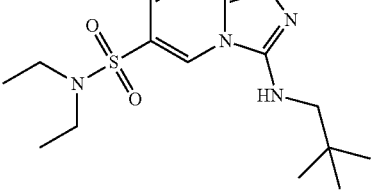 | 340.5 |
| 8 | 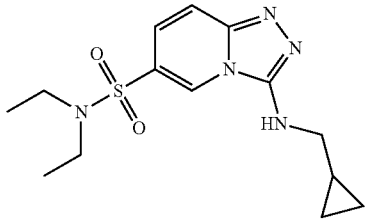 [SMILES: CCN(CC)S(=O)(=O)c1ccc2nnc(NCC3CC3)n2c1] | 324.4 |
| 9 | 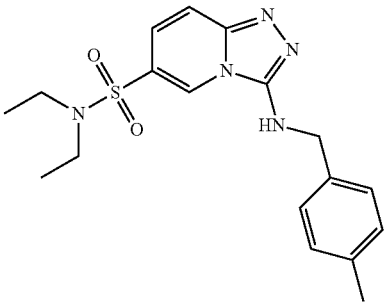 [SMILES: CCN(CC)S(=O)(=O)c1ccc2nnc(NCc3ccc(C)cc3)n2c1] | 374.5 |
| 10 | 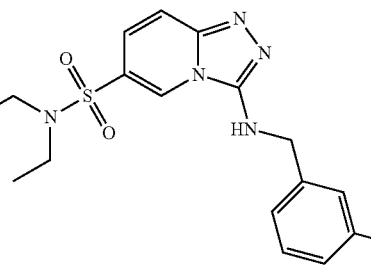 | 374.5 |
| 11 | 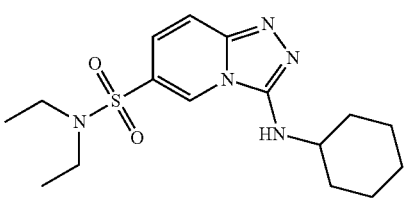 [SMILES: CCN(CC)S(=O)(=O)c1ccc2nnc(NC3CCCCC3)n2c1] | 352.5 |
| 12 | 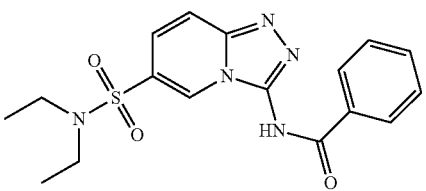 [SMILES: CCN(CC)S(=O)(=O)c1ccc2nnc(NC(=O)c3ccccc3)n2c1] | 374.4 |

| No. | Structure | LCMS m/z |
|---|---|---|
| 13 | 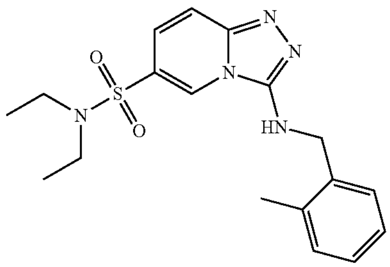 [SMILES: CCN(CC)S(=O)(=O)c1ccc2nnc(NCc3ccccc3C)n2c1] | 374.5 |
| 14 | 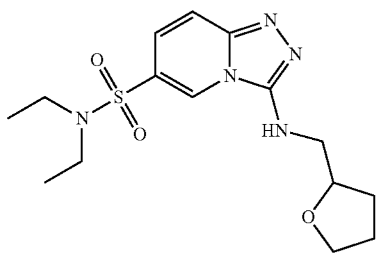 [SMILES: CCN(CC)S(=O)(=O)c1ccc2nnc(NCC3CCCO3)n2c1] | 354.4 |
| 15 | 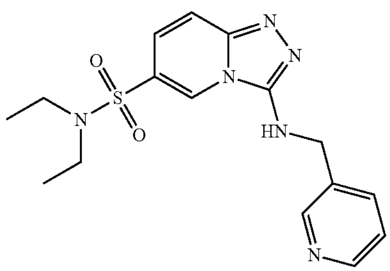 [SMILES: CCN(CC)S(=O)(=O)c1ccc2nnc(NCc3cccnc3)n2c1] | 361.4 |
| 16 | 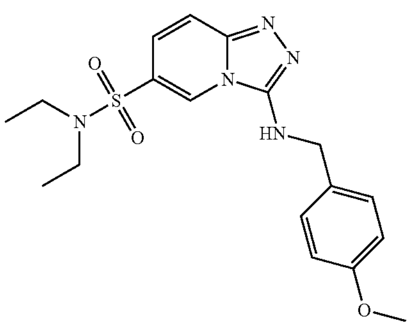 [SMILES: CCN(CC)S(=O)(=O)c1ccc2nnc(NCc3ccc(OC)cc3)n2c1] | 390.5 |
| 17 | 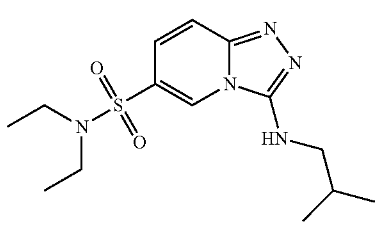 [SMILES: CCN(CC)S(=O)(=O)c1ccc2nnc(NCC(C)C)n2c1] | 326.4 |
| 18 | 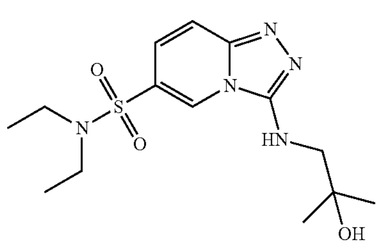 [SMILES: CCN(CC)S(=O)(=O)c1ccc2nnc(NCC(C)(C)O)n2c1] | 342.4 |

-continued

| No. | Structure | LCMS m/z |
|---|---|---|
| 19 | 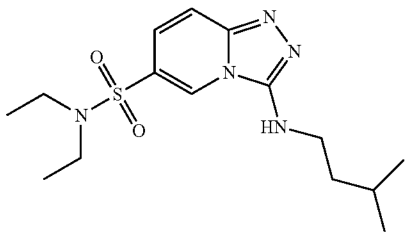 [SMILES: CCN(CC)S(=O)(=O)c1ccc2nnc(NCCC(C)C)n2c1] | 340.5 |
| 20 | 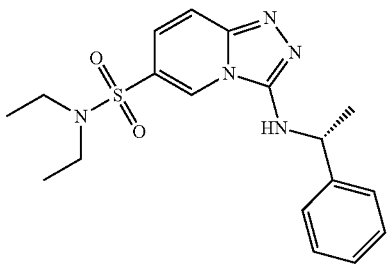 [SMILES: CCN(CC)S(=O)(=O)c1ccc2nnc(N[C@H](C)c3ccccc3)n2c1] | 374.5 |
| 21 | 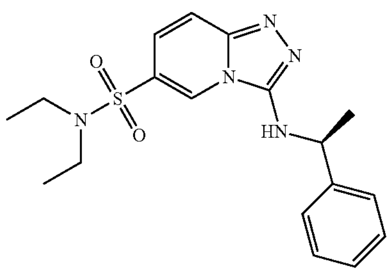 [SMILES: CCN(CC)S(=O)(=O)c1ccc2nnc(N[C@@H](C)c3ccccc3)n2c1] | 374.5 |
| 22 | 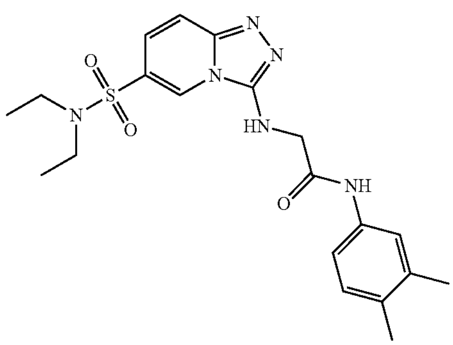 [SMILES: CCN(CC)S(=O)(=O)c1ccc2nnc(NCC(=O)Nc3ccc(C)c(C)c3)n2c1] | 431.5 |
| 23 | 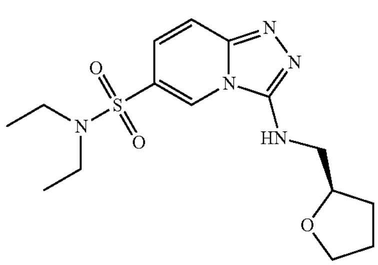 [SMILES: CCN(CC)S(=O)(=O)c1ccc2nnc(NC[C@H]3CCCO3)n2c1] | 354.4 |

-continued

| No. | Structure | LCMS m/z |
|---|---|---|
| 24 | 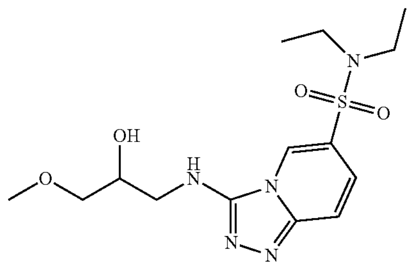 [SMILES: CCN(CC)S(=O)(=O)c1ccc2nnc(NCC(O)COC)n2c1] | 358.4 |
| 25 | 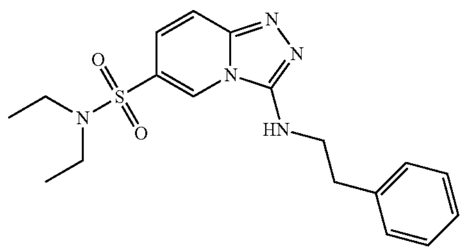 [SMILES: CCN(CC)S(=O)(=O)c1ccc2nnc(NCCc3ccccc3)n2c1] | 374.5 |
| 26 | 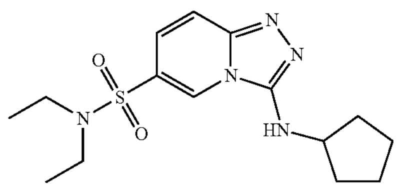 [SMILES: CCN(CC)S(=O)(=O)c1ccc2nnc(NC3CCCC3)n2c1] | 338.4 |
| 27 | 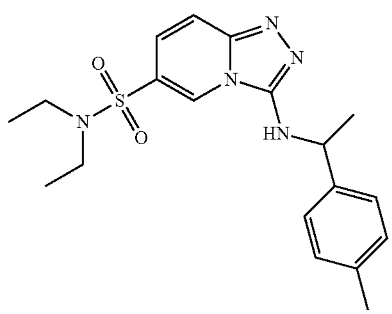 [SMILES: CCN(CC)S(=O)(=O)c1ccc2nnc(NC(C)c3ccc(C)cc3)n2c1] | 388.5 |
| 28 | 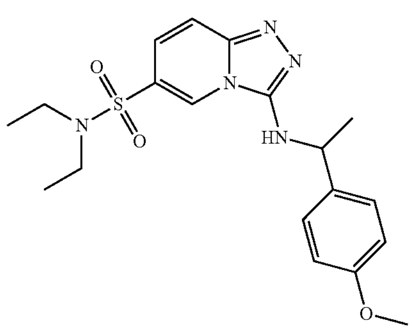 [SMILES: CCN(CC)S(=O)(=O)c1ccc2nnc(NC(C)c3ccc(OC)cc3)n2c1] | 404.5 |
| 29 | 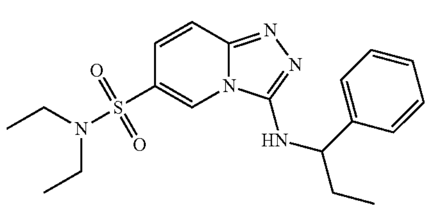 [SMILES: CCC(Nc1nnc2ccc(S(=O)(=O)N(CC)CC)cn12)c1ccccc1] | 388.5 |

-continued

| No. | Structure | LCMS m/z |
|---|---|---|
| 30 | 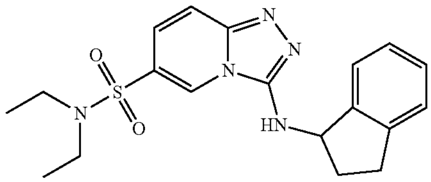 [SMILES: CCN(CC)S(=O)(=O)c1ccc2nnc(NC3CCc4ccccc43)n2c1] | 386.5 |
| 31 | 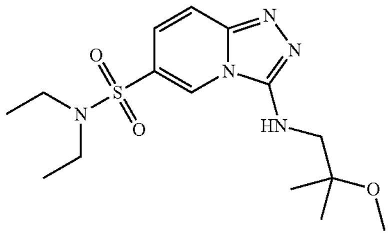 [SMILES: CCN(CC)S(=O)(=O)c1ccc2nnc(NCC(C)(C)OC)n2c1] | 356.5 |
| 32 | 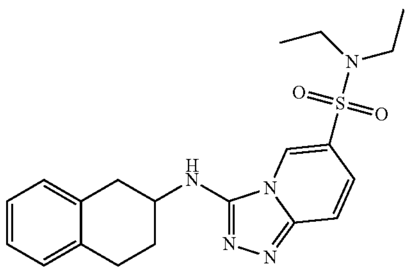 [SMILES: CCN(CC)S(=O)(=O)c1ccc2nnc(NC3CCc4ccccc4C3)n2c1] | 400.5 |
| 33 | 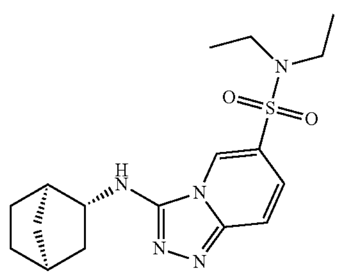 [SMILES: CCN(CC)S(=O)(=O)c1ccc2nnc(N[C@@H]3C[C@H]4CC[C@@H]3C4)n2c1] | 364.5 |
| 34 | 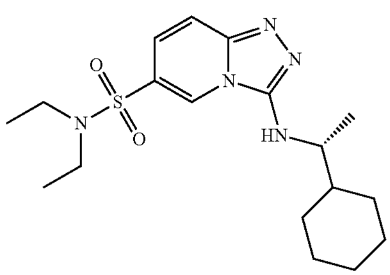 [SMILES: CCN(CC)S(=O)(=O)c1ccc2nnc(N[C@H](C)C3CCCCC3)n2c1] | 380.5 |
| 35 | 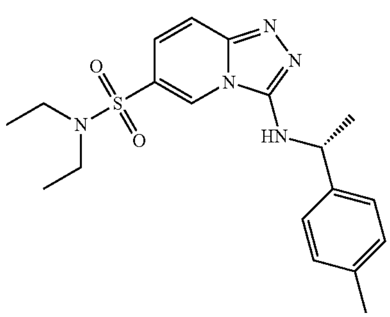 [SMILES: CCN(CC)S(=O)(=O)c1ccc2nnc(N[C@H](C)c3ccc(C)cc3)n2c1] | 388.5 |

-continued

| No. | Structure | LCMS m/z |
|---|---|---|
| 36 | 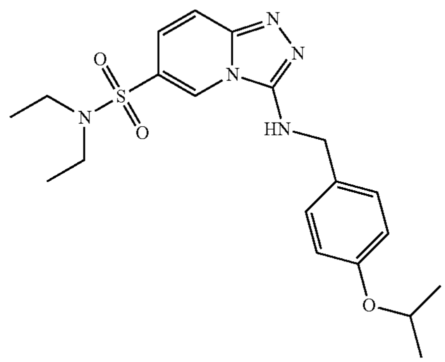 [SMILES: CCN(CC)S(=O)(=O)c1ccc2nnc(NCc3ccc(OC(C)C)cc3)n2c1] | 418.5 |
| 37 | 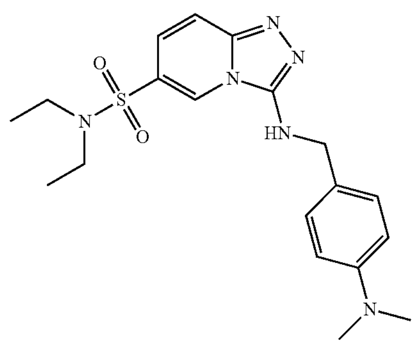 [SMILES: CCN(CC)S(=O)(=O)c1ccc2nnc(NCc3ccc(N(C)C)cc3)n2c1] | 403.5 |
| 38 | 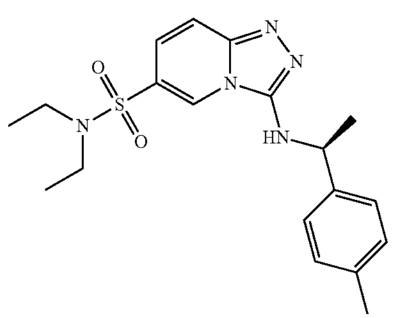 [SMILES: CCN(CC)S(=O)(=O)c1ccc2nnc(N[C@@H](C)c3ccc(C)cc3)n2c1] | 388.5 |
| 39 | 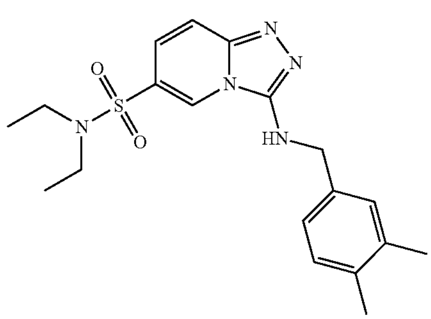 [SMILES: CCN(CC)S(=O)(=O)c1ccc2nnc(NCc3ccc(C)c(C)c3)n2c1] | 388.5 |

-continued

| No. | Structure | LCMS m/z |
|---|---|---|
| 40 | 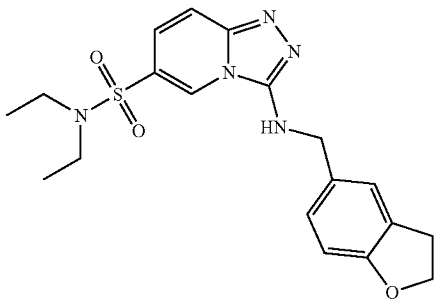 [SMILES: CCN(CC)S(=O)(=O)c1ccc2nnc(NCc3ccc4c(c3)CCO4)n2c1] | 402.5 |
| 41 | 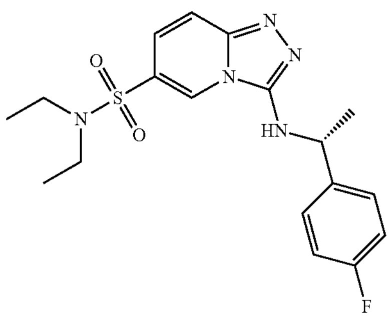 [SMILES: CCN(CC)S(=O)(=O)c1ccc2nnc(N[C@H](C)c3ccc(F)cc3)n2c1] | 392.5 |
| 42 | 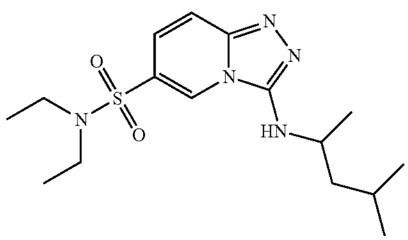 [SMILES: CCN(CC)S(=O)(=O)c1ccc2nnc(NC(C)CC(C)C)n2c1] | 354.5 |
| 43 | 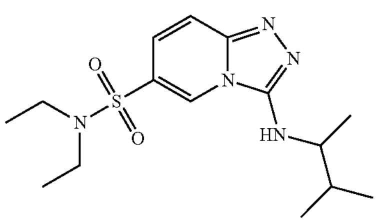 [SMILES: CCN(CC)S(=O)(=O)c1ccc2nnc(NC(C)C(C)C)n2c1] | 340.5 |
| 44 | 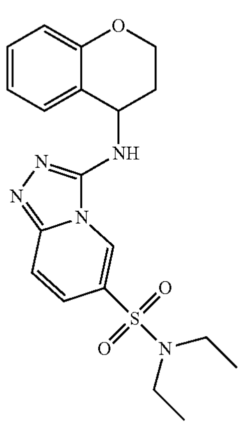 [SMILES: CCN(CC)S(=O)(=O)c1ccc2nnc(NC3CCOc4ccccc43)n2c1] | 402.5 |

-continued

| No. | Structure | LCMS m/z |
|---|---|---|
| 45 | 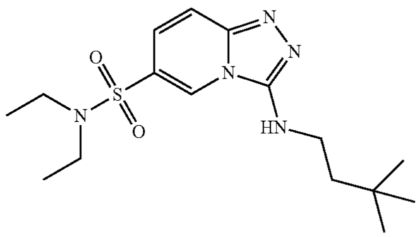 [SMILES: CCN(CC)S(=O)(=O)c1ccc2nnc(NCCC(C)(C)C)n2c1] | 354.5 |
| 46 | 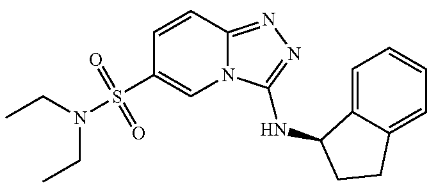 [SMILES: CCN(CC)S(=O)(=O)c1ccc2nnc(N[C@@H]3CCc4ccccc43)n2c1] | 386.5 |
| 47 | 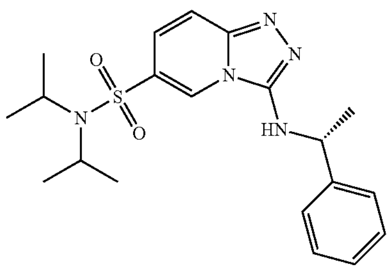 [SMILES: CC(C)N(C(C)C)S(=O)(=O)c1ccc2nnc(N[C@H](C)c3ccccc3)n2c1] | 402.5 |
| 48 | 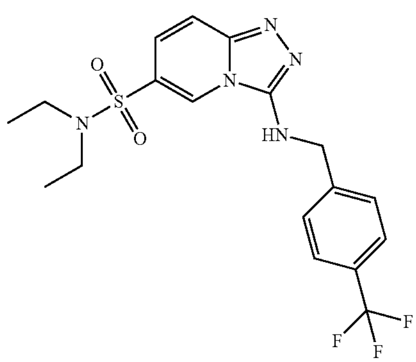 [SMILES: CCN(CC)S(=O)(=O)c1ccc2nnc(NCc3ccc(C(F)(F)F)cc3)n2c1] | 428.4 |
| 49 | 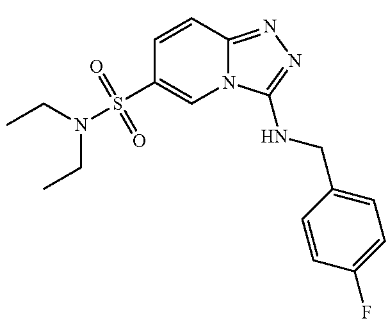 [SMILES: CCN(CC)S(=O)(=O)c1ccc2nnc(NCc3ccc(F)cc3)n2c1] | 378.4 |

| No. | Structure | LCMS m/z |
|---|---|---|
| 50 | 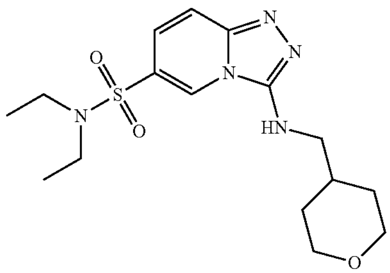 [SMILES: CCN(CC)S(=O)(=O)c1ccc2nnc(NCC3CCOCC3)n2c1] | 368.5 |
| 51 | 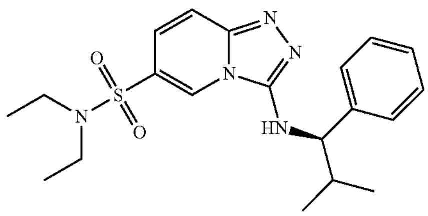 [SMILES: CCN(CC)S(=O)(=O)c1ccc2nnc(N[C@@H](c3ccccc3)C(C)C)n2c1] | 402.5 |
| 52 | 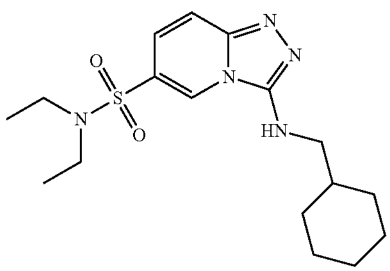 [SMILES: CCN(CC)S(=O)(=O)c1ccc2nnc(NCC3CCCCC3)n2c1] | 366.5 |
| 53 | 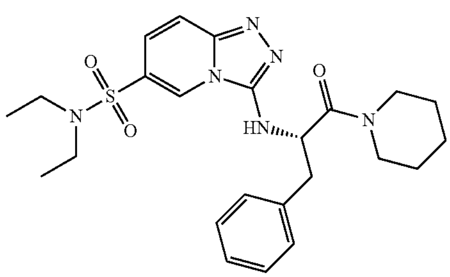 [SMILES: CCN(CC)S(=O)(=O)c1ccc2nnc(N[C@@H](Cc3ccccc3)C(=O)N3CCCCC3)n2c1] | 485.6 |
| 54 | 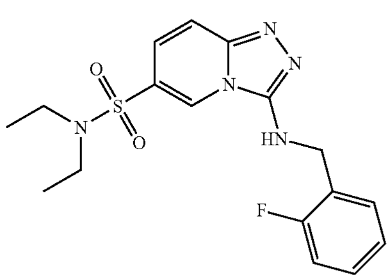 | 378.4 |

| No. | Structure | LCMS m/z |
|---|---|---|
| 55 | 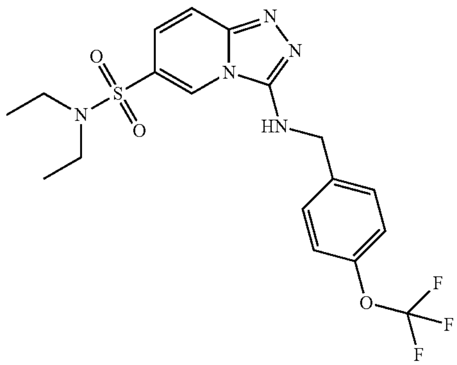 [SMILES: CCN(CC)S(=O)(=O)c1ccc2nnc(NCc3ccc(OC(F)(F)F)cc3)n2c1] | 444.4 |
| 56 | 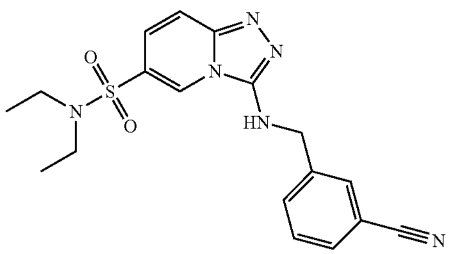 [SMILES: CCN(CC)S(=O)(=O)c1ccc2nnc(NCc3cccc(C#N)c3)n2c1] | 385.5 |
| 57 | 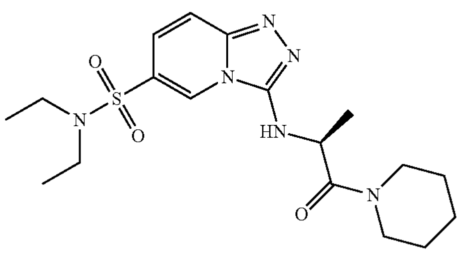 [SMILES: CCN(CC)S(=O)(=O)c1ccc2nnc(N[C@@H](C)C(=O)N3CCCCC3)n2c1] | 409.5 |

N-Ethylpyridin-3-amine

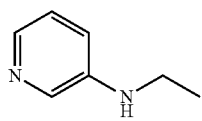

3-Aminopyridine (2.0 g, 21.2 mmol), acetonitrile (4.36 g, 106 mmol), and 10% Pd/C (0.2 g) in MeOH (20 mL) were stirred at 25° C. under H₂ atmosphere for 16 hrs. The reaction was filtered through Celite and the filtrated concentrated. The crude product was purified by column chromatography (silica gel, 5-10% MeOH/DCM) to yield N-ethylpyridin-3-amine (0.7 g).

6-Chloro-N-ethyl-N-(pyridin-3-yl)pyridine-3-sulfonamide

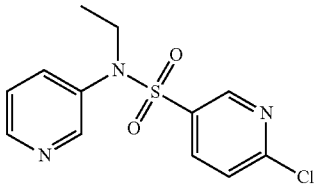 [SMILES: CCN(c1cccnc1)S(=O)(=O)c1ccc(Cl)nc1]

6-Chloropyridine-3-sulfonyl chloride (1.0 g, 4.7 mmol) was added to a 0° C. solution of N-ethylpyridin-3-amine (0.7 g, 5.66 mmol) and triethylamine (1.95 mL, 14 mmol) in DCM (30 mL). After stirring at rt for 16 hrs, the reaction was diluted with water (15 mL) and extracted with DCM (2×15 mL). The combined organic layers were washed with brine (15 mL), dried with Na₂SO₄, and concentrated to yield 6-chloro-N-ethyl-N-(pyridin-3-yl)pyridine-3-sulfonamide (1.0 g).

N-Ethyl-6-hydrazinyl-N-(pyridin-3-yl)pyridine-3-sulfonamide

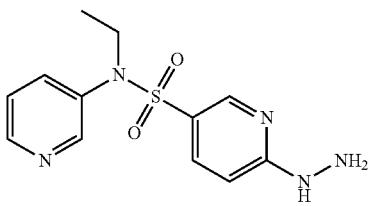 [SMILES: CCN(c1cccnc1)S(=O)(=O)c1ccc(NN)nc1]

6-Chloro-N-ethyl-N-(pyridin-3-yl)pyridine-3-sulfonamide (0.3 g, 1.0 mmol) was dissolved in EtOH (5 mL) and treated with hydrazine hydrate (0.2 mL, 4.0 mmol). The reaction was heated to 80° C. for 16 hr, then cooled to rt and the EtOH removed in vacuo. The solid was triturated with Et$_2$O to yield N-ethyl-6-hydrazinyl-N-(pyridin-3-yl)pyridine-3-sulfonamide (0.3 g).

(R)-2-(5-(N-Ethyl-N-(pyridin-3-yl)sulfamoyl)pyridin-2-yl)-N-(1-phenylethyl)hydrazine-1-carbothioamide

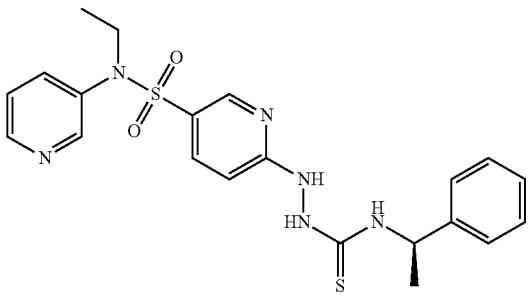 [SMILES: CCN(c1cccnc1)S(=O)(=O)c1ccc(NNC(=S)N[C@H](C)c2ccccc2)nc1]

N-Ethyl-6-hydrazinyl-N-(pyridin-3-yl)pyridine-3-sulfonamide (0.3 g, 1.0 mmol) was dissolved in THF (15 mL), then treated with triethylamine (0.35 mL, 2.55 mmol) and (R)-(1-isothiocyanatoethyl)benzene (0.250 g, 1.53 mmol). After stirring at rt for 16 hrs, the reaction was diluted with water (40 mL) and extracted with EtOAc (2×40 mL). The combined organic layers were dried with Na$_2$SO$_4$, and concentrated. The crude product was purified by chromatography (silica gel, 5-10% MeOH/DCM) to yield to yield (R)-2-(5-(N-ethyl-N-(pyridin-3-yl)sulfamoyl)pyridin-2-yl)-N-(1-phenylethyl)hydrazine-1-carbothioamide (0.34 g).

Example 58: (R)—N-Ethyl-3-((1-phenylethyl)amino)-N-(pyridin-3-yl)-[1,2,4]triazolo[4,3-a]pyridine-6-sulfonamide

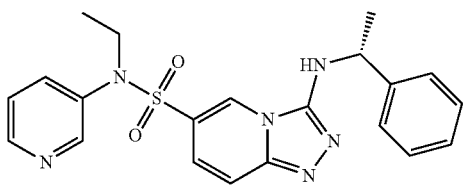 [SMILES: CCN(c1cccnc1)S(=O)(=O)c1ccc2nnc(N[C@H](C)c3ccccc3)n2c1]

(R)-2-(5-(N-Ethyl-N-(pyridin-3-yl)sulfamoyl)pyridin-2-yl)-N-(1-phenylethyl)hydrazine-1-carbothioamide (0.34 g, 0.74 mmol) was dissolved in THF (5 mL), and treated with triethylamine (0.24 mL, 1.78 mmol) and 2-chloro-1-methyl pyridinium iodide (0.22 g, 0.89 mmol). After stirring at rt for 30 min, the reaction was diluted with water (40 mL) and extracted in EtOAc (2×40 mL). The combined organic layers were dried with Na$_2$SO$_4$, and concentrated. The crude product was purified by chromatography (silica gel, 5-10% MeOH/DCM) to yield (R)—N-ethyl-3-((1-phenylethyl)amino)-N-(pyridin-3-yl)-[1,2,4]triazolo[4,3-a]pyridine-6-sulfonamide (0.035 g, 11%); MS: ESI +ve 422.95 [M+H]; $^1$H NMR: (400 MHz, DMSO-d$_6$) δ: 0.99 (t, 3H), 1.5 (d, J=6, 3H), 3.69 (q, 2H), 4.9 (t, 1H), 6.9 (dd, J=9 and 1, 1H), 7.2 (t, 1H), 7.3 (t, 2H), 7.4 (m, 3H), 7.5 (d, J=8, 1H), 7.5 (d, J=7, 1H), 7.6 (d, J=8, 1H), 8.4 (d, J=2, 1H), 8.5 (dd, J=4 and 1, 1H), 8.8 (s, 1H).

6-Bromo-[1, 2, 4] triazolo [4, 3-a] pyridin-3(2H)-one

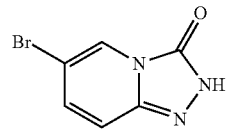

5-Bromo-2-hydrazinylpyridine (2.00 g, 10.6 mmol) in THF (20 mL) was treated with CDI (2.59 g, 15.9 mmol) at rt and then stirred at reflux overnight. The reaction was diluted with water (50 mL) and extracted in EtOAc (2×50 mL). The combined organic layers were washed with brine (50 mL), dried with Na$_2$SO$_4$, and concentrated to give 6-bromo-[1, 2, 4] triazolo [4, 3-a] pyridin-3(2H)-one (1.50 g, 67%); ESI +ve 213.85 [M+1].

6-Bromo-3-chloro-[1,2,4]triazolo[4,3-a]pyridine

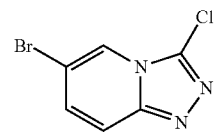

6-Bromo-[1,2,4]triazolo[4,3-a]pyridin-3(2H)-one (1.50 g, 7.0 mmol) in POCl$_3$ (15 mL) was heated to 110° C. overnight. The reaction was cooled, poured onto crushed ice, and neutralized with sat'd NaHCO$_3$ (250 mL). The mixture was extracted with EtOAc (2×100 mL), and the combined organics were washed with brine (50 mL), dried with Na$_2$SO$_4$, and concentrated to yield 6-bromo-3-chloro-[1,2,4]triazolo[4,3-a]pyridine (1.11 g, 68%); ESI +ve 234.10 [M+1].

N-Benzyl-6-bromo-[1,2,4]triazolo[4,3-a]pyridin-3-amine

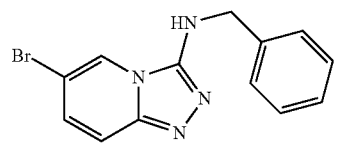 [SMILES: Brc1ccc2nnc(NCc3ccccc3)n2c1]

6-Bromo-3-chloro-[1, 2, 4] triazolo [4, 3-a] pyridine (1.11 g, 4.79 mmol) in benzyl amine (5 mL) was heated at 140° C. overnight. The reaction was diluted with water (100 mL) and extracted with EtOAc (2×50 mL). The combined organic layers were washed with brine (50 mL), dried with Na$_2$SO$_4$, and concentrated. The crude material was chromatographed (20-25% EtOAc/hexane) to give N-benzyl-6-bromo-[1,2,4]triazolo[4,3-a]pyridin-3-amine (0.43 g, 29%); ESI +ve 303.17 [M+1].

N³-Benzyl-[1,2,4]triazolo[4,3-a]pyridine-3,6-diamine

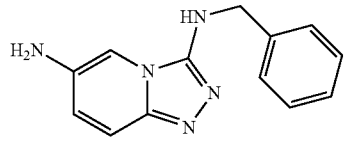 [SMILES: Nc1ccc2nnc(NCc3ccccc3)n2c1]

N-Benzyl-6-bromo-[1,2,4]triazolo[4,3-a]pyridin-3-amine (0.10 g, 0.33 mmol) in DMSO (2 mL) was treated with $K_2CO_3$ (0.038 g, 0.49 mmol), L-proline (0.015 g, 0.13 mmol) and CuI (0.012 g, 0.07 mmol) at rt and stirred for 15 min. $NH_4OH$ (25%) (0.03 mL, 0.49 mmol) was added to the reaction mixture and heated at 90° C. overnight. The reaction was diluted with water (50 mL) and extracted with EtOAc (2×25 mL). The combined organic layers were washed with brine (50 mL), dried with $Na_2SO_4$, and concentrated to yield N³-benzyl-[1,2,4]triazolo[4,3-a]pyridine-3,6-diamine (0.06 g, 77%); ESI +ve 240.30 [M+1].

Example 59: N-(3-(Benzylamino)-[1,2,4]triazolo[4,3-a]pyridine-6-yl)-4-methoxybenzenesulfonamide

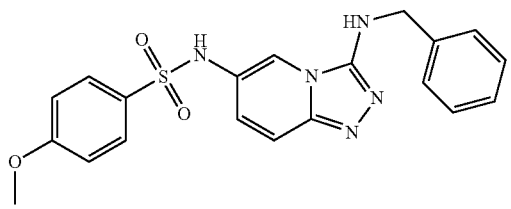 [SMILES: COc1ccc(S(=O)(=O)Nc2ccc3nnc(NCc4ccccc4)n3c2)cc1]

N³-Benzyl-[1,2,4]triazolo[4,3-a]pyridine-3,6-diamine (0.20 g, 0.84 mmol) in pyridine (2 mL) was treated with 4-methoxy-benzenesulfonylchloride (0.17 g, 0.84 mmol) at 0° C., then stirred overnight at rt. The reaction was diluted with water (100 mL) and extracted with EtOAc (2×100 mL). The combined organic layers were washed with brine (50 mL), dried with $Na_2SO_4$, and concentrated. The crude was chromatographed (35-40% EtOAc/hexane) to yield N-(3-(benzylamino)-[1,2,4]triazolo[4,3-a]pyridine-6-yl)-4-methoxybenzenesulfonamide (0.02 g, 6%); ESI +ve 410.29 [M+1]; $^1$H NMR: (400 MHz, DMSO-$d_6$) δ: 3.80 (s, 3H), 4.40-4.42 (d, J=5.6 Hz, 2H), 7.05-7.10 (t, 3H), 7.21-7.22 (d, J=6.4 Hz, 2H), 7.27-7.34 (m, 5H), 7.62-7.64 (d, J=8.4 Hz, 2H), 8.15 (s, 1H), 10.0 (s, 1H).

2-Chloropyridine-4-sulfonyl chloride

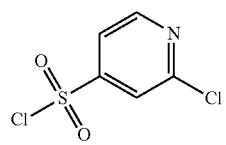 [SMILES: O=S(=O)(Cl)c1ccnc(Cl)c1]

4-Amino-2-chloropyridine (1.29 g, 10 mmol), TFA (10 mL), and con HCl (5 mL) was treated with $NaNO_2$ (2.07 g, 30 mmol) in water (7.5 mL) at 0° C., then stirred for 1 h at 0° C. The solution was filtered at −5° C. and added to a solution of CuCl (0.10 g, 0.7 mmol), $CuCl_2$ (0.67 g, 3.9 mmol) in HOAc containing dissolved $SO_2$ (60 mL) (prepared by bubbling $SO_2$ gas through HOAc at rt for 2 h) at 0° C. The reaction mixture was stirred at 0° C. for 1.5 h and diluted with DCM (50 mL). The reaction was washed with ice-water (2×50 mL), sat'd $NaHCO_3$ (2×50 mL), and brine (50 mL). The organic layer was dried with $Na_2SO_4$, and concentrated to yield 2-chloropyridine-4-sulfonyl chloride (1.05 g, 49%); $^1$H NMR: (400 MHz, DMSO-$d_6$) δ: 7.82-7.84 (m, 1H), 7.93 (s, 1H), 8.78-8.80 (m, 1H).

2-Chloro-N,N-diethylpyridine-4-sulfonamide

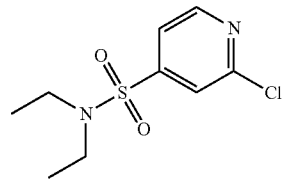

Diethyl amine (0.51 mL, 4.90 mmol) and TEA (2.06 mL, 14.8 mmol) in DCM (10 mL) at 0° C. was stirred for 30 min. 2-Chloropyridine-4-sulfonyl chloride (1.05 g, 4.90 mmol) was added at 0° C. and the reaction stirred at rt overnight. The reaction was diluted with water (50 mL) and extracted with DMC (2×25 mL). The combined organic layers were washed with brine (50 mL), dried with $Na_2SO_4$, and concentrated. The crude product was purified by chromatography (15-20% EtOAc/hexane) to yield 2-chloro-N,N-diethylpyridine-4-sulfonamide (0.70 g, 57%); ESI +ve 249.15 [M+1].

N,N-Diethyl-2-hydrazinylpyridine-4-sulfonamide

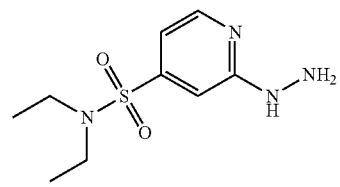 [SMILES: CCN(CC)S(=O)(=O)c1ccnc(NN)c1]

2-Chloro-N,N-diethylpyridine-4-sulfonamide (0.70 g, 2.8 mmol) in EtOH (5 mL) was treated with hydrazine (0.70 g, 14 mmol) at 0° C. and then refluxed overnight. The reaction was cooled to rt. The EtOH was distilled and the solid triturated with $Et_2O$ to give N,N-diethyl-2-hydrazinylpyridine-4-sulfonamide (0.32 g, 46%); ESI +ve 245.25 [M+1].

N,N-Diethyl-3-oxo-2,3-dihydro-[1,2,4]triazolo[4,3-a]pyridine-7-sulfonamide

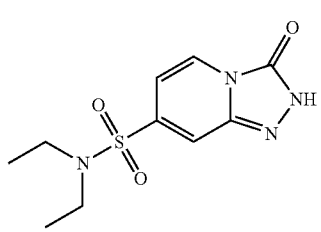 [SMILES: CCN(CC)S(=O)(=O)c1ccn2c(=O)[nH]nc2c1]

N,N-Diethyl-2-hydrazinylpyridine-4-sulfonamide (0.32 g, 1.3 mmol) in THF (5 mL) was treated with CDI (0.318 g, 1.9 mmol) at rt and then stirred at reflux overnight. The reaction was diluted with water (50 mL) and extracted in EtOAc (2×50 mL). The combined organic layers were washed with brine (50 mL), dried with Na$_2$SO$_4$, and concentrated. The crude product was purified by chromatography (40-45% EtOAc/hexane) to give N,N-diethyl-3-oxo-2,3-dihydro-[1,2,4]triazolo[4,3-a]pyridine-7-sulfonamide (0.125 g, 35%); ESI +ve 271.26 [M+1].

3-Chloro-N,N-diethyl-[1,2,4]triazolo[4,3-a]pyridine-7-sulfonamide

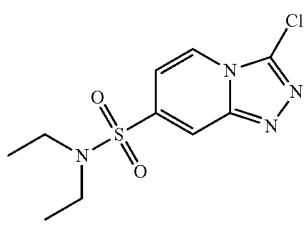 [SMILES: CCN(CC)S(=O)(=O)c1ccn2c(Cl)nnc2c1]

N,N-Diethyl-3-oxo-2,3-dihydro-[1,2,4]triazolo[4,3-a]pyridine-7-sulfonamide (0.125 g, 0.40 mmol) in POCl$_3$ (1 mL) was heated to 100° C. overnight. The reaction was cooled, poured onto crushed ice, and neutralized with sat'd NaHCO$_3$. The mixture was extracted with EtOAc (2×15 mL), and the combined organics were washed with brine (50 mL), dried with Na$_2$SO$_4$, and concentrated to yield 3-chloro-N,N-diethyl-[1,2,4]triazolo[4,3-a]pyridine-7-sulfonamide (0.04 g, 30%); ESI +ve 288.76 [M+1].

Example 60: N,N-Diethyl-3-(neopentylamino)-[1,2,4]triazolo[4,3-a]pyridine-7-sulfonamide

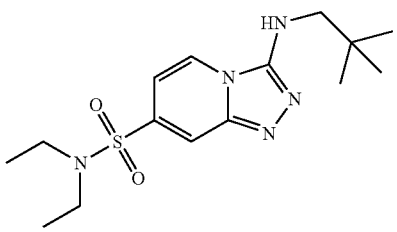 [SMILES: CCN(CC)S(=O)(=O)c1ccn2c(NCC(C)(C)C)nnc2c1]

3-Chloro-N,N-diethyl-[1,2,4]triazolo[4,3-a]pyridine-7-sulfonamide (0.10 g, 0.30 mmol) in neopentyl amine (1 mL) was heated at 120° C. overnight. The reaction was cooled, diluted with water (50 mL) and extracted with EtOAc (2×25 mL). The organics were washed with brine (50 mL), dried with Na$_2$SO$_4$, and concentrated to yield N,N-diethyl-3-(neopentylamino)-[1,2,4]triazolo[4,3-a]pyridine-7-sulfonamide (0.009 g, 8%); ESI +ve 340.43 [M+1]; $^1$H NMR: (400 MHz, DMSO-d$_6$) δ: 0.92 (s, 9H), 1.05-1.09 (t, J=7.2 Hz, 6H) 3.11-3.12 (d, J=6.4 Hz, 2H), 3.219-3.26 (q, J=7 Hz, 4H), 6.97-7.02 (m, 1H), 7.13-7.15 (m, 1H), 7.71 (s, 1H), 8.75-8.77 (d, J=6.8 Hz, 1H).

6-Chloro-2-methylpyridine-3-sulfonyl chloride

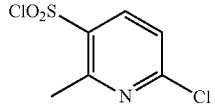

Thionyl chloride (4 mL, 29.6 mmol) was added over 1 h to water (24 mL), while the temperature was maintained 0-7° C., then the solution was stirred at 15° C. overnight. CuCl (0.010 g, 0.07 mmol) was added and cooled to −3° C. In another flask, a solution of 3-amino-6-chloro-2-methyl pyridine (1.00 g, 7.01 mmol) in con HCl (6.0 mL) at −5° C. was added dropwise to a solution of sodium nitrite (0.50 g, 7.5 mmol) in water (2 mL) while maintaining temperature −5 to 0° C. When the addition was complete, this solution was then added to the precooled thionyl chloride solution and stirred at −2° C. for 10 min, then at 0° C. for 75 min. The solid was filtered, washed with water and dried to give 6-chloro-2-methylpyridine-3-sulfonyl chloride (0.80 g, 51%); $^1$H NMR: (400 MHz, DMSO-d$_6$) δ: 2.67 (s, 3H), 7.28-7.30 (dd, J=0.4, 8.0 Hz, 1H), 8.00-8.02 (d J=8.0, 1H).

6-Chloro-N,N-diethyl-2-methylpyridine-3-sulfonamide

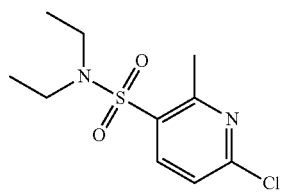 [SMILES: CCN(CC)S(=O)(=O)c1ccc(Cl)nc1C]

Diethyl amine (0.31 g, 4.24 mmol) and TEA (1.47 mL, 10.6 mmol) in DMC (10 mL) were cooled to 0° C. and treated 6-chloro-2-methylpyridine-3-sulfonyl chloride (0.80 g, 3.53 mmol) portionwise and stirred at rt overnight. The reaction was diluted with water (50 mL) and extracted with DMC (2×25 mL). The combined organic layers were washed with brine (50 mL), dried with Na$_2$SO$_4$, and concentrated to yield 6-chloro-N,N-diethyl-2-methylpyridine-3-sulfonamide (0.90 g, 98%); ESI +ve, 263.31 [M+H].

N,N-Diethyl-6-hydrazinyl-2-methylpyridine-3-sulfonamide

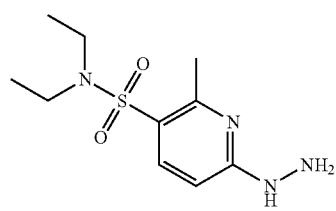 [SMILES: CCN(CC)S(=O)(=O)c1ccc(NN)nc1C]

6-Chloro-N,N-diethyl-2-methylpyridine-3-sulfonamide (0.9 g, 3.80 mmol) in EtOH (10 mL) was treated with hydrazine (0.76 g, 15.2 mmol) and heated to reflux overnight. After cooling, the ethanol was distilled and the resulting solid triturated with Et₂O to yield N,N-diethyl-6-hydrazinyl-2-methylpyridine-3-sulfonamide (0.8 g, 91%); ESI +ve, 259.36 [M+H].

N,N-Diethyl-5-methyl-3-oxo-2,3-dihydro-[1,2,4]triazolo[4,3-a]pyridine-6-sulfonamide

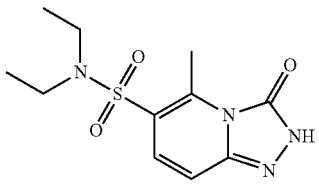 [SMILES: CCN(CC)S(=O)(=O)c1ccc2n[nH]c(=O)n2c1C]

N,N-Diethyl-6-hydrazinyl-2-methylpyridine-3-sulfonamide (0.8 g, 3.10 mmol) in THF (10 mL) was treated with CDI (0.75 g 4.6 5 mmol) and refluxed overnight. The reaction was diluted with water (100 mL) and extracted with EtOAc (200 mL). The organics were washed with water (2×100 mL), dried with Na₂SO₄, and concentrated. The crude product was purified by column chromatography (0-10% MeOH/DCM) to yield N,N-diethyl-5-methyl-3-oxo-2,3-dihydro-[1,2,4]triazolo[4,3-a]pyridine-6-sulfonamide (0.70 g, 79%); ESI +ve, 285.32 [M+H].

3-Chloro-N,N-diethyl-5-methyl-[1,2,4]triazolo[4,3-a]pyridine-6-sulfonamide

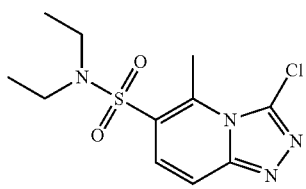 [SMILES: CCN(CC)S(=O)(=O)c1ccc2nnc(Cl)n2c1C]

N,N-Diethyl-5-methyl-3-oxo-2,3-dihydro-[1,2,4]triazolo[4,3-a]pyridine-6-sulfonamide (0.7 g) in POCl₃ (7 ml) was heated to 110° C. overnight. The reaction was cooled, poured onto crushed ice, and neutralized with sat'd NaHCO₃ (250 mL). The mixture was extracted with EtOAc (2×20 mL), and the combined organics were washed with brine (50 mL), dried with Na₂SO₄, and concentrated. The crude product was purified by column chromatography (0-2% MeOH/DCM) to give 3-chloro-N,N-diethyl-5-methyl-[1,2,4]triazolo[4,3-a]pyridine-6-sulfonamide (0.3 g, 40%); ESI +ve, 303.32 [M+H].

Example 61: 3-(Benzylamino)-N,N-diethyl-5-methyl-[1,2,4]triazolo[4,3-a]pyridine-6-sulfonamide

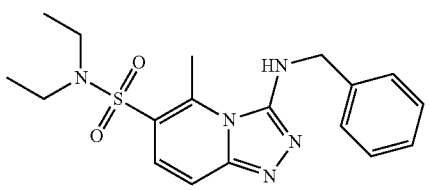 [SMILES: CCN(CC)S(=O)(=O)c1ccc2nnc(NCc3ccccc3)n2c1C]

A solution of 3-chloro-N,N-diethyl-5-methyl-[1,2,4]triazolo[4,3-a]pyridine-6-sulfonamide (0.3 g, 0.99 mmol) in benzyl amine (1 mL) was heated at 140° C. overnight. The reaction mixture was cooled, diluted with water (20 mL) and extracted with EtOAc (2×15 mL). The organics were washed with brine (10 mL), dried with Na₂SO₄, and concentrated. The crude product was purified by column chromatography (35-40% EtOAc/hexane) to yield 3-(benzylamino)-N,N-diethyl-5-methyl-[1,2,4]triazolo[4,3-a]pyridine-6-sulfonamide (0.075 g, 37%); ESI +ve, 374.93 [M+H]; ¹H NMR: (400 MHz, DMSO-d₆) δ: 1.04-1.07 (t, 6H), 2.90 (s, 3H), 3.21-3.26 (q, 4H), 4.49-4.51 (d, J=6.4, 2H), 7.20-7.29 (m, 3H), 7.36-7.39 (m, 3H), 7.59-7.62 (t, 1H), 7.76-7.78 (d, J=9.2, 1H).

2-Chloro-5-(phenylthio)pyridine

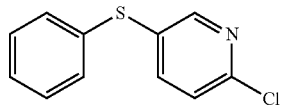 [SMILES: Clc1ccc(Sc2ccccc2)cn1]

A NaOMe solution (0.37 M in MeOH) (40 mL, 15 mmol) was treated with 2-chloro-5-iodopyridine (3.0 g, 12.5 mmol), thiophenol (1.65 g, 15 mmol) and copper (0.318 g, 5.0 mmol) at rt, then heated to reflux overnight. After cooling to rt, the reaction was diluted with 1N NaOH (50 mL), the MeOH distilled, and the aqueous layer extracted with EtOAc (2×100 mL). The organics were with brine (50 mL), dried with Na₂SO₄, and concentrated to yield 2-chloro-5-(phenylthio) pyridine (4.2 g); ESI +ve 222.1 [M+1].

2-Chloro-5-(phenylsulfonyl)pyridine

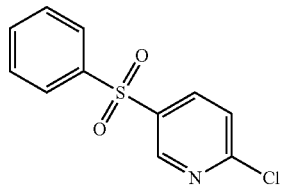 [SMILES: O=S(=O)(c1ccccc1)c1ccc(Cl)nc1]

2-Chloro-5-(phenylthio) pyridine (4.0 g, 18.1 mmol) in DCM (50 mL) was treated with mCPBA (50%) (13.0 g, 45.3 mmol) in DCM (50 mL) and stirred for 1 h at 0-10° C. The precipitate was filtered, and the filtrate diluted with DCM, washed with 1N NaOH (2×25 mL) and brine (50 mL), dried with Na₂SO₄, and concentrated to yield 2-chloro-5-(phenylsulfonyl)pyridine (2.3 g, 50%); ¹H NMR: (400 MHz, DMSO) δ: 7.00-7.02 (m, 2H), 7.63-7.65 (m, 2H), 7.99-8.00 (d, J=7.6, 2H), 8.40-8.42 (m, 1H), 9.02-9.03 (s, 1H).

2-Hydrazinyl-5-(phenylsulfonyl)pyridine

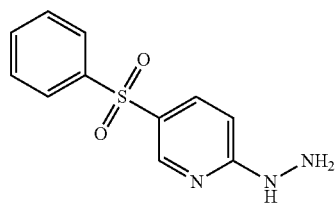 [SMILES: NNc1ccc(S(=O)(=O)c2ccccc2)cn1]

2-Chloro-5-(phenylsulfonyl) pyridine (2.3 g, 9.09 mmol) in EtOH (40 mL) was treated with hydrazine (99%) (1.81 g, 36.4 mmol) at 0° C., then heated to reflux overnight. After cooling to rt, the reaction was concentrated and the residue triturated with Et₂O to give 2-hydrazinyl-5-(phenylsulfonyl) pyridine (1.2 g, 53%); ESI +ve 250.1 [M+1].

6-(Phenylsulfonyl)-[1,2,4]triazolo[4,3-a]pyridin-3(2H)-one

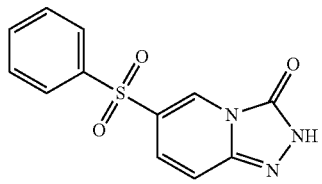 [SMILES: O=c1[nH]nc2ccc(S(=O)(=O)c3ccccc3)cn12]

2-Hydrazinyl-5-(phenylsulfonyl)pyridine (0.5 g, 2.0 mmol) in dichloroethane (15 mL) at rt was treated with CDI (0.49 g, 3.0 mmol), then heated to reflux overnight. The reaction was concentrated and the residue treated with water (50 mL). The precipitate was filtered and dried to give 6-(phenylsulfonyl)-[1,2,4]triazolo[4,3-a]pyridin-3(2H)-one (0.40 g, 72%); ESI +ve 276.1 [M+1].

3-Chloro-6-(phenylsulfonyl)-[1,2,4]triazolo[4,3-a]pyridine

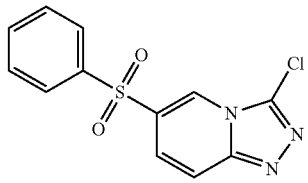 [SMILES: O=S(=O)(c1ccccc1)c1ccc2nnc(Cl)n2c1]

6-(Phenylsulfonyl)-[1,2,4]triazolo[4,3-a]pyridin-3(2H)-one (0.40 g, 1.45 mmol) in POCl₃ (4 mL) was heated at 110° C. overnight. After cooling to rt, the reaction was poured onto ice, neutralized with sat'd NaHCO₃, and extracted with EtOAc (2×25 mL). The organics were washed with brine, dried with Na₂SO₄, and concentrated to yield 3-chloro-6-(phenylsulfonyl)-[1,2,4]triazolo[4,3-a]pyridine (0.140 g, 32 mmol); ESI +ve 294.0 [M+1].

Example 62: (R)—N-(1-Phenylethyl)-6-(phenylsulfonyl)-[1,2,4]triazolo[4,3-a]pyridin-3-amine

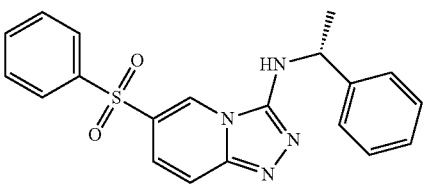 [SMILES: C[C@@H](Nc1nnc2ccc(S(=O)(=O)c3ccccc3)cn12)c1ccccc1]

3-Chloro-6-(phenylsulfonyl)-[1,2,4]triazolo[4,3-a]pyridine (0.13 g, 0.44 mmol) in (R)-1-phenylethan-1-amine (0.2 mL) was heated at 140° C. overnight. The reaction was cooled, diluted with water (50 mL) and extracted with EtOAc (2×30 mL). The organics were washed with brine (25 mL), dried with Na₂SO₄, and concentrated. The crude product was chromatographed (25% EtOAc/hexane) to yield (R)—N-(1-phenylethyl)-6-(phenylsulfonyl)-[1,2,4]triazolo[4,3-a]pyridin-3-amine (0.075 g, 44%); ESI +ve 379.1 [M+1]; ¹H NMR: (400 MHz, DMSO-d₆) δ: 1.45-1.46 (d, J=6.8, 3H), 4.87-4.91 (m, 1H), 7.16-7.20 (t, 1H), 7.27-7.30 (t, 2H), 7.38-7.40 (d, J=7.6, 2H), 7.46-7.49 (dd, J=9.2, 1H), 7.60-7.63 (t, 2H), 7.67-7.72 (m, 2H), 7.75-7.77 (dd, J=2, 9.2, 1H), 8.03-8.05 (m, 1H), 9.25 (s, 1H).

Representative compounds of the invention were prepared in a similar manner to example 62 using the appropriate amines.

| No. | Structure | LCMS m/z |
|---|---|---|
| 62 | 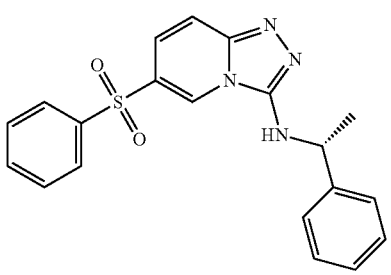 [SMILES: C[C@@H](Nc1nnc2ccc(S(=O)(=O)c3ccccc3)cn12)c1ccccc1] | 379.4 |

-continued

| No. | Structure | LCMS m/z |
|---|---|---|
| 63 | 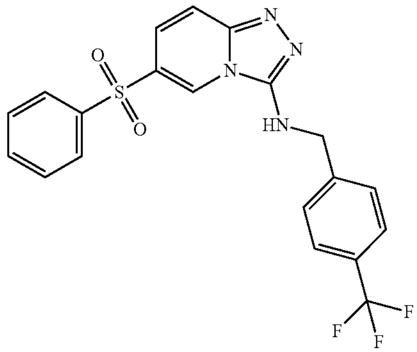 [SMILES: O=S(=O)(c1ccccc1)c1ccc2nnc(NCc3ccc(C(F)(F)F)cc3)n2c1] | 433.4 |
| 64 | 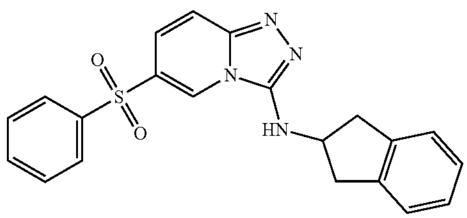 [SMILES: O=S(=O)(c1ccccc1)c1ccc2nnc(NC3Cc4ccccc4C3)n2c1] | 391.5 |
| 65 | 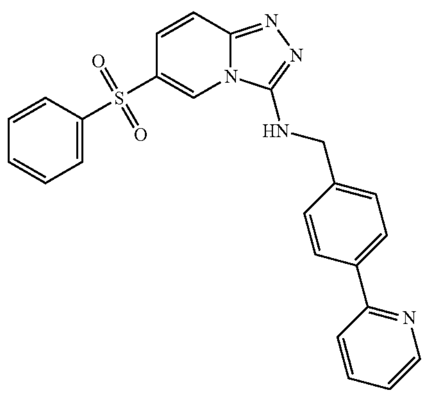 [SMILES: O=S(=O)(c1ccccc1)c1ccc2nnc(NCc3ccc(-c4ccccn4)cc3)n2c1] | 442.5 |
| 66 | 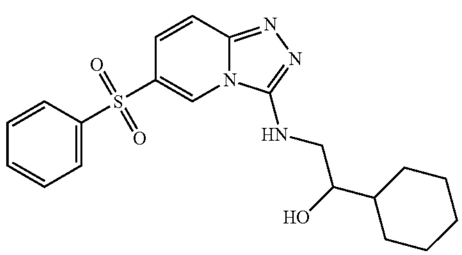 [SMILES: O=S(=O)(c1ccccc1)c1ccc2nnc(NCC(O)C3CCCCC3)n2c1] | 401.5 |
| 67 | 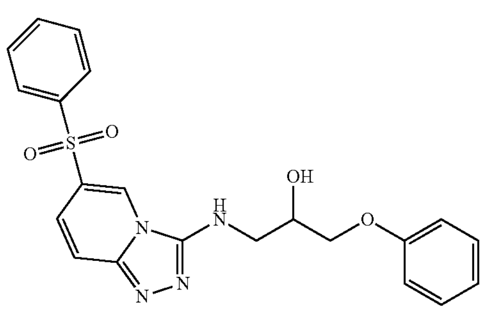 [SMILES: O=S(=O)(c1ccccc1)c1ccc2nnc(NCC(O)COc3ccccc3)n2c1] | 425.5 |

-continued

| No. | Structure | LCMS m/z |
|---|---|---|
| 68 | 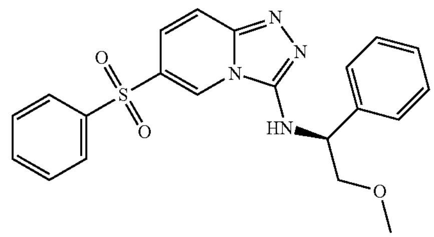 [SMILES: COC[C@@H](Nc1nnc2ccc(S(=O)(=O)c3ccccc3)cn12)c1ccccc1] | 409.5 |
| 69 | 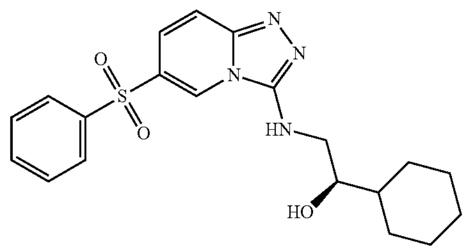 | 401.5 |
| 70 | 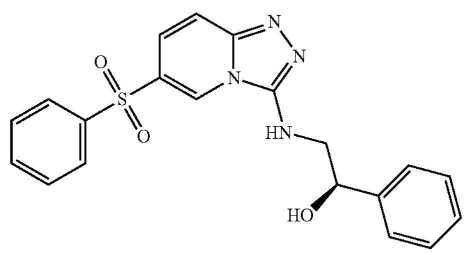 [SMILES: O=S(=O)(c1ccccc1)c1ccc2nnc(NC[C@H](O)c3ccccc3)n2c1] | 395.4 |
| 71 | 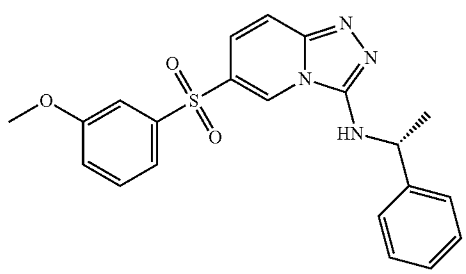 [SMILES: COc1cccc(S(=O)(=O)c2ccc3nnc(N[C@H](C)c4ccccc4)n3c2)c1] | 409.5 |
| 72 | 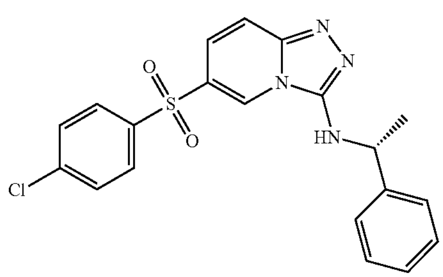 [SMILES: C[C@@H](Nc1nnc2ccc(S(=O)(=O)c3ccc(Cl)cc3)cn12)c1ccccc1] | 413.9 |
| 73 | 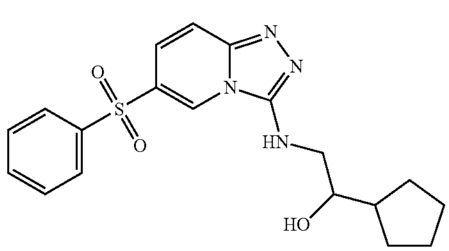 [SMILES: O=S(=O)(c1ccccc1)c1ccc2nnc(NCC(O)C3CCCC3)n2c1] | 387.5 |

-continued

| No. | Structure | LCMS m/z |
|---|---|---|
| 74 | 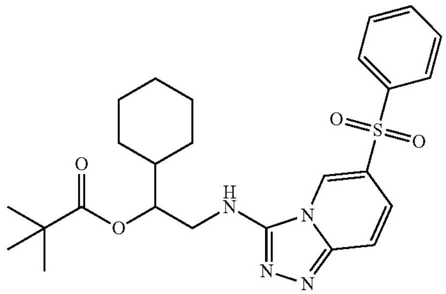 [SMILES: CC(C)(C)C(=O)OC(CNc1nnc2ccc(S(=O)(=O)c3ccccc3)cn12)C1CCCCC1] | 485.6 |
| 75 | 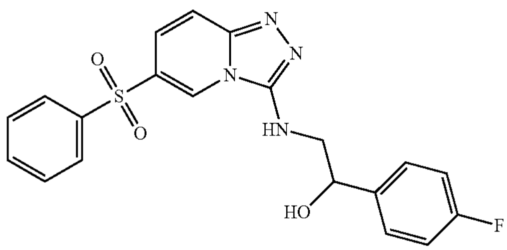 [SMILES: O=S(=O)(c1ccccc1)c1ccc2nnc(NCC(O)c3ccc(F)cc3)n2c1] | 413.4 |
| 76 | 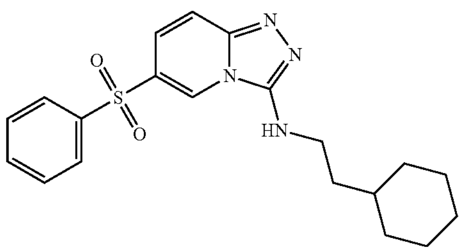 [SMILES: O=S(=O)(c1ccccc1)c1ccc2nnc(NCCC3CCCCC3)n2c1] | 385.5 |
| 77 | 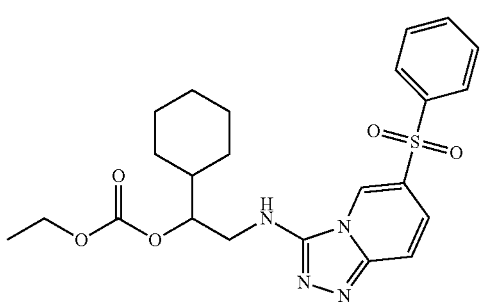 [SMILES: CCOC(=O)OC(CNc1nnc2ccc(S(=O)(=O)c3ccccc3)cn12)C1CCCCC1] | 473.6 |
| 78 | 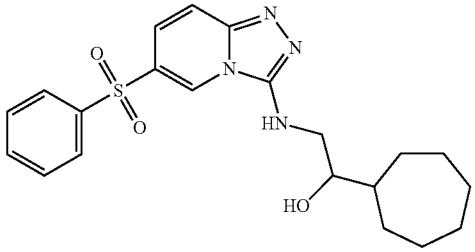 [SMILES: O=S(=O)(c1ccccc1)c1ccc2nnc(NCC(O)C3CCCCCC3)n2c1] | 415.5 |

| No. | Structure | LCMS m/z |
|---|---|---|
| 79 | 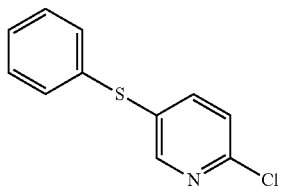 [SMILES: Clc1ccc(Sc2ccccc2)cn1] | 399.5 |

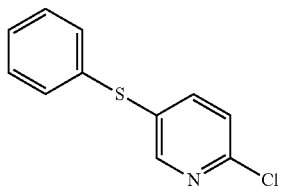 [SMILES: Clc1ccc(Sc2ccccc2)cn1]

2-chloro-5-(phenylthio) pyridine

To a stirred solution of methanol (700 mL) was added Na metal (8.06 g, 350 mmol) at 25° C. Once the Na metal dissolved, 2-chloro-5-iodopyridine (70.0 g, 292.34 mmol), benzenethiol (38.64 g, 350.7 mmol) and copper (7.42 g, 116.758 mmol) were added and the mixture was heated at 80° C. for 16 h. The reaction was cooled to 25° C., 1N NaOH (500 mL) was added and the methanol was evaporated. The reaction mixture was diluted with water (500 mL) and the product was extracted into ethyl acetate (2×500 mL). The organic layer was washed with brine (500 mL), dried over anhydrous sodium sulfate and distilled off to obtain crude 2-chloro-5-(phenylthio) pyridine (80.0 g, (221.90 [M+1])) as a liquid which was carried forward to next step without purification.

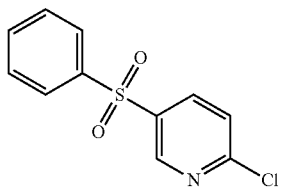 [SMILES: O=S(=O)(c1ccccc1)c1ccc(Cl)nc1]

2-chloro-5-(phenylsulfonyl)pyridine

To a stirred solution of 2-chloro-5-(phenylthio) pyridine (80.0 g, 361.9 mmol) in MDC (500 mL) was added a solution of 60% mCPBA (260.0 g, 904.9 mmol) in MDC (500 mL) drop wise at 0-10° C. The reaction stirred at 25° C. for 2 h. The precipitate was filtered off, and the filtrate was washed with 1N NaOH (500 mL*2) and brine (500 mL), dried over anhydrous sodium sulfate and distilled off. The crude product was purified by column chromatography (20% ethyl acetate in hexane) to obtained 2-chloro-5-(phenylsulfonyl)pyridine (65 g).

5-(phenylsulfonyl)pyridin-2-amine

A solution of 2-chloro-5-(phenylsulfonyl)pyridine (65.0 g, 256.9 mmol) in Aq. ammonia (650 mL) was stirred at 100° C. in autoclave for 16 h. The reaction mixture cooled to 25° C. and was diluted with water (1000 mL). The solid was filtered and dried under vacuum to obtained 5-(phenylsulfonyl)pyridin-2-amine (52.0 g, 235 [M+1]). 1H NMR: (400 MHz, DMSO) δ: 6.476-6.498 (d, J=8.8, 1H), 7.108 (s, 2H), 7.576-7.616 (m, 2H), 7.636-7.675 (m, 1H), 7.754-7.783 (m, 1H), 7.887-7.909 (m, 2H), 8.430-8.436 (d, J=2.4, 1H).

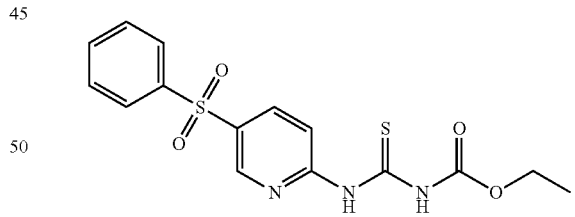

Ethyl 1-(carboxamide)-3-(5-(phenylsulfonyl)pyridin-2-yl)thiourea

To a stirred solution of 5-(phenylsulfonyl) pyridin-2-amine (52.0 g, 222.0 mmol) in dioxane (500 mL) was added ethoxycarbonyl isothiocyanate (29.12 g, 222.0 mmol) at 25° C. under nitrogen atmosphere and the resulting reaction mixture was stirred at 25° C. for 16 h. Solvent was distilled off, water (1000 mL) was added and the mixture stirred for 1 h. The solid was filtered and dried under vacuum to obtained the thio-urea derivative (74.0 g, 365.9 [M+1]).

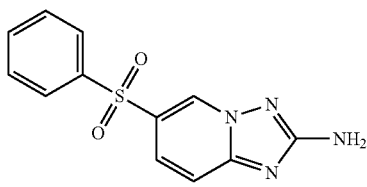 [SMILES: Nc1nc2ccc(S(=O)(=O)c3ccccc3)cn2n1]

6-(phenylsulfonyl)-[1,2,4]triazolo[1,5-a]pyridin-2-amine

To a stirred solution of hydroxylamine hydrochloride (70.44 g, 1013 mmol) in methanol (600 mL) and ethanol (600 mL) was added DIPEA (112.29 mL, 608 mmol) drop wise at 25° C. Next, the thio-urea derivative (74.0 g, 202.7 mmol) was added in one portion at 25° C. and the reaction was stirred for 2 h at 25° C. and then at 60° C. for 16 h. Solvent was distilled off, the reaction mass was diluted with water (1000 mL), and the resulting mixture stirred for 1 h. The solid was filtered and dried under vacuum to obtained 6-(phenylsulfonyl)-[1,2,4]triazolo[1,5-a]pyridin-2-amine (52.0 g, 274.9 [M+]). 1H NMR: (400 MHz, DMSO) δ: 6.539 (s, 2H), 7.460-7.484 (d, J=9.6, 1H), 7.619-7.656 (t, 2H), 7.693-7.729 (m, 1H), 7.757-7.785 (d, J=9.2 1H), 8.043-8.067 (d, J=8.8, 2H), 9.250-9.253 (d, J=1.2, 1H).

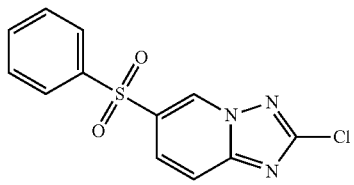 [SMILES: O=S(=O)(c1ccccc1)c1ccc2nc(Cl)nn2c1]

2-chloro-6-(phenylsulfonyl)-[1,2,4]triazolo[1,5-a]pyridine

To a stirred solution of 6-(phenylsulfonyl)-[1,2,4]triazolo[1,5-a]pyridin-2-amine (52.0 g, 189.4 mmol) in conc HCl (625 mL) was added copper(II)chloride dihydrate (8.39 g, 49.24 mmol) at 25° C. The reaction mixture was cooled to 0-5° C. and sodium nitrite (15.68 g, 227.0 mmol) in water (293 mL) was added drop wise at 0-5° C. over 30 min and the reaction stirred at 25° C. for 16 h. The reaction mass was diluted with water (3000 mL) and stirred for 1 h. The solid was filtered and dried under vacuum to give crude product which was purified by column chromatography (2% methanol in MDC) to obtained 2-chloro-6-(phenylsulfonyl)-[1,2,4]triazolo[1,5-a]pyridine (44.0 g) 1H NMR: (400 MHz, DMSO) δ: 7.638-7.686 (m, 2H), 7.726-7.769 (m, 1H), 7.967-8.006 (m, 1H), 8.092-8.125 (m, 3H), 9.741 (s, 1H).

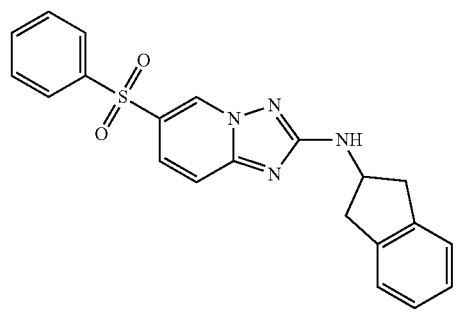 [SMILES: O=S(=O)(c1ccccc1)c1ccc2nc(NC3Cc4ccccc4C3)nn2c1]

Example 80: N-(2,3-dihydro-1H-inden-2-yl)-6-(phenylsulfonyl)-[1,2,4]triazolo[1,5-a]pyridin-2-amine A stirred solution of 2-chloro-6-(phenylsulfonyl)-[1,2,4]triazolo[1,5-a]pyridine (0.15 g, 0.51 mmol) in 2,3-dihydro-1H-inden-2-amine (0.15 mL) was heated at 140° C. for 16 h. The reaction mixture was cooled, diluted with methanol and filtered. The crude solid product was purified by column chromatography (30% ethyl acetate in hexane) to obtained N-(2,3-dihydro-1H-inden-2-yl)-6-(phenylsulfonyl)-[1,2,4]triazolo[1,5-a]pyridin-2-amine (0.140 g, 391.4 [M+1]. 1H NMR: (400 MHz, DMSO) (13525) δ: 2.906-2.962 (m, 2H), 3.248-3.306 (m, 2H), 4.431-4.483 (m, 1H), 7.137-7.169 (m, 2H), 7.204-7.234 (m, 2H), 7.460-7.476 (d, 6.4 Hz, 1H), 7.517-7.540 (d, 9.2 Hz, 1H), 7.626-7.663 (m, 2H), 7.697-7.737 (m, 1H), 7.794-7.822 (m, 1H), 8.064-8.085 (m, 2H), 9.347-9.350 (d, 1.2 Hz, 1H).

Representative compounds of the invention were prepared in a similar manner to example 80 from 2-chloro-6-(phenylsulfonyl)-[1,2,4]triazolo[1,5-a]pyridine and the appropriate amine.

| No. | Structure | LCMS m/z |
|---|---|---|
| 81 | 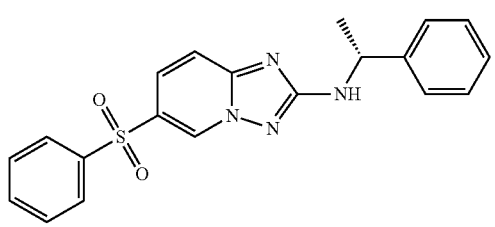 [SMILES: C[C@@H](Nc1nc2ccc(S(=O)(=O)c3ccccc3)cn2n1)c1ccccc1] | 379 |

-continued
| No. | Structure | LCMS m/z |
|---|---|---|
| 82 | 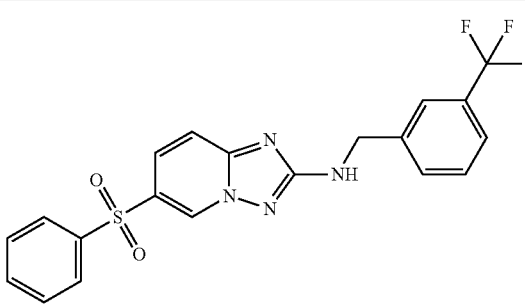 | 433 |
| 83 | 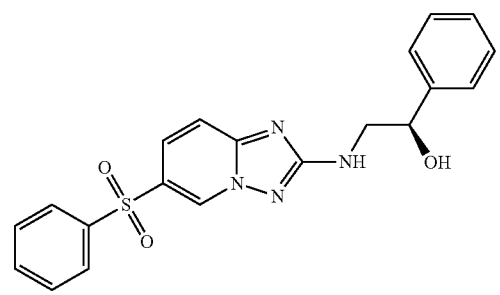 [SMILES: O=S(=O)(c1ccccc1)c1ccc2nc(NC[C@H](O)c3ccccc3)nn2c1] | 395 |
| 84 | 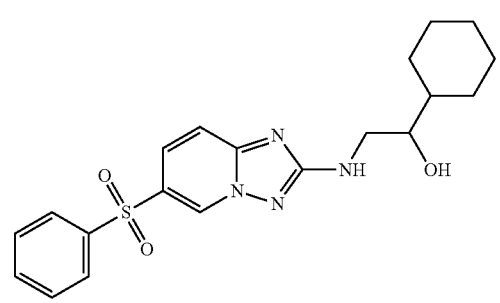 [SMILES: O=S(=O)(c1ccccc1)c1ccc2nc(NCC(O)C3CCCCC3)nn2c1] | 401 |
| 85 | 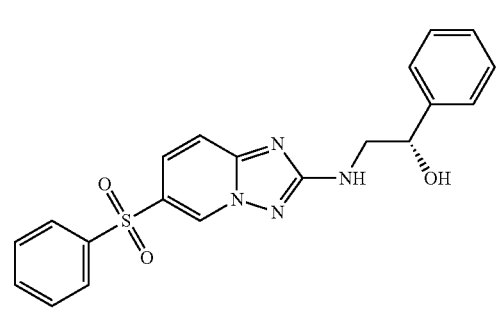 [SMILES: O=S(=O)(c1ccccc1)c1ccc2nc(NC[C@@H](O)c3ccccc3)nn2c1] | 395 |
| 86 | 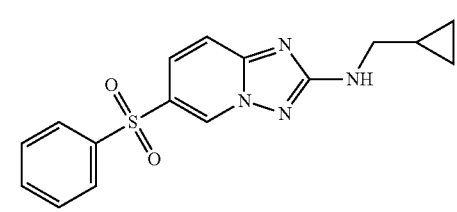 [SMILES: O=S(=O)(c1ccccc1)c1ccc2nc(NCC3CC3)nn2c1] | 329 |

-continued

| No. | Structure | LCMS m/z |
|---|---|---|
| 87 | 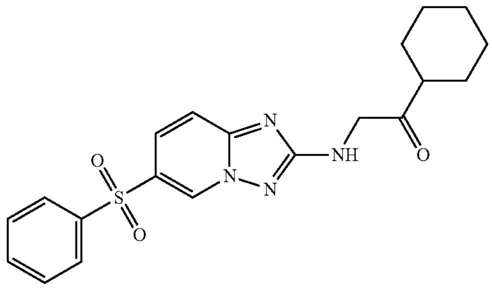 [SMILES: O=C(CNc1nc2ccc(S(=O)(=O)c3ccccc3)cn2n1)C1CCCCC1] | 399 |
| 88 | 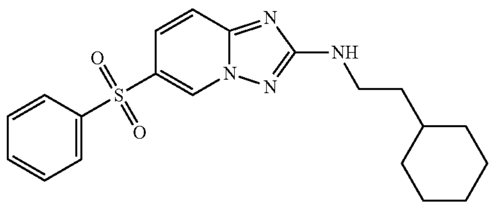 [SMILES: O=S(=O)(c1ccccc1)c1ccc2nc(NCCC3CCCCC3)nn2c1] | 385 |
| 90 | 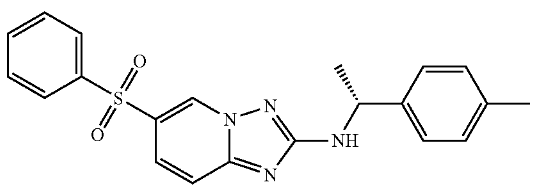 [SMILES: Cc1ccc([C@@H](C)Nc2nc3ccc(S(=O)(=O)c4ccccc4)cn3n2)cc1] | 393 |
| 91 | 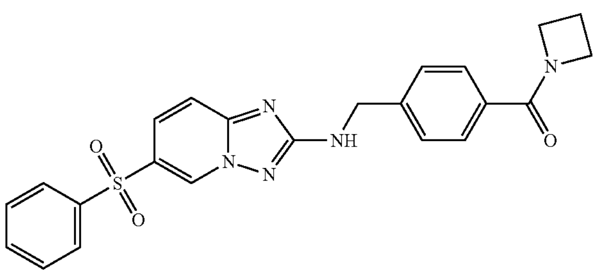 [SMILES: O=C(c1ccc(CNc2nc3ccc(S(=O)(=O)c4ccccc4)cn3n2)cc1)N1CCC1] | 448 |
| 92 | 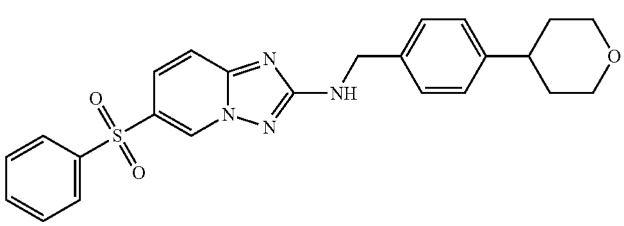 [SMILES: O=S(=O)(c1ccccc1)c1ccc2nc(NCc3ccc(C4CCOCC4)cc3)nn2c1] | 449 |
| 93 | 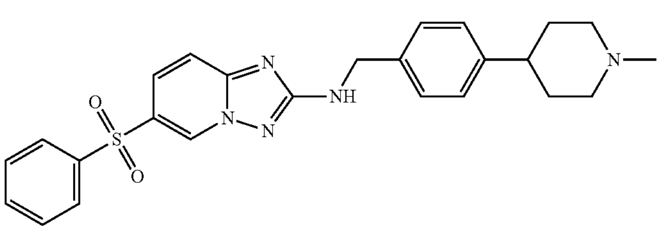 [SMILES: CN1CCC(c2ccc(CNc3nc4ccc(S(=O)(=O)c5ccccc5)cn4n3)cc2)CC1] | 462 |

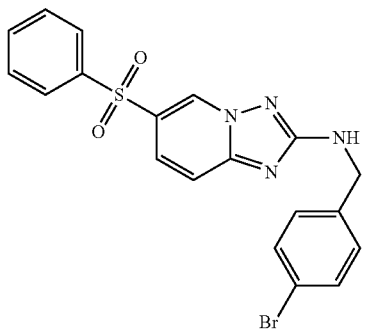 [SMILES: O=S(=O)(c1ccccc1)c1ccc2nc(NCc3ccc(Br)cc3)nn2c1]

(N-(4-bromobenzyl)-6-(phenylsulfonyl)-[1,2,4]triazolo[1,5-a]pyridin-2-amine

A stirred solution of 2-chloro-6-(phenylsulfonyl)-[1,2,4]triazolo[1,5-a]pyridine (40.0 g, 136.1 mmol) in (4-bromophenyl)methanamine (40 g, 214.9 mmol) was heated at 140° C. for 16 h. The reaction mixture was cooled, diluted with methanol and stirred for 1 h. The solid was filtered and dried under vacuum to obtained (N-(4-bromobenzyl)-6-(phenylsulfonyl)-[1,2,4]triazolo[1,5-a]pyridin-2-amine (38.0 g, 444.9 [M+1]) 1H NMR: (400 MHz, DMSO) δ: 4.437-4.453 (d, J=6.4, 2H), 7.286-7.307 (d, J=8.4, 2H), 7.482-7.520 (m, 3H), 7.611-7.649 (t, 2H), 7.688-7.738 (q, 2H), 7.783-7.811 (d, J=9.2, 1H), 8.042-8.063 (d, J=8.4, 2H), 9.287-9.290 (d, J=1.2, 1H).

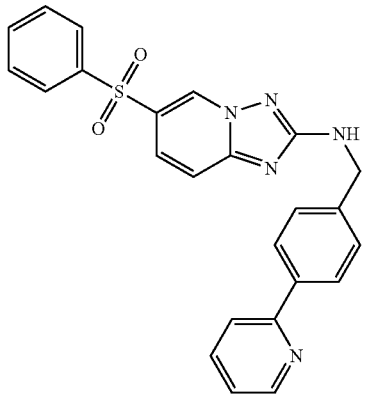 [SMILES: O=S(=O)(c1ccccc1)c1ccc2nc(NCc3ccc(-c4ccccn4)cc3)nn2c1]

Example 94: 6-(phenylsulfonyl)-N-(4-(pyridin-2-yl)benzyl)-[1,2,4]triazolo[1,5-a]pyridin-2-amine To a stirred solution of N-(4-bromobenzyl)-6-(phenylsulfonyl)-[1,2,4]triazolo[1,5-a]pyridin-2-amine (42.0 g, 94.74 mmol) (420 mL) and 2-(tributylstannyl)pyridine (48.8 g, 132.6 mmol) in DMF was added copper(II) oxide (1.68 g) and the solution was degassed with Argon for 30 min. Tetrakis (10.92 g, 9.47 mmol) was added and the reaction was heated at 100° C. for 16 h. The reaction mixture was cooled and filtered through celite, and washed with ethyl acetate (2×500 mL). The filtrate was washed with water (2×500 mL), washed with brine (500 mL), dried over anhydrous sodium sulfate and the solvent was distilled off to obtain crude product which was purified by column chromatography (40% ethyl acetate in MDC) to obtained 6-(phenylsulfonyl)-N-(4-(pyridin-2-yl)benzyl)-[1,2,4]triazolo[1,5-a]pyridin-2-amine (14.3 g, 442 [M+1]). 1H NMR: (400 MHz, DMSO) δ: 4.537-4.553 (d, J=6.4, 2H), 7.345-7.347 (m, 1H), 7.441-7.462 (d, J=8.4, 2H), 7.505-7.506 (d, J=0.4, 1H), 7.607-7.645 (t, 2H), 7.684-7.702 (t, 1H), 7.752-7.791 (q, 2H), 7.858-7.862 (d, J=1.6, 1H), 8.014-8.034 (d, J=8, 1H), 8.044-8.056 (m, 4H), 8.636-8.650 (m, 1H), 9.306-9.311 (t, 1H).

Representative compounds of the invention were prepared in a similar manner to example 94 from N-(4-bromobenzyl)-6-(phenylsulfonyl)-[1,2,4]triazolo[1,5-a]pyridin-2-amine and the appropriate stannyl reagent.

| No. | Structure | LCMS m/z |
|---|---|---|
| 95 | 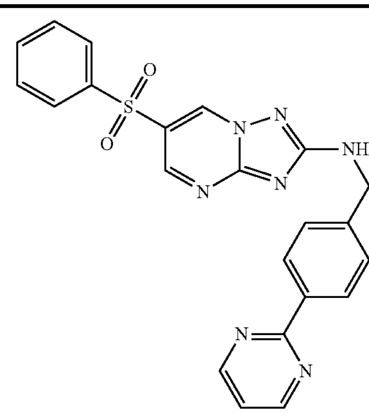 | 444 |

| No. | Structure | LCMS m/z |
|---|---|---|
| 96 | 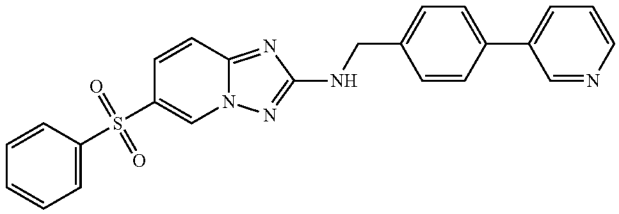 [SMILES: O=S(=O)(c1ccccc1)c1ccc2nc(NCc3ccc(-c4cccnc4)cc3)nn2c1] | 442 |
| 97 | 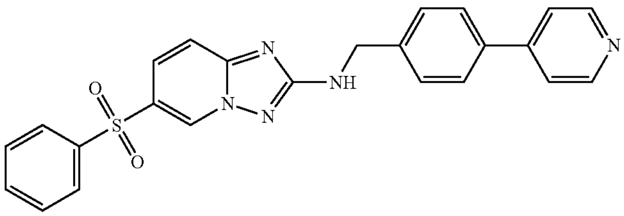 [SMILES: O=S(=O)(c1ccccc1)c1ccc2nc(NCc3ccc(-c4ccncc4)cc3)nn2c1] | 442 |

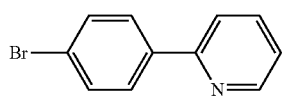 [SMILES: Brc1ccc(-c2ccccn2)cc1]

2-(4-bromophenyl)pyridine

To a stirred solution of 2-bromopyridine (5.0 g, 31.64 mmol) in THF:H₂O (50:25 mL) was added K₂CO₃ (6.91 g) at 25° C. The reaction mixture was degassed with Argon for 30 minutes. Then Tetrakis (462 mg) was added and the reaction was again degassed it with Argon for 15 minutes. (4-Bromophenyl)boronic acid (7.62 g, 37.97 mmol) was added and the reaction was degassed with Argon for 15 minutes and heated at 80° C. for 24 h. The reaction mixture was cooled to 25° C. The reaction mixture was diluted with water (500 mL) and extracted in EtOAc (250 mL×2). The organic layer was washed with brine (20 mL), dried over anhydrous sodium sulfate and distilled off to give crude product which was purified by Flash chromatography to give pure 2-(4-bromophenyl)pyridine as a light yellow liquid (4.1 g, 234.1 [M+H])¹H NMR: (400 MHz, CDCl3) (31678) δ: 7.50-7.55 (m, 1H), 7.57-7.61 (m, 2H), 7.68-7.78 (m, 2H), 7.80-7.90 (m, 2H), 8.70-8.71 (m, 1H).

Example 97: 6-(phenylsulfonyl)-N-(4-(pyridin-2-yl) phenyl)-[1,2,4]triazolo[1,5-a]pyridin-2-amine Prepared a solution of 6-(phenylsulfonyl)-[1,2,4]triazolo [1,5-a]pyridin-2-amine (300 mg, 1.09 mmol), 2-(4-bromophenyl)pyridine (304 mg, 1.31 mmol), davephos (68 mg, 0.17 mmol) and CS₂CO₃ (708 mg, 2.18 mmol) in dry 1, 4 Dioxane (15 mL). The reaction was degassed under nitrogen and vacuum for 10 minutes. Pd(OAc)₂ (39 mg, 0.17 mmol) was added and the reaction mixture was then heated to 90° C. for 16 h. The reaction mixture was cool, diluted with water (50 mL) and extracted with EtOAc (50 mL×2). The organic layer was washed with brine (30 mL), dried over anhydrous sodium sulfate and evaporated to dryness to give crude product which was purified by Flash chromatography (0-5% MDC in methanol) to give pure 6-(phenylsulfonyl)-N-(4-(pyridin-2-yl)phenyl)-[1,2,4]triazolo[1,5-a]pyridin-2-amine (10 mg, 428.09 [M+H]). ¹H NMR: (400 MHz, DMSO) (3716) δ: 7.27-7.30 (m, 1H), 7.66-7.68 (m, 2H), 7.71-7.75 (m, 3H), 7.81-7.86 (m, 2H), 7.91-7.95 (m, 2H), 8.06-8.12 (m, 4H), 8.62-8.63 (d, 1H), 9.545-9.548 (d, j=1.2 Hz, 1H), 10.197 (s, 1H).

Representative compounds of the invention were prepared in a similar manner to example 97 from 6-(phenylsulfonyl)-[1,2,4]triazolo[1,5-a]pyridin-2-amine and the appropriate aryl bromide.

| No. | Structure | LCMS m/z |
|---|---|---|
| 98 | 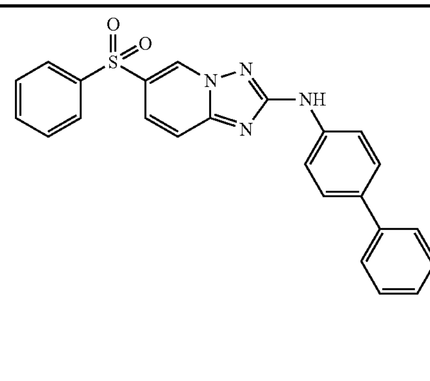 | 427 |

-continued

| No. | Structure | LCMS m/z |
|---|---|---|
| 99 | 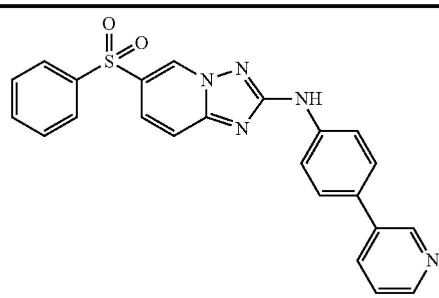 | 428 |

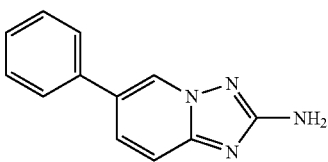 [SMILES: Nc1nc2ccc(-c3ccccc3)cn2n1]

5-phenylpyridin-2-amine

To a stirred solution of 5-bromopyridin-2-amine (2.0 g, 11.55 mmol) in Dioxane:H$_2$O (20:4 mL) was added phenylboronic acid (1.26 g. 10.40 mmol) and Na$_2$CO$_3$ (2.45 g, 23.14 mmol) at 25° C. The reaction mixture was degassed with Argon for 30 minutes. Tetrakis (668.5 mg, 0.578 mmol) was added. The reaction mixture was heated at 80° C. for 16 h. Then the reaction mixture was cooled, diluted with water (50 mL) and extracted in EtOAc (150 mL×2) The organic layer was washed with brine (20 mL), dried over anhydrous sodium sulfate and distilled off to give crude product which was purified by Flash chromatography to give pure 5-phenylpyridin-2-amine (1.8 g). $^1$H NMR: (400 MHz, DMSO) (31196) δ: 6.07 (s, 2H), 6.51-6.53 (m, 2H), 7.24-7.28 (m, 2H), 7.38-7.42 (m, 2H), 7.55-7.57 (m, 2H), 7.62-7.71 (m, 1H), 8.24-8.25 (d, J=2.0 Hz, 1H).

6-phenyl-[1,2,4]triazolo[1,5-a]pyridin-2-amine

To a stirred solution of 5-phenylpyridin-2-amine (1.8 g, 10.57 mmol) in 1,4-dioxane (20.0 mL) was added ethylthiocarbonyl isothiocynate (1.18 mL, 10.57 mmol) drop-wise at 25° C. The reaction was stirred at 25° C. for 16 h. The resulting mixture was diluted with water (200 mL) and extracted in EtOAc (100 mL×2). The organic layer was washed with brine (20 mL), dried over anhydrous sodium sulfate and distilled off to give the thiourea derivative (3.8 g) as a light yellow solid which was immediately used without purification. To a solution of hydroxylamine HCl (4.38 g, 63.04 mmol) in MeOH:EtOH (20:20 mL) was added DIPEA (6.5 mL, 37.82 mmol) drop-wise followed by the thiourea derivative (3.8 g, 12.60 mmol). The reaction mixture was stir at 25° C. for 16 h and then concentrated. The crude product was diluted with water (300 mL) and extracted in EtOAc (300 mL×2). The organic layer was washed with brine (20 mL), dried over anhydrous sodium sulfate and distilled off to give 6-phenyl-[1,2,4]triazolo[1, 5-a]pyridin-2-amine as a light brown solid (2.0 g, 211.24 [M+H]).

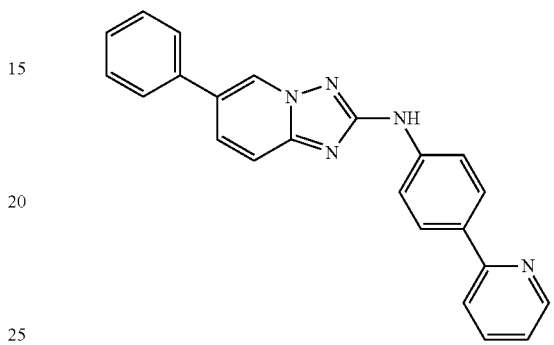

Example 100: 6-phenyl-N-(4-(pyridin-2-yl)phenyl)-[1,2,4]triazolo[1,5-a]pyridin-2-amine Prepared a stirred solution of 6-phenyl-[1,2,4]triazolo[1, 5-a]pyridin-2-amine (500 mg, 2.13 mmol), 2-(4-bromophenyl)pyridine (538 mg, 2.56 mmol), davephos (142 mg, 0.36 mmol) and CS$_2$CO$_3$ (1.39 g, 4.27 mmol) in dry 1, 4 Dioxane (15 mL). The mixture was degassed with nitrogen and vacuum for 10 minutes. Pd(OAc)$_2$ (81.4 g, 0.36 mmol) was added and the reaction mixture was heated at 90° C. for 16 h. The crude reaction was cooled to 25° C., diluted with water (200 mL) and extracted in EtOAc (50 mL×2). The organic layer was washed with brine (20 mL), dried over anhydrous sodium sulfate and distilled off to give crude product which was purified by Flash chromatography to give pure 6-phenyl-N-(4-(pyridin-2-yl)phenyl)-[1,2,4]triazolo[1, 5-a]pyridin-2-amine (29 mg, 363.42 [M+H]). $^1$H NMR: (400 MHz, DMSO) (32904) δ: 7.26-7.29 (m, 1H), 7.42-7.44 (m, 1H), 7.51-7.53 (m, 1H), 7.68-7.70 (m, 1H), 7.81-7.86 (m, 5H), 7.91-7.93 (m, 1H), 7.95-7.98 (m, 1H), 8.06-8.08 (m, 2H), 8.62-8.63 (m, 1H), 9.20-9.22 (m, 1H), 9.94 (s, 1H).

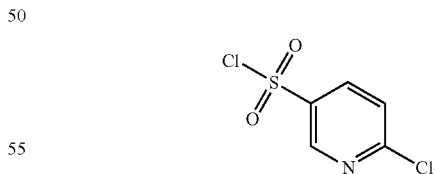

6-chloropyridine-3-sulfonyl chloride

Thionyl chloride (60 mL, 822.9 mmol) was added to water (361 mL) over 60 min at 0° C. while maintaining the temperature between 0° C. to 7° C. The solution was stirred at 15° C. for 16 hr. Next, Cu(I)Cl (0.218 g, 1.94 mmol) was added and the reaction was cooled to −3° C. In a separate flask, a stirred solution of 6-chloropyridin-3-amine (25.0 g, 194.5 mmol) in conc. HCl (195 ml) was cooled to −5° C. and a solution of sodium nitrite (14.4 g, 208.1 mmol) in water (58 ml) was added drop wise over 45 min while maintaining the temperature between −5° to 0° C. The resulting slurry was cooled to −2° C., stirred for 10 min and subsequently added to the first flask over 95 minutes while maintaining the temperature between −3° to 0° C. Once the addition was complete the reaction mixture was stirred at 0° C. for 75 min. The resulting solid precipitate was filtered, washed with water and dried over vacuum to give 6-chloropyridine-3-sulfonyl chloride (26.0 g). $^1$H NMR: (400 MHz, DMSO) (35756) δ: 7.484-7.507 (dd, J=1.6, 8.4 1H), 7.956-7.983 (dd, J=2.4, 8.4 1H), 8.551-8.559 (dd, J=0.8, 2.4 1H).

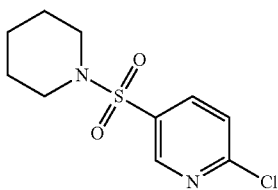 [SMILES: O=S(=O)(c1ccc(Cl)nc1)N1CCCCC1]

2-chloro-5-(piperidin-1-ylsulfonyl)pyridine

To a stirred solution of piperidine (5.3 mL, 51.8 mmol) in dichloromethane (80 mL) was added TEA (19.84 mL, 141.4 mmol) and the solution stirred for 30 min at 25° C. A solution of 6-chloropyridine-3-sulfonyl chloride (10 g, 47.1 mmol) in dichloromethane (50 mL) was added at 0° C. and the mixture was stirred at 25° C. for 1 h. The reaction mixture was diluted with water (500 mL) and extracted in dichloromethane (250 mL×2). The organic layer was washed with brine (250 mL), dried over anhydrous sodium sulfate and evaporated to give 2-chloro-5-(piperidin-1-ylsulfonyl)pyridine (12 g).

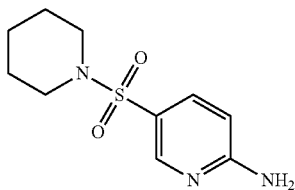 [SMILES: Nc1ccc(S(=O)(=O)N2CCCCC2)cn1]

5-(piperidin-1-ylsulfonyl)pyridin-2-amine

Prepared a stirred solution of 2-chloro-5-(piperidin-1-ylsulfonyl)pyridine (3.7 g, 14.19 mmol) in aqueous ammonia (40 mL) that was heated at 100° C. for 72 h. The reaction mixture cooled to 25° C., diluted with water (100 mL) and extracted in EtOAc (150 mL×2). The organic layer was washed with brine (100 mL), dried over anhydrous sodium sulfate and distilled off to obtained 5-(piperidin-1-ylsulfonyl)pyridin-2-amine (3.0 g). 1H NMR: (400 MHz, DMSO) (6742) δ: 1.366-1.394 (m, 2H), 1.513-1.554 (m, 4H), 2.814-2.841 (m, 4H), 6.508-6.531 (d, 9.2 Hz, 1H), 6.964 (s, 2H), 7.586-7.614 (m, 1H), 8.184 (s, 1H).

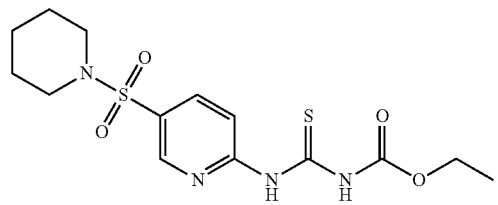 [SMILES: CCOC(=O)NC(=S)Nc1ccc(S(=O)(=O)N2CCCCC2)cn1]

To a stirred solution of 5-(piperidin-1-ylsulfonyl)pyridin-2-amine (3.0 g, 12.43 mmol) in dioxane (30 mL) was added ethoxycarbonyl isothiocynate (1.5 mL, 12.43 mmol) at 25° C. under nitrogen atmosphere and the resulting reaction mixture was stirred at 25° C. for 16 h. The solvent was distilled off to obtain crude product which was purified by column chromatography (20% ethyl acetate in hexane) to obtain the thio-urea derivative (3.8 g) as off white solid.

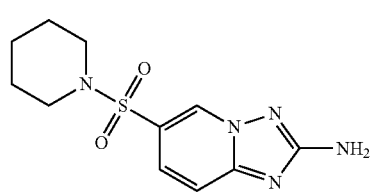 [SMILES: Nc1nc2ccc(S(=O)(=O)N3CCCCC3)cn2n1]

6-(piperidin-1-ylsulfonyl)-[1,2,4]triazolo[1,5-a]pyridin-2-amine

To a stirred solution of hydroxylamine hydrochloride (3.54 g, 51.01 mmol) in methanol (20 mL) and ethanol (20 mL) was added DIPEA (5.23 mL, 30.60 mmol) drop wise at 25° C. The thio-urea derivative (3.8 g, 10.20 mmol) was then added in one portion at 25° C. and the resulting reaction mixture was stirred at 25° C. for 2 h and then heated at 60° C. for 16 h. Solvent was distilled off, and the crude reaction mass was diluted with water (100 mL) and stirred for 10 minutes. The resulting solid was filtered to obtained 6-(piperidin-1-ylsulfonyl)-[1,2,4]triazolo[1,5-a]pyridin-2-amine (2.6 g, 281.79 [M+]). 1H NMR: (400 MHz, DMSO) (7947) δ: 1.378-1.389 (m, 2H), 1.551 (s, 4H), 2.959-2.985 (m, 4H), 6.475 (s, 2H), 7.494-7.517 (d, 9.2 Hz, 1H), 7.608-7.635 (m, 1H), 8.931 (s, 1H).

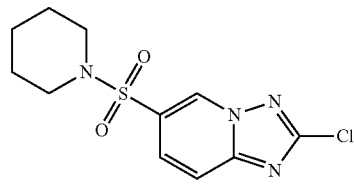 [SMILES: O=S(=O)(c1ccc2nc(Cl)nn2c1)N1CCCCC1]

2-chloro-6-(piperidin-1-ylsulfonyl)-[1,2,4]triazolo[1,5-a]pyridine

To a stirred solution of 6-(piperidin-1-ylsulfonyl)-[1,2,4]triazolo[1,5-a]pyridin-2-amine (0.2 g, 0.71 mmol) in HCl (4 mL) was added copper(II)chloride dehydrate (0.032 g, 0.18 mmol) at 25° C. The resulting reaction mixture was cooled to 5° C. and a solution of sodium nitrate (0.059 g, 0.85 mmol) in water (2 mL) was added. The resulting reaction mixture was stirred at 5° C. for 30 minutes and then at 25° C. for 16 h. The crude reaction mass was diluted with water (100 mL) and stirred for 10 minutes. The resulting solid was filtered to obtained 2-chloro-6-(piperidin-1-ylsulfonyl)-[1,2,4]triazolo[1,5-a]pyridine (0.15 g, 301.3 [M+1]). 1H NMR: (400 MHz, DMSO) (9016) δ: 1.377-1.391 (d, 5.6 Hz, 2H), 1.529-1.584 (m, 4H), 3.018-3.045 (t, 5.6 Hz, 4H), 7.937-7.965 (m, 1H), 8.008-8.034 (m, 1H), 9.443-9.449 (m, 1H).

Example 101: N-(benzo[d][1,3]dioxol-5-ylmethyl)-6-(piperidin-1-ylsulfonyl)-[1,2,4]-triazolo[1,5-a]pyridin-2-amine A stirred solution of 2-chloro-6-(piperidin-1-ylsulfonyl)-[1,2,4]triazolo[1,5-a]pyridine (0.1 g, 0.33 mmol) in benzo[d][1,3]dioxol-5-ylmethanamine (0.1 mL) was heated at 140° C. for 16 h. The reaction mixture was cooled, diluted with water (50 mL) and extracted in dichloromethane (25 mL×2). The organic layer was washed with brine (20 mL), dried over anhydrous sodium sulfate and distilled off to give crude product which was purified by prep HPLC to give pure N-(benzo[d][1,3]dioxol-5-ylmethyl)-6-(piperidin-1-1.5 ylsulfonyl)-[1,2,4]triazolo[1,5-a]pyridin-2-amine as an off white solid (60 mg, 415.75 [M+H]). $^1$H NMR: (400 MHz, DMSO) (15874) δ: 1.37-1.38 (m, 2H), 1.53-1.54 (m, 4H), 2.95-2.97 (m, 4H), 4.38-4.39 (d, J=6.4 Hz, 2H), 5.96 (s, 2H), 6.81-6.86 (m, 2H), 6.92 (s, 1H), 7.52-7.58 (m, 2H), 7.62-7.65 (m, 1H), 8.97-8.98 (d, J=1.2 Hz, 1H).

Representative compounds of the invention were prepared in a similar manner to example 101 from 2-chloro-6-(piperidin-1-ylsulfonyl)-[1,2,4]triazolo[1,5-a]pyridine and the appropriate amine.

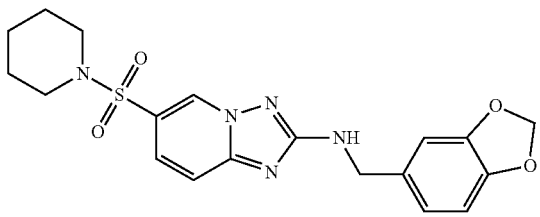 [SMILES: O=S(=O)(c1ccc2nc(NCc3ccc4c(c3)OCO4)nn2c1)N1CCCCC1]

| No. | Structure | LCMS m/z |
|---|---|---|
| 102 | 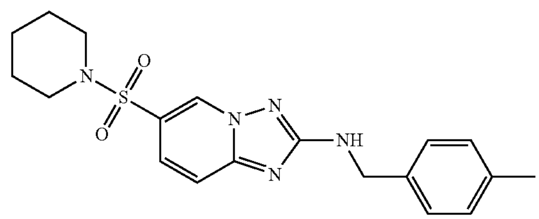 [SMILES: Cc1ccc(CNc2nc3ccc(S(=O)(=O)N4CCCCC4)cn3n2)cc1] | 386 |
| 103 | 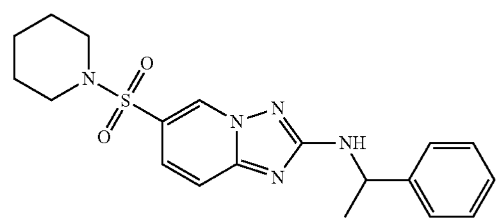 [SMILES: CC(Nc1nc2ccc(S(=O)(=O)N3CCCCC3)cn2n1)c1ccccc1] | 386 |
| 104 | 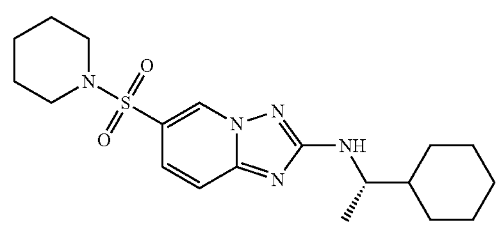 [SMILES: C[C@H](Nc1nc2ccc(S(=O)(=O)N3CCCCC3)cn2n1)C1CCCCC1] | 392 |
| 107 | 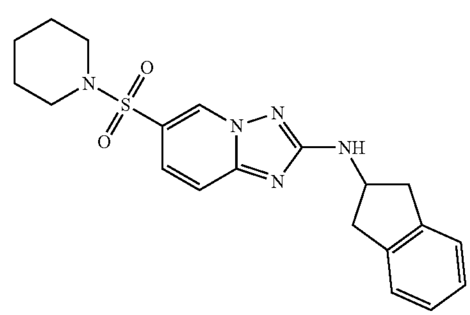 [SMILES: O=S(=O)(c1ccc2nc(NC3Cc4ccccc4C3)nn2c1)N1CCCCC1] | 398 |

| No. | Structure | LCMS m/z |
|---|---|---|
| 108 | 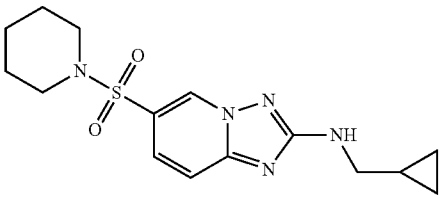 [SMILES: O=S(=O)(c1ccc2nc(NCC3CC3)nn2c1)N1CCCCC1] | 336 |
| 109 | 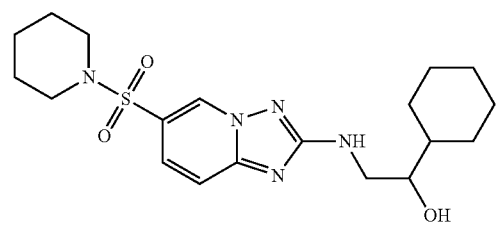 [SMILES: O=S(=O)(c1ccc2nc(NCC(O)C3CCCCC3)nn2c1)N1CCCCC1] | 408 |

Assays for Detecting and Measuring the Effect of Compounds on dF508-CFTR Channels CFRT-YFP High Throughput Assay:

Corrector Assay:

The following protocol is designed to selectively screen small molecule compounds for F508del CFTR corrector activities in the HTS YFP flux assay. In this protocol, the cells are incubated with testing compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta, 2001), and was adapted to the HTS format (Sui, 2010).

Fisher Rat Thyroid (FRT) cells stably expressing both human ΔF508-CFTR and a halide-sensitive yellow fluorescent protein (YFP-H148Q/I152L 25, 22) (Galietta, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 μg/mL) were used for selection of FRT cells expressing ΔF508-CFTR and YFP. For primary screening, FRT cells were plated into 384-well black wall, transparent bottom microtiter plates (Costar; Corning Inc.) at a cell density of 20, 000-40, 000 per well. Test compound was applied to the cells at varying concentrations ranging from 2 nM-40 nM in either a 2-fold or 3-fold dilution series. Cells were incubated in a cell culture incubator at 37° C. with 5% $CO_2$ for 24-26 h. Assay plates were washed with DPBS media (Thermo, cat#SH30028.02) to remove unbound cells and compound. Stimulation media (25 μL) containing 20 μM Forskolin & 30 μM P3 [6-(Ethyl-phenyl-sulfonyl)-4-oxo-1, 4-dihydro-quinoline-3-carboxylic acid 2-methoxy-benzylamide] in Hams F-12 coon's modified media was added to the plate wells and incubated at room temperature for 60-120 min. 25 μL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data (Sui, 2010).

Potentiator Assay:

The following protocol is designed to selectively screen small molecule compounds for F508del CFTR potentiator activities in the HTS YFP flux assay. In this protocol, the cells are incubated at 27° C. for 24 hours with homogeneously boosted dF508-CFTR expression in the cell membrane by the low temperature, washed with PBS, stimulated with forskolin, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508del-CFTR potentiators accelerate YFP quenching by increasing CFTR activities in the testing cell plasma membrane.

This method was initially developed for bench top plate readers (Galietta, 2001), and was adapted to the HTS format (Sui, 2010).

Fisher Rat Thyroid (FRT) cells stably expressing both human ΔF508-CFTR and a halide-sensitive yellow fluorescent protein (YFP-H148Q/I152L 25, 22) (Galietta, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 μg/mL) were used for selection of FRT cells expressing ΔF508-CFTR and YFP. For primary screening, FRT cells were plated into 384-well black wall, transparent bottom microtiter plates (Costar; Corning Inc.) at a cell density of 20, 000-40, 000 per well. Cells were incubated in a cell culture incubator at 37° C. with 5% $CO_2$ for 24-26 h. Assay plates were washed with DPBS media (Thermo, cat# SH30028.02) to remove unbound cells. Test compound was applied to the cells at varying concentrations ranging from 2 nM-40 nM in either a 2-fold or 3-fold dilution series in DPBS and stimulated with 20 µM Forskolin (final concentration) in Hams F-12 coon's modified media. Plates were incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data (Sui, 2010).

REFERENCES

Galietta, L. V., Jayaraman, S., and Verkman, A. S. Cell-based assay for high-throughput quantitative screening of CFTR chloride transport agonists. Am. J. Physiol. Cell Physiol. 281(5), C1734-42, 2001.

Sui J., Cotard S., Andersen J., Zhu P., Staunton J., Lee M., Lin S. (2010) Optimization of a Yellow fluorescent protein-based iodide influx high-throughput screening assay for cystic fibrosis transmembrane conductance regulator (CFTR) modulators. Assay Drug Dev. Technol. 2010 December; 8(6): 656-68.

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay test compounds were added to the basolateral surface of the cells at various test concentrations dissolved in DMSO. The same concentrations of correctors was added to 3 or 4 wells giving a n=3 or n=4 protocol.

Ussing Assay:

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage stabilizes adjusts before application of voltage clamp.

Compounds were added in the following order:

| Step | Chamber |
|---|---|
| 3.0 µM Benzamil for 20 minutes | apical addition only |
| 10 µM Forskolin for 20 minutes | apical + basolateral addition |
| 10 µM Genestein for 20 minutes | apical + basolateral addition |
| 10 µM CFTR-172 for 20 minutes | apical + basolateral addition |
| 20 µM Bumetanide for 30 minutes | basolateral addition only |

The short circuit current and resistances (typically >300 Ω-cm2) from each chamber was recorded every 10 seconds on stored on a PC using Acquire and Analyze (Physiologic Instruments).

Analysis:

Efficacy of test compounds was compared using the average of the forskolin response and the CFTR-172 response of the test compound divided by the average of the forskolin response and the CFTR-172 elicited by the positive control. Normalized scores were tabulated for all compounds and concentrations.

TABLE I

CFTR-YFP High Throughput Assay; The following meanings apply: % Efficacy is reported as the EMax normalized to the positive control. "+++" refers to EMax >80%, "++" refers to a range of 80%-40%, "+" refers to a range of 40%-10%. $EC_{50}$: "+++" refers to $EC_{50}$ <1 µM, "++" refers to $EC_{50}$ range of between 1-10 µM, "+" refers to $EC_{50}$ >10 µM.

| Example No. | Emax | Ec50 |
|---|---|---|
| 1 | +++ | +++ |
| 2 | +++ | +++ |
| 3 | ++ | +++ |
| 4 | +++ | +++ |
| 5 | +++ | +++ |
| 6 | ++ | ++ |
| 7 | ++ | +++ |
| 8 | +++ | +++ |
| 9 | +++ | +++ |
| 10 | +++ | +++ |
| 11 | +++ | +++ |
| 12 | ++ | ++ |
| 13 | ++ | +++ |
| 14 | ++ | + |
| 15 | ++ | + |
| 16 | ++ | +++ |
| 17 | +++ | +++ |
| 18 | ++ | ++ |
| 19 | +++ | +++ |
| 20 | +++ | +++ |
| 21 | +++ | +++ |
| 22 | ++ | +++ |
| 23 | +++ | + |
| 24 | +++ | ++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | ++ | ++ |
| 32 | ++ | ++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | +++ | +++ |
| 40 | +++ | +++ |
| 41 | +++ | +++ |
| 42 | +++ | +++ |
| 43 | +++ | +++ |
| 44 | +++ | +++ |
| 45 | +++ | +++ |
| 46 | ++ | +++ |
| 47 | ++ | +++ |
| 48 | +++ | +++ |
| 49 | +++ | +++ |
| 50 | +++ | +++ |
| 51 | +++ | +++ |
| 52 | +++ | ++ |
| 53 | +++ | +++ |
| 54 | +++ | ++ |
| 55 | + | +++ |
| 56 | +++ | +++ |
| 57 | ++ | ++ |
| 58 | ++ | +++ |
| 59 | ++ | +++ |
| 60 | +++ | +++ |
| 61 | + | ++ |
| 62 | +++ | +++ |
| 63 | ++ | +++ |
| 64 | +++ | +++ |
| 65 | +++ | +++ |
| 66 | +++ | +++ |

TABLE I-continued

CFTR-YFP High Throughput Assay; The following meanings apply:
% Efficacy is reported as the EMax normalized to the positive control.
"+++" refers to EMax >80%, "++" refers to a range of 80%-40%,
"+" refers to a range of 40%-10%. $EC_{50}$: "+++" refers to
$EC_{50}$ <1 µM, "++" refers to $EC_{50}$ range of between
1-10 µM, "+" refers to $EC_{50}$ >10 µM.

| Example No. | Emax | Ec50 |
|---|---|---|
| 67 | +++ | +++ |
| 68 | +++ | +++ |
| 69 | +++ | +++ |
| 70 | +++ | +++ |
| 71 | +++ | ++ |
| 72 | +++ | ++ |
| 73 | +++ | +++ |
| 74 | +++ | +++ |
| 75 | +++ | +++ |
| 76 | +++ | ++ |
| 77 | +++ | +++ |
| 78 | +++ | +++ |
| 79 | +++ | ++ |
| 80 | +++ | +++ |
| 81 | +++ | +++ |
| 82 | +++ | +++ |
| 83 | +++ | +++ |
| 84 | +++ | ++ |
| 85 | +++ | +++ |
| 86 | +++ | +++ |
| 87 | +++ | +++ |
| 88 | +++ | +++ |
| 89 | +++ | ++ |
| 90 | ++ | ++ |
| 91 | ++ | +++ |
| 92 | ++ | ++ |
| 93 | +++ | +++ |
| 94 | +++ | +++ |
| 97 | ++ | ++ |
| 100 | ++ | ++ |
| 101 | +++ | ++ |
| 102 | +++ | +++ |

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed:

1. A compound of Formula VI or VIA:

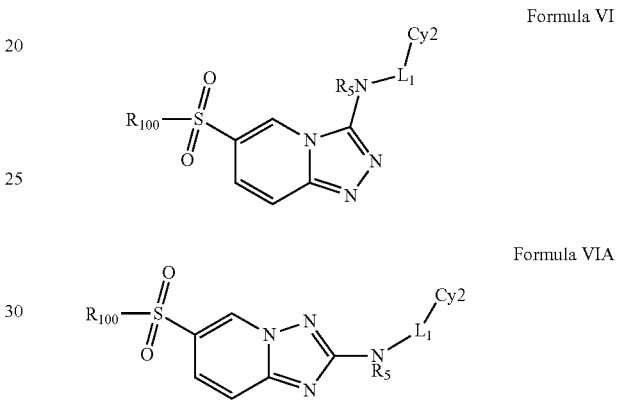

or a pharmaceutically acceptable salt thereof;
wherein:
$L_1$ is absent or a substituted or unsubstituted $C_1$-$C_2$-alkylene;
Cy2 is selected from aryl, substituted aryl, heteroaryl, substituted heteroaryl, heterocyclic, substituted heterocyclic, carbocyclic and substituted carbocyclic;
$R_5$ is hydrogen or methyl; and
$R_{100}$ is selected from aryl and substituted aryl.

2. A compound selected from Table A or a pharmaceutically acceptable salt thereof:

TABLE A

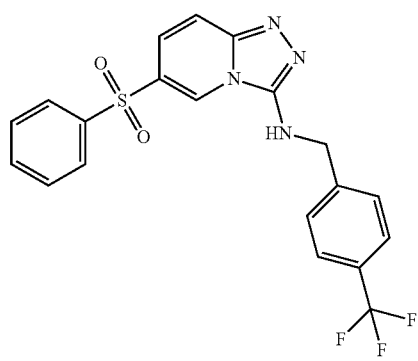 [SMILES: O=S(=O)(c1ccccc1)c1ccc2nnc(NCc3ccc(C(F)(F)F)cc3)n2c1]

TABLE A-continued
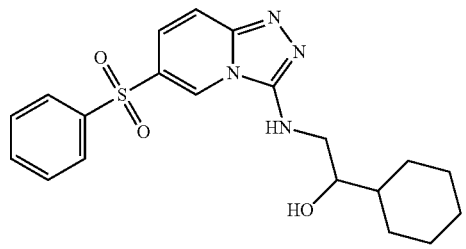 [SMILES: O=S(=O)(c1ccccc1)c1ccc2nnc(NCC(O)C3CCCCC3)n2c1]
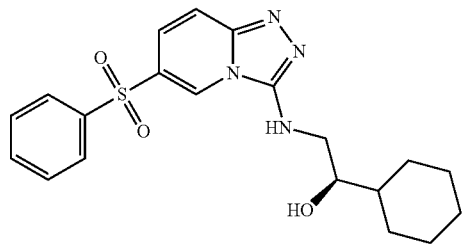 [SMILES: O=S(=O)(c1ccccc1)c1ccc2nnc(NC[C@H](O)C3CCCCC3)n2c1]
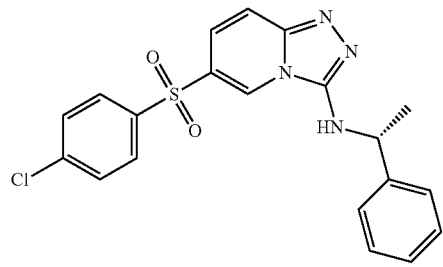 [SMILES: C[C@@H](Nc1nnc2ccc(S(=O)(=O)c3ccc(Cl)cc3)cn12)c1ccccc1]
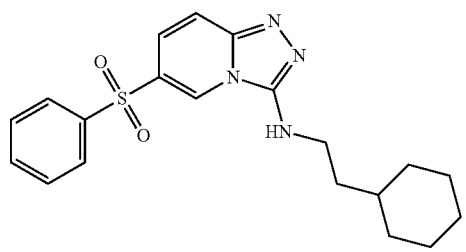 [SMILES: O=S(=O)(c1ccccc1)c1ccc2nnc(NCCC3CCCCC3)n2c1]
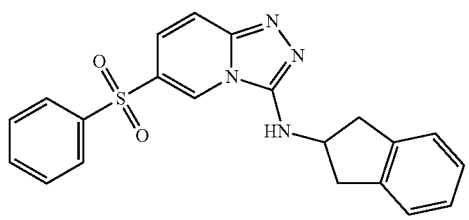 [SMILES: O=S(=O)(c1ccccc1)c1ccc2nnc(NC3Cc4ccccc4C3)n2c1]
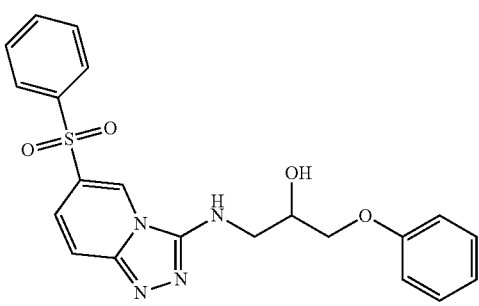 [SMILES: O=S(=O)(c1ccccc1)c1ccc2nnc(NCC(O)COc3ccccc3)n2c1]

TABLE A-continued
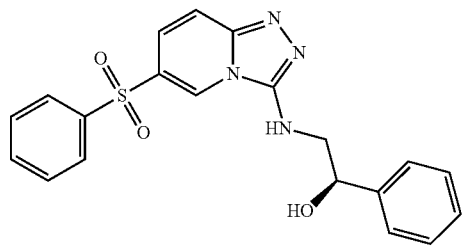 [SMILES: O=S(=O)(c1ccccc1)c1ccc2nnc(NC[C@H](O)c3ccccc3)n2c1]
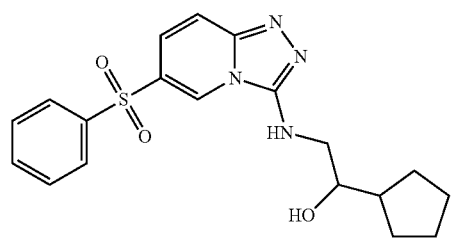 [SMILES: O=S(=O)(c1ccccc1)c1ccc2nnc(NCC(O)C3CCCC3)n2c1]
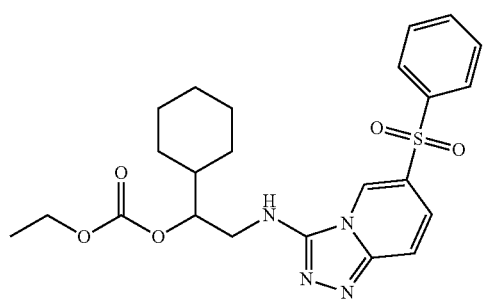 [SMILES: CCOC(=O)OC(CNc1nnc2ccc(S(=O)(=O)c3ccccc3)cn12)C1CCCCC1]
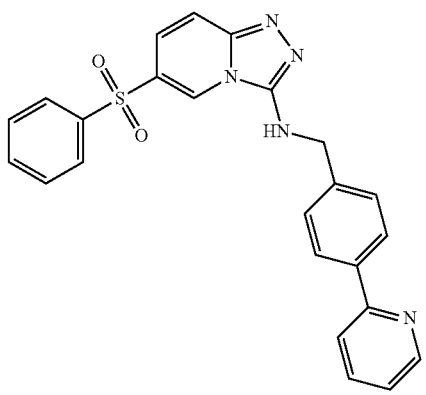 [SMILES: O=S(=O)(c1ccccc1)c1ccc2nnc(NCc3ccc(-c4ccccn4)cc3)n2c1]
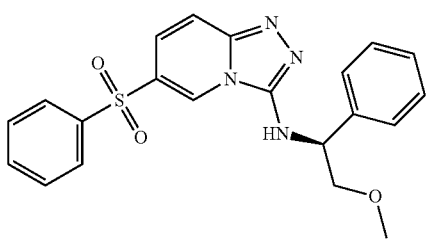 [SMILES: COC[C@@H](Nc1nnc2ccc(S(=O)(=O)c3ccccc3)cn12)c1ccccc1]

TABLE A-continued
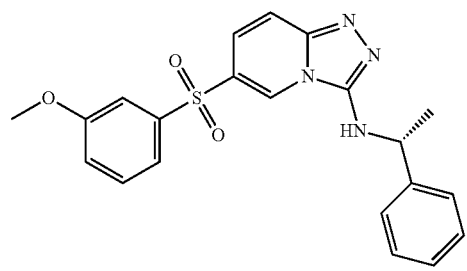 [SMILES: COc1cccc(S(=O)(=O)c2ccc3nnc(N[C@H](C)c4ccccc4)n3c2)c1]
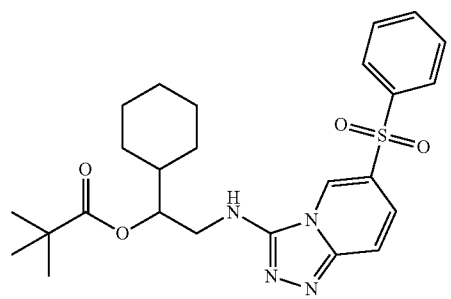 [SMILES: CC(C)(C)C(=O)OC(CNc1nnc2ccc(S(=O)(=O)c3ccccc3)cn12)C1CCCCC1]
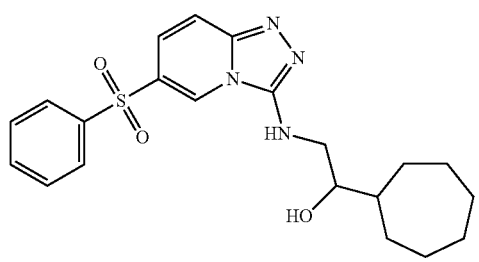 [SMILES: O=S(=O)(c1ccccc1)c1ccc2nnc(NCC(O)C3CCCCCC3)n2c1]
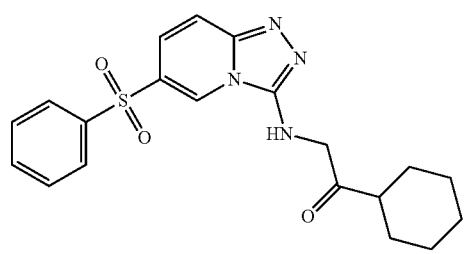 [SMILES: O=C(CNc1nnc2ccc(S(=O)(=O)c3ccccc3)cn12)C1CCCCC1]
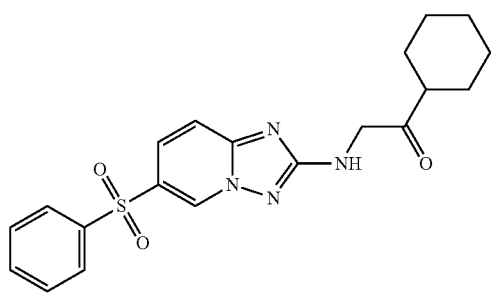 [SMILES: O=C(CNc1nc2ccc(S(=O)(=O)c3ccccc3)cn2n1)C1CCCCC1]

TABLE A-continued
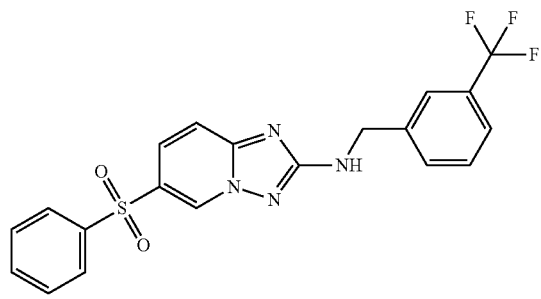 [SMILES: O=S(=O)(c1ccccc1)c1ccc2nc(NCc3cccc(C(F)(F)F)c3)nn2c1]
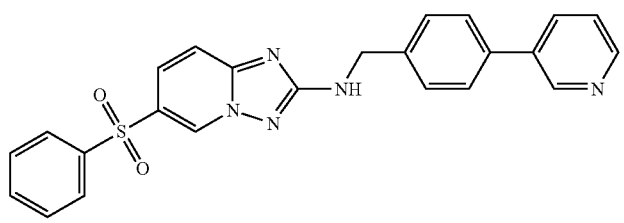 [SMILES: O=S(=O)(c1ccccc1)c1ccc2nc(NCc3ccc(-c4cccnc4)cc3)nn2c1]
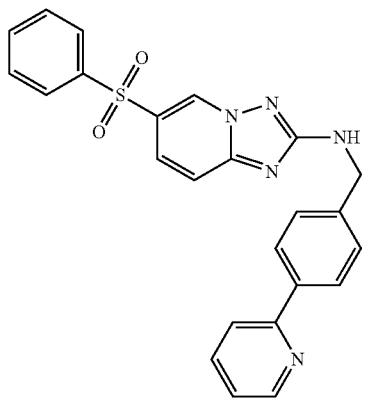 [SMILES: O=S(=O)(c1ccccc1)c1ccc2nc(NCc3ccc(-c4ccccn4)cc3)nn2c1]
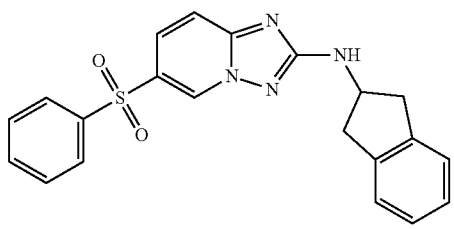 [SMILES: O=S(=O)(c1ccccc1)c1ccc2nc(NC3Cc4ccccc4C3)nn2c1]
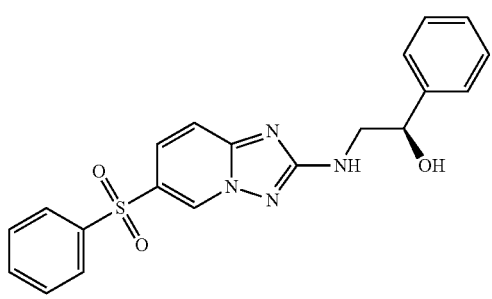 [SMILES: O=S(=O)(c1ccccc1)c1ccc2nc(NC[C@H](O)c3ccccc3)nn2c1]

TABLE A-continued
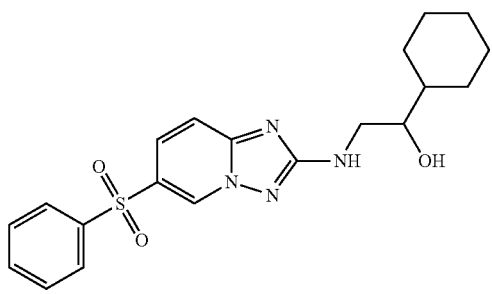 [SMILES: O=S(=O)(c1ccccc1)c1ccc2nc(NCC(O)C3CCCCC3)nn2c1]
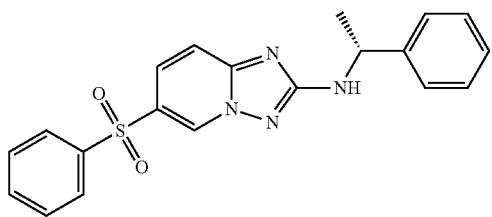 [SMILES: C[C@@H](Nc1nc2ccc(S(=O)(=O)c3ccccc3)cn2n1)c1ccccc1]
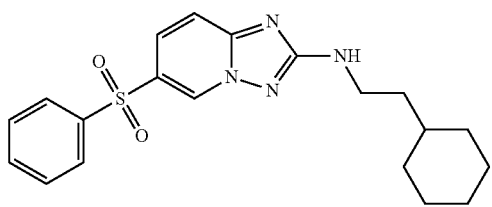 [SMILES: O=S(=O)(c1ccccc1)c1ccc2nc(NCCC3CCCCC3)nn2c1]
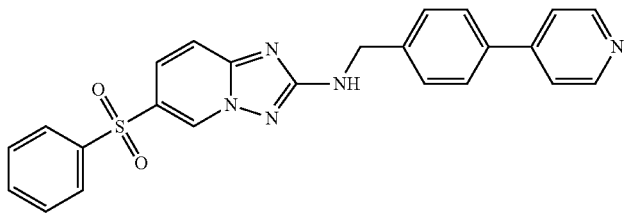 [SMILES: O=S(=O)(c1ccccc1)c1ccc2nc(NCc3ccc(-c4ccncc4)cc3)nn2c1]
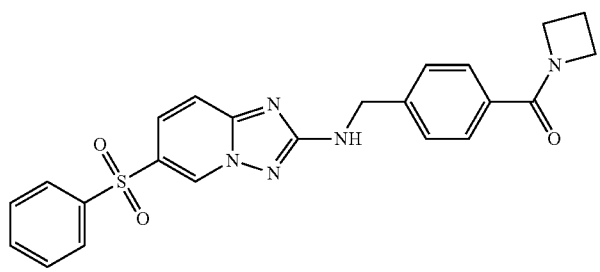 [SMILES: O=C(c1ccc(CNc2nc3ccc(S(=O)(=O)c4ccccc4)cn3n2)cc1)N1CCC1]
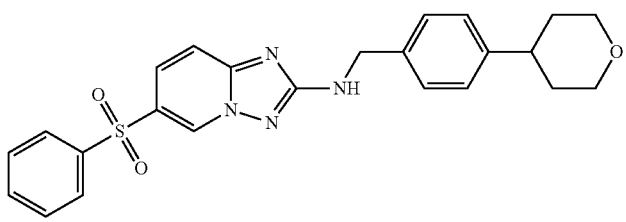 [SMILES: O=S(=O)(c1ccccc1)c1ccc2nc(NCc3ccc(C4CCOCC4)cc3)nn2c1]

TABLE A-continued
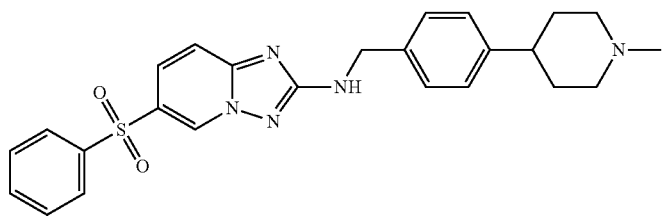 [SMILES: CN1CCC(c2ccc(CNc3nc4ccc(S(=O)(=O)c5ccccc5)cn4n3)cc2)CC1]
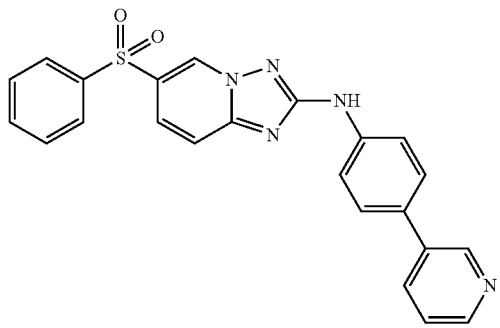 [SMILES: O=S(=O)(c1ccccc1)c1ccc2nc(Nc3ccc(-c4cccnc4)cc3)nn2c1]
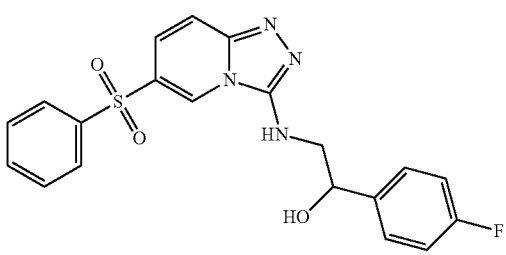 [SMILES: O=S(=O)(c1ccccc1)c1ccc2nnc(NCC(O)c3ccc(F)cc3)n2c1]
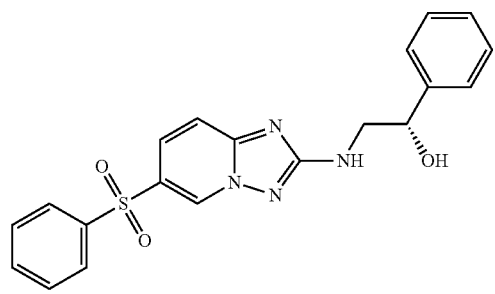 [SMILES: O=S(=O)(c1ccccc1)c1ccc2nc(NC[C@@H](O)c3ccccc3)nn2c1]
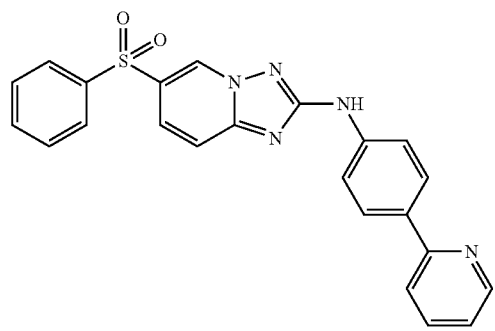
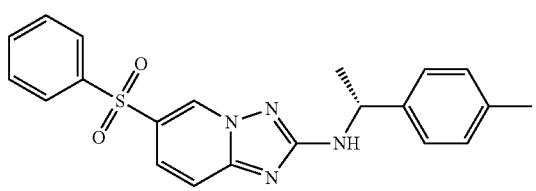 [SMILES: Cc1ccc([C@@H](C)Nc2nc3ccc(S(=O)(=O)c4ccccc4)cn3n2)cc1]

TABLE A-continued

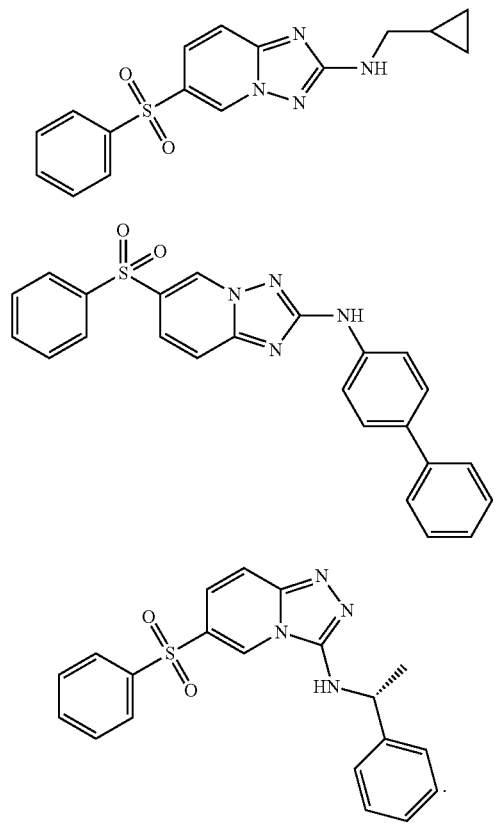

3. A pharmaceutical composition comprising a compound according to claim 1 and a pharmaceutically acceptable carrier.

4. A composition comprising a compound according to claim 1 in combination with one or more compounds that modulate activity or expression of CFTR or disease-causing variants thereof.

5. A composition comprising a compound according to claim 1 in combination with a second compound that is a modulator of the cystic fibrosis transmembrane conductance regulator gene.

6. The composition according to claim 5, wherein said second compound is selected from gentamicin, genestein, ataluren, ivacaftor, VX-661 and VX-809, or a combination thereof.

7. The compound according to claim 1, wherein Cy2 is selected from:

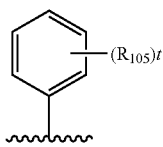 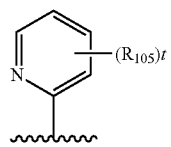 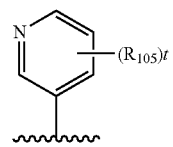

-continued

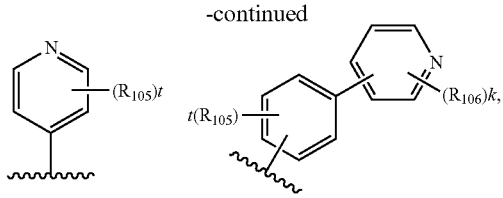

wherein
t is 1, 2, 3, or 4;
k is 1, 2, 3, or 4; and
each $R_{105}$ and $R_{106}$ is independently selected from hydrogen, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl.

8. The compound according to claim 7, wherein Cy2 is

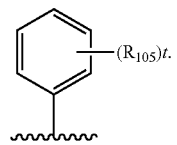

9. The compound according to claim 1, wherein $L_1$ is optionally substituted $C_1$-$C_2$-alkylene.

* * * * *